US009322027B2

(12) United States Patent
Shock et al.

(10) Patent No.: US 9,322,027 B2
(45) Date of Patent: Apr. 26, 2016

(54) EXPRESSION CONSTRUCTS COMPRISING FUNGAL PROMOTERS

(75) Inventors: Jennifer L. Shock, San Francisco, CA (US); Louis Clark, San Francisco, CA (US)

(73) Assignee: Shell Oil Company, Houston, TX (US)

( * ) Notice: Subject to any disclaimer, the term of this patent is extended or adjusted under 35 U.S.C. 154(b) by 582 days.

(21) Appl. No.: 13/214,406

(22) Filed: Aug. 22, 2011

(65) Prior Publication Data

US 2012/0045793 A1    Feb. 23, 2012

Related U.S. Application Data

(60) Provisional application No. 61/375,702, filed on Aug. 20, 2010, provisional application No. 61/375,745, filed on Aug. 20, 2010, provisional application No. 61/375,753, filed on Aug. 20, 2010, provisional application No. 61/375,755, filed on Aug. 20, 2010, provisional application No. 61/375,760, filed on Aug. 20, 2010.

(51) Int. Cl.
*C12N 15/80* (2006.01)
*C07K 14/37* (2006.01)

(52) U.S. Cl.
CPC ............... *C12N 15/80* (2013.01); *C07K 14/37* (2013.01)

(58) Field of Classification Search
None
See application file for complete search history.

(56) References Cited

U.S. PATENT DOCUMENTS

| | | | |
|---|---|---|---|
| 5,605,793 A | 2/1997 | Stemmer | |
| 5,811,238 A | 9/1998 | Stemmer et al. | |
| 5,811,381 A | 9/1998 | Emalfarb et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,928,905 A | 7/1999 | Stemmer et al. | |
| 6,015,707 A | 1/2000 | Emalfarb et al. | |
| 6,096,548 A | 8/2000 | Stemmer | |
| 6,117,679 A | 9/2000 | Stemmer | |
| 6,132,970 A | 10/2000 | Stemmer | |
| 6,165,793 A | 12/2000 | Stemmer | |
| 6,180,406 B1 | 1/2001 | Stemmer | |
| 6,251,674 B1 | 6/2001 | Tobin et al. | |
| 6,277,638 B1 | 8/2001 | Stemmer | |
| 6,287,839 B1 | 9/2001 | Jones et al. | |
| 6,287,861 B1 | 9/2001 | Stemmer et al. | |
| 6,287,862 B1 | 9/2001 | delCardayre et al. | |
| 6,291,242 B1 | 9/2001 | Stemmer | |
| 6,297,053 B1 | 10/2001 | Stemmer | |
| 6,303,344 B1 | 10/2001 | Patten et al. | |
| 6,309,883 B1 | 10/2001 | Minshull et al. | |
| 6,319,713 B1 | 11/2001 | Patten et al. | |
| 6,319,714 B1 | 11/2001 | Crameri et al. | |
| 6,323,030 B1 | 11/2001 | Stemmer | |
| 6,326,204 B1 | 12/2001 | Patten et al. | |
| 6,335,160 B1 | 1/2002 | Patten et al. | |
| 6,335,198 B1 | 1/2002 | delCardayre et al. | |
| 6,344,356 B1 | 2/2002 | Stemmer | |
| 6,352,859 B1 | 3/2002 | delCardayre et al. | |
| 6,355,484 B1 | 3/2002 | Patten et al. | |
| 6,358,740 B1 | 3/2002 | Patten et al. | |
| 6,358,742 B1 | 3/2002 | Stemmer | |
| 6,365,377 B1 | 4/2002 | Patten et al. | |
| 6,365,408 B1 | 4/2002 | Stemmer | |
| 6,368,861 B1 | 4/2002 | Crameri et al. | |
| 6,372,497 B1 | 4/2002 | Stemmer | |
| 6,376,246 B1 | 4/2002 | Crameri et al. | |
| 6,379,964 B1 | 4/2002 | delCardayre et al. | |
| 6,387,702 B1 | 5/2002 | Stemmer | |
| 6,391,552 B2 | 5/2002 | Stemmer | |
| 6,391,640 B1 | 5/2002 | Minshull et al. | |
| 6,395,547 B1 | 5/2002 | Stemmer | |
| 6,406,855 B1 | 6/2002 | Patten et al. | |
| 6,406,910 B1 | 6/2002 | Patten et al. | |
| 6,413,745 B1 | 7/2002 | Patten et al. | |
| 6,413,774 B1 | 7/2002 | Stemmer et al. | |
| 6,420,175 B1 | 7/2002 | Stemmer | |
| 6,423,542 B1 | 7/2002 | Crameri et al. | |
| 6,426,224 B1 | 7/2002 | Crameri et al. | |
| 6,436,675 B1 | 8/2002 | Welch et al. | |
| 6,444,468 B1 | 9/2002 | Stemmer | |
| 6,455,253 B1 | 9/2002 | Patten et al. | |
| 6,479,652 B1 | 11/2002 | Crameri et al. | |
| 6,482,647 B1 | 11/2002 | Stemmer | |
| 6,489,146 B2 | 12/2002 | Stemmer et al. | |
| 6,506,602 B1 | 1/2003 | Stemmer | |
| 6,506,603 B1 | 1/2003 | Stemmer | |
| 6,519,065 B1 | 2/2003 | Colbourne et al. | |
| 6,521,453 B1 | 2/2003 | Crameri et al. | |

(Continued)

FOREIGN PATENT DOCUMENTS

WO    95/22625 A1    8/1995
WO    97/35966 A1    10/1997

(Continued)

OTHER PUBLICATIONS

Berka et al., Comparative genomic analysis of the thermophilic biomass-degrading fungi Myceliophthora thermophila and Thielavia terrestris; Nature Biotechnology, vol. 29, pp. 922-297, 2011.*
DOE Sporotrichum thermophile genome sequence assembly v 1.0, Jun. 2009, http://genome.jgi-psf.org/Spoth1/Spoth1.info.html; accessed Sep. 28, 2014.*
Genbank Acession No. GT948882, CCWO8597.b1 CCWO Myceliophthora thermophila ATCC 42464 1% cellulose and 1% pectin pooled culture (H) Myceliophthora thermophila ATCC 42464 cDNA clone CCWO8597 5-, mRNA sequence, from www.ncbi.nlm.nih.gov dated Dec. 7, 2011.
Alper, H., et al., "Tuning genetic control through promoter engineering," Proc. Nat'l. Acad. Sci. USA, 102 (36):12678-83 [2005].
Altschul, S.F., et al., "Basic Local Alignment Search Tool," J. Mol. Biol., 215: 403-410 [1990].

(Continued)

*Primary Examiner* — Addison D Ault

(57) ABSTRACT

The present invention provides promoters derived from a filamentous fungus. These promoters have application in the fields of molecular biology, microbiology, fungal genetics and production of biofuels and other products.

14 Claims, 5 Drawing Sheets

(56) References Cited

U.S. PATENT DOCUMENTS

| | | |
|---|---|---|
| 6,528,311 B1 | 3/2003 | delCardayre et al. |
| 6,562,612 B2 | 5/2003 | Jones et al. |
| 6,573,086 B1 | 6/2003 | Emalfrab et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,157 B2 | 12/2009 | Davis et al. |
| 7,629,170 B2 | 12/2009 | delCardayre et al. |
| 7,696,411 B2 | 4/2010 | Sticklen et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,883,872 B2 | 2/2011 | Gusakov et al. |
| 7,904,249 B2 | 3/2011 | Selifonov et al. |
| 7,906,309 B2 | 3/2011 | Emalfarb et al. |
| 7,957,912 B2 | 6/2011 | Selifonov et al. |
| 2003/0162218 A1* | 8/2003 | Emalfarb et al. ............... 435/7.1 |
| 2007/0238155 A1* | 10/2007 | Gusakov et al. ............... 435/101 |
| 2008/0194005 A1 | 8/2008 | Emalfarb et al. |
| 2008/0220990 A1 | 9/2008 | Fox |
| 2009/0099079 A1 | 4/2009 | Emalfarb et al. |
| 2009/0312196 A1 | 12/2009 | Colbeck et al. |

FOREIGN PATENT DOCUMENTS

| | | |
|---|---|---|
| WO | 98/15633 A1 | 4/1998 |
| WO | 98/27230 A1 | 6/1998 |
| WO | 01/75767 A2 | 10/2001 |
| WO | 2008/073914 A2 | 6/2008 |
| WO | 2009/152336 A1 | 12/2009 |
| WO | 2010/107303 A2 | 9/2010 |

OTHER PUBLICATIONS

Altschul, S.F., et al., "Gapped BLAST and PSI-BLAST: a new generation of protein database search programs," Nucleic Acids Res., 25(17):3389-3402 [1997].

Bell, P.J., et al., "Facilitating functional analysis of the Saccharomyces cerevisiae genome using an EGFP-based promoter library and flow cytometry," Yeast, 15:1747-59 [1999].

Botstein, D., et al., "Strategies and applications of in vitro mutagenesis," Science, 229(4719):1193-1201 [1985].

Breves, R., et al., "Genes encoding two different beta-gludosidases of Thermoa naerobacter brockii are clustered in a common operon," Appl. Environ. Microbiology, 63(10):3902-3910 [1997].

Bron, P.A., et al., "Selection and Characterization of Conditionally Active Promoters in Lactobacillus plantarum, Using Alanine Racemase as a Promoter Probe," Appl. Environ. Microbiol., 70:310-17 [2004].

Carter, P., "Site-directed mutagenesis," Biochem. J., 237:1-7 [1986].

Christians, F.C., et al., "Directed evolution of thymidine kinase for AZT phosphorylation using DNA family shuffling," Nature Biotechnology, 17:259-264 [1999].

Crameri, A., et al., "DNA shuffling of a family of genes from diverse species accelerates directed evolution," Nature, 391:288-291 [1998].

Crameri, A., et al., "Improved green fluorescent protein by molecular evolution using DNA shuffling," Nature Biotechnology, 14:315-319 [1996].

Crameri, A., et al., "Molecular evolution of an arsenate detoxification pathway by DNA shuffling," Nature Biotechnology, 15:436-438 [1997].

Gaillardin, G., et al., "LEU2 directed expression of beta-galactosidase activity and phleomycin resistance in Yarrowia lipolytica," Curr. Genet., 11: 369-375 [1987].

Garg, A.K., "An Addition to the Genus *Chrysosporium corda*," Mycopathol., 30: 3-4 [1966].

Harris, P.V., et al., "Stimulation of Lignocellulosic Biomass Hydrolysis by Proteins of Glycoside Hydrolase Family 61: Structure and Function of a Large, Enigmatic Family," Biochem., 49(15):3305-16 [2010].

Jung, E.D., et al., "DNA sequences and expression in Streptomyces lividans of an exoglucanase gene and an endoglucanase gene from Thermomonospora fusca," Appl. Environ. Microbiol., 59:3032-3043 [1993].

Kramer, B., et al., "Different base/base mismatches are corrected with different efficiencies by the methyl-directed DNA mismatch-repair system," Cell, 38:879-887 [1984].

Lao, G., et al, "DNA Sequences of Three Beta-1,4-Endoglucanase Genes from Thermomonospora fusca," J. Bacteriol., 173(11):3397-3407 [1991].

Ling, M.M., et al., "Approaches to DNA mutagenesis: an overview," Anal. Biochem., 254(2):157-78 [1997].

McNabb, D.S., et al., "Dual Luciferase Assay System for Rapid Assessment of Gene Expression in Saccharomyces cerevisiae," Eukary. Cell, 4(9):1539-49 [2005].

Minshull, J., et al., "Protein evolution by molecular breeding," Current Opinion in Chemical Biology, 3:284-290 [1999].

Needleman, S.B., et al., "A General Method Applicable to the Search for Similarities in the Amino Acid Sequence of Two Proteins,", J. Mol. Biol., 48:443-453 [1970].

Pearson, W.R., "Improved tools for biological sequence comparison," Proc. Nat'l. Acad. Sci. USA, 85:2444-2448 [1988].

Punt, P.J. et al., "Intracellular and extracellular production of proteins in Aspergillus under the control of expression signals of the highly expressed Aspergillus nidulans gpdA gene," J. Biotechnol., 17:19-33 [1991].

Roberts, I.N., et al., "Expression of the *Escherichia coli* beta-glucuronidase gene in industrial and phytopathogenic filamentous fungi," Curr Genet.,15:177-80 [1989].

Smith, T.F., et al., "Comparison of Biosequences," Adv. Appl. Math., 2:482-489 [1981].

Smith, M., "In vitro mutagenesis," Ann. Rev. Genet., 19:423-462 [1985].

Stemmer, W.P.C., "DNA shuffling by random fragmentation and reassembly: In vitro recombination for molecular evolution," Proc. Natl. Acad. Sci., U.S.A., 91:10747-10751 [1994].

Stemmer, W.P.C., "Rapid evolution of a protein in vitro by DNA shuffling," Nature, 370:389-391 (1994).

Wells, J.A., et al., "Cassette mutagenesis: an efficient method for generation of multiple mutations at defined sites," Gene, 34:315-323 [1985].

Zhang, J-H., et al., "Directed evolution of an effective fucosidase from a galactosidase by DNA shuffling and screening," Proc. Natl. Acad. Sci., U.S.A., 94:4504-4509 [1997].

Zhu, T., et al., "Construction of two Gateway vectors for gene expression in fungi," Plasmid, 62:128-33 [2009].

* cited by examiner

FIGURE 1

```
ATGAAGGCTGCTGCGCTTTCCTGCCTCTTCGGCAGTACCCTTGCCGTTGCCAGGCGCCATTGAATCGAGAAAGGTTCACCAGAAGCCCCTC
 M  K  A  A  A  L  S  C  L  F  G  S  T  L  A  V  A  G  A  I  E  S  R  K  V  H  Q  K  P  L
 1234567890123456789012345678901234567890123456789012345678901234567890123456789012345678901234567890
          1         2         3         4         5         6         7         8         9

GCGAGATCTGAAACCTTTTTACCTCGCGGATGAATCCCAACGCCGTCTGGGCGGAGGCCTATGCCCAAGCCCAAGTCCTTTGTC
 A  R  S  E  P  F  Y  P  S  P  W  M  N  P  N  A  D  G  W  A  E  A  Y  A  Q  A  K  S  F  V
 1234567890123456789012345678901234567890123456789012345678901234567890123456789012345678901234567890
         10        11        12        13        14        15        16        17       1

TCCCAAATGACTCTGCTAGAGAAGGTCAACTTGACCACGGGAGTCGGCTGGGGCGCTGAGCAGTGCGTCGGCCAAGTGGGCGCGATCCCT
 S  Q  M  T  L  L  E  K  V  N  L  T  T  G  V  G  W  G  A  E  Q  C  V  G  Q  V  G  A  I  P
 1234567890123456789012345678901234567890123456789012345678901234567890123456789012345678901234567890
       19        20        21        22        23        24        25        26       2

CGCCCTTGGACTTCGCAGTCTGTGCATGCATGACTCCCCTCGGCATCCGGGGCGCAGACTACAACTCAGCGTTCCCCTCTGGCCAGACC
 R  L  G  L  R  S  L  C  M  H  D  S  P  L  G  I  R  G  A  D  Y  N  S  A  F  P  S  G  Q  T
 1234567890123456789012345678901234567890123456789012345678901234567890123456789012345678901234567890
       28        29        30        31        32        33        34        35        3

GTTGCTGCTACCTGGGATCGCGGTCTGATGTACCGTCGCGGCTACGCCAATGGGCCAGGAGGCATCAAGGGCATCAATGTCCTTCTC
 V  A  A  T  W  D  R  G  L  M  Y  R  R  G  Y  A  M  G  Q  E  A  K  G  K  G  I  N  V  L  L
 1234567890123456789012345678901234567890123456789012345678901234567890123456789012345678901234567890
       37        38        39        40        41        42        43        44        4

GGACCAGTCGCCGGCCCCCTTGGCCGCATGCCCGAGGGCCGTAACTGGGAAGGCTTCGCTCCGGATCCCGTCCTTACCGGCATCGGC
 G  P  V  A  G  P  L  G  R  M  P  E  G  R  N  W  E  G  F  A  P  D  P  V  L  T  G  I  G
 1234567890123456789012345678901234567890123456789012345678901234567890123456789012345678901234567890
       46        47        48        49        50        51        52        53        5

ATGTCCGAGACGATCAAGGGCATTCAGGATGCTGGCGTCATCGCTTGTGCAAGCACTTTATTGGAAAACGAGCAGGAGCACTTCAGACAG
 M  S  E  T  I  K  G  I  Q  D  A  G  V  I  A  C  A  K  H  F  I  G  N  E  Q  E  H  F  R  Q
 1234567890123456789012345678901234567890123456789012345678901234567890123456789012345678901234567890
       55        56        57        58        59        60        61        62        6

GTGCCAGAAGCCCAGGGATACGGTTACAACATCAGCGAAACCCTCTCCAACATTGACGACAAGACCATGCACGAGCTCTACCTTTGG
 V  P  E  A  Q  G  Y  G  Y  N  I  S  E  T  L  S  S  N  I  D  D  K  T  M  H  E  L  Y  L  W
 1234567890123456789012345678901234567890123456789012345678901234567890123456789012345678901234567890
       64        65        66        67        68        69        70        71        7
```

```
CCGTTTGCCGATGCCGTCCGGGCCGGTCGGCTCTGTCATGTGCTCGTACCAGCAGGTCAACAACTCGTACGCTGCCAGAACTCGAAG
 P   F   A   D   A   V   R   A   G   V   G   S   V   M   C   S   Y   Q   Q   V   N   N   S   Y   A   C   Q   N   S   K
123456789012345678901234567890123456789012345678901234567890123456789012345678901234567890
 2           73          74          75          76          77          78          79          80          8
CTGCTGAACGACCTCCTCAAGAACGAGCTTGGGTTTCAGGGCTTCCAGGAGTTCGTCATGAGCGACAACTGGGCACAGCACACTGGCGCAGCAAGCGCC
 L   L   N   D   L   L   K   N   E   L   G   F   Q   G   F   Q   E   F   V   M   S   D   N   W   A   Q   H   T   G   A   A   S   A
123456789012345678901234567890123456789012345678901234567890123456789012345678901234567890
 1           82          83          84          85          86          87          88          89          9
GTGGCTGGTCTGTCGATATGTCCATGCCGGGCGACACCCAGTTCAACACACTTCTGGGGCGCCAATCTCACCCTCGCCGTCCTC
 V   A   G   L   D   M   S   M   P   G   D   T   Q   F   N   T   Q   F   W   G   A   N   L   T   L   A   V   L
123456789012345678901234567890123456789012345678901234567890123456789012345678901234567890
 0           91          92          93          94          95          96          97          98          9
AACGGCACAGTCCCTGCCGTCTCGACGACATGGCCATGCGCATCATGGCCGCCCTCTTCAAGGTCACCAAGACCACCGACCTGGAA
 N   G   T   V   P   A   V   R   L   D   D   M   A   M   R   I   M   A   A   L   F   K   V   T   K   T   T   D   L   E
123456789012345678901234567890123456789012345678901234567890123456789012345678901234567890
 9           100         101         102         103         104         105         106         107         1
CCGATCAACTTCTCCTTCTGGACCGACGACACTTATGGCCCGATCCACTGGGCCGCCAAGCAGGGCTACCAGGAGATTAATTCCCACGTT
 P   I   N   F   S   F   W   T   D   D   T   Y   G   P   I   H   W   A   A   K   Q   G   Y   Q   E   I   N   S   H   V
123456789012345678901234567890123456789012345678901234567890123456789012345678901234567890
 08          109         110         111         112         113         114         115         116         1
GACGTCCGCGCCGACCACGGCAACCTCATCCGGGAGATTGCCGCCAAGGGTACGTGCTGCTGAAGAATACCGGCTCTCTACCCCTGAAC
 D   V   R   A   D   H   G   N   L   I   R   E   I   A   A   K   G   T   V   L   L   K   N   T   G   S   L   P   L   N
123456789012345678901234567890123456789012345678901234567890123456789012345678901234567890
 17          118         119         120         121         122         123         124         125         1
AAGCCAAAGTTCGTGGCCGTTGGCGAGGATGCTGGGTCTCCAGCCCAACGGCCCCAACGGCCCCGACGACCGCGGCTGTAACGAAGGC
 K   P   K   F   V   A   V   G   E   D   A   G   S   S   P   N   G   P   N   G   C   S   D   R   G   C   N   E   G
123456789012345678901234567890123456789012345678901234567890123456789012345678901234567890
 26          127         128         129         130         131         132         133         134         1
ACGCTCGCCATGGGCTGGGGATCCGGCACAGCCAACTATCCGTACCTCGTTTCCCCCGACGCCGCCCTCCAGGCCCATCCAGGAC
 T   L   A   M   G   W   G   S   G   T   A   N   Y   P   Y   L   V   S   P   D   A   A   L   Q   A   R   A   I   Q   D
123456789012345678901234567890123456789012345678901234567890123456789012345678901234567890
 35          136         137         138         139         140         141         142         143         1
GGCCACGAGGTACGAGAGCGTCCTGTCCAACTACGCCGAGGAAAAGACAAAGGCTCTGGTCTCGCAGGCCAATGCCAACCGCCATCGTCTTC
 G   T   R   Y   E   S   V   L   S   N   Y   A   E   E   K   T   K   A   L   V   S   Q   A   N   A   T   I   V   F
123456789012345678901234567890123456789012345678901234567890123456789012345678901234567890
 44          145         146         147         148         149         150         151         152         1
GTCAATGCCGACTCAGGCGAGGGCTACATCAACGTGGACGGGTAACGAGGGGACCGTAAGAAGAACCTGACTCTCTGGAACAACGGTGATACT
```

FIGURE 1 (continued)

```
  V   N   A   D   S   G   E   G   Y   I   N   V   D   G   N   E   G   D   R   K   N   L   T   L   W   N   N   G   D   T
  123456789012345678901234567890123456789012345678901234567890123456789012345678901234567890
 53                   154                 155                 156                 157                 158                 159                 160                 161
CTGGTCAAGAACGTCTCGAGCTGGTGCAGCAACCATCGTCGTCATCATCGGTTCCTCTGACCGATTGGTACGACAAC
  L   V   K   N   V   S   S   W   C   S   N   T   I   V   V   I   H   S   V   G   P   V   L   T   D   W   Y   D   N
  123456789012345678901234567890123456789012345678901234567890123456789012345678901234567890
 62                   163                 164                 165                 166                 167                 168                 169                 170
CCCAACATCACGGCCATTCTCTGGGCTGTTCCGGGCAACTCCATCACGACGTGCTTTACGGCAAGGTCAACCCC
  P   N   I   T   A   I   L   W   A   G   L   P   G   Q   E   S   G   N   S   I   T   D   V   L   Y   G   K   V   N   P
  123456789012345678901234567890123456789012345678901234567890123456789012345678901234567890
 71                   172                 173                 174                 175                 176                 177                 178                 179
GCCGCCCGCTCGCCCTTCACTTGGGCAAGACCCGCGAAAGCTATGGCCGGACGTCCTGTACAAGCCGAATAATGGCAATGTGCGCCC
  A   A   R   S   P   F   T   W   G   K   T   R   E   S   Y   G   A   D   V   L   Y   K   P   N   N   G   N   G   A   P
  123456789012345678901234567890123456789012345678901234567890123456789012345678901234567890
 80                   181                 182                 183                 184                 185                 186                 187                 188
CAACAGGACTTCACCGAGGGCGTCTTCATCGACTACCGCTACTTCGACAAGGTTGACGATGACTCGGTCATCTACGAGTTCGGCCACGGC
  Q   Q   D   F   T   E   G   V   F   I   D   Y   R   Y   F   D   K   V   D   D   D   S   V   I   Y   E   F   G   H   G
  123456789012345678901234567890123456789012345678901234567890123456789012345678901234567890
 89                   190                 191                 192                 193                 194                 195                 196                 197
CTGAGCTACACCACCTTCGAGTACATCAGCAACATCCGCGTCGTCAAGTCCAACGTCAGCGAGTACCGGCCCACGACGGGCACCGGCCCAG
  L   S   Y   T   T   F   E   Y   I   S   N   I   R   V   V   K   S   N   V   S   E   Y   R   P   T   T   G   T   T   A   Q
  123456789012345678901234567890123456789012345678901234567890123456789012345678901234567890
 98                   199                 200                 201                 202                 203                 204                 205                 206
GCCCCGACGTTTGGCAACTTCTCCACCGACCTCGAGGACTATCTCTTCCCCAAGGACGAGTTCCCCTACATCTACCAGTACATCTACCCG
  A   P   T   F   G   N   F   S   T   D   L   E   D   Y   L   F   P   K   D   E   F   P   Y   I   Y   Q   Y   I   Y   P
  123456789012345678901234567890123456789012345678901234567890123456789012345678901234567890
 07                   208                 209                 210                 211                 212                 213                 214                 215
TACCTCAACACGACCGACCCCCAGCCGCTCCTCCGGTCTCGGAGGGCCTCGGCCGCCAGCGCAGATCCGGCCAAGCTGCCTGTACAACGGCCACCGAT
  Y   L   N   T   T   D   P   R   R   A   S   A   D   P   H   Y   G   Q   T   A   E   E   F   L   P   F   H   A   T   D
  123456789012345678901234567890123456789012345678901234567890123456789012345678901234567890
 16                   217                 218                 219                 220                 221                 222                 223                 224
GACGACCCCCAGCCGCTCCTCCGGTCTCCTCCGGGCGGAAACTCCCCCGGCCAACTCCCCGGCGGGCAACCGCAGCTGTACGACATTGTCTACACAATCACGGCC
  D   D   P   Q   P   L   L   R   S   S   G   N   S   P   G   G   N   R   Q   L   Y   D   I   V   Y   T   I   T   A
  123456789012345678901234567890123456789012345678901234567890123456789012345678901234567890
 25                   226                 227                 228                 229                 230                 231                 232                 233
GACATCACGAATACGGGCTCCGTTGTAGGCGAGGAGGTACCGCAGCTCTACGTCTCCCTCGGCGGGCCCGAGGATCCCAAGGTGCAGCTG
  D   I   T   N   T   G   S   V   V   G   E   E   V   P   Q   L   Y   V   S   L   G   G   P   E   D   P   K   V   Q   L
```

FIGURE 1 (continued)

```
         123456789012345678901234567890123456789012345678901234567890
             235       236       237       238       239       240       241       242
         CGGGACTTTGACAGGATGCGGATCGAAACCCGGAGACGAGGCAGTTCACGGGCCGCCTGACGCGCAGAGATCTGAGCAACTGGGACGTC
           R  D  F  D  R  M  R  I  E  P  G  E  T  R  Q  F  T  G  R  L  T  R  D  L  S  N  W  D  V
         123456789012345678901234567890123456789012345678901234567890123456789012345678901234567890
             243       244       245       246       247       248       249       250       251
         ACGGTGCAGGACTGGGTCATCAGCAGGTATCCCAAGACGGCATATGTTGGGAGGAGCAGCCGGAAGTTGGATCTCAAGATTGAGCTTCCT
           T  V  Q  D  W  V  I  S  R  Y  P  K  T  A  Y  V  G  R  S  S  R  K  L  D  L  K  I  E  L  P
         123456789012345678901234567890
             253       254       255       256       257       258       259       260
         tga
           *
         1234
```

EXPRESSION CONSTRUCTS COMPRISING FUNGAL PROMOTERS

The present application claims priority to U.S. Prov. Patent Appln. Ser. Nos. 61/375,702, 61/375,745, 61/375,753, 61/375,755, and 61/375,760, all of which were filed on Aug. 20, 2010, and are hereby incorporated by reference in their entireties.

FIELD OF THE INVENTION

The present invention provides promoters derived from a filamentous fungus. These promoters have application in the fields of molecular biology, microbiology, fungal genetics and production of biofuels and other products.

BACKGROUND

In many commercial applications using recombinant host cells, strong promoters are required to express commercially useful amounts of desired proteins in the cell. Although numerous promoters are known in the art, only a limited number of promoters from filamentous fungi have been characterized.

SUMMARY OF THE INVENTION

The present invention provides promoters derived from a filamentous fungus. These promoters have application in the fields of molecular biology, microbiology, fungal genetics and production of biofuels and other products.

The present invention provides isolated polynucleotides having promoter activity comprising: (a) a nucleotide sequence set forth in any of SEQ ID NOS:1-40; (b) a subsequence of (a) comprising at least about 75 contiguous nucleotides set forth in any of SEQ ID NOS:1-40; (c) a nucleotide sequence having at least about 90% sequence identity to (a) or (b); and/or (d) a nucleotide sequence that hybridizes to any of SEQ ID NOS:1-40, and/or the complement thereof. Also provided are expression constructs comprising the isolated promoter operably linked to a heterologous DNA sequence encoding a protein. Also provided are expression constructs comprising the isolated promoter operably linked to a heterologous DNA sequence encoding a protein. It is contemplated that any suitable protein will find use in the present invention. In some embodiments, the protein is an enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides isolated polynucleotides having C1 promoter activity comprising: (a) a nucleotide sequence set forth in any of SEQ ID NOS:1-40; (b) a subsequence of (a) comprising at least about 75 contiguous nucleotides set forth in any of SEQ ID NOS:1-40; (c) a nucleotide sequence having at least about 90% sequence identity to (a) or (b); and/or (d) a nucleotide sequence that hybridizes to any of SEQ ID NOS:1-40, and/or the complement thereof. Also provided are expression constructs comprising the isolated promoter operably linked to a heterologous DNA sequence encoding a protein. Also provided are expression constructs comprising the isolated promoter operably linked to a heterologous DNA sequence encoding a protein. It is contemplated that any suitable protein will find use in the present invention. In some embodiments, the protein is an enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

In some embodiments, an expression cassette comprising at least one expression construct comprising at least one of the promoters described herein is provided. In some embodiments, an expression vector is provided. In some additional embodiments, cells comprising the expression cassette are provided. In some embodiments, the cell is a yeast cell or a filamentous fungal cell (e.g., C1 cell).

The present invention also provides processes for producing at least one protein in a host cell by culturing a cell containing the nucleic acid, expression cassette and/or expression vector.

In some embodiments, the present invention provides isolated and/or recombinant polynucleotides having C1 promoter activity comprising: (a) nucleotide sequence set forth in any of SEQ ID NOS:1-40; (b) a subsequence of (a) comprising at least about 75, about 100, about 200, about 300, about 400, or about 500 contiguous nucleotides set forth in any of SEQ ID NOS:1-40; (c) a nucleotide sequence having at least about 90%, about 91%, about 92%, about 93%, about 94%, about 95%, about 96%, about 97%, about 98%, or about 99% sequence identity to (a) or (b); and/or (d) a nucleotide sequence that hybridizes to any of SEQ ID NOS:1-40, and/or the complement thereof.

The present invention provides isolated and/or recombinant polynucleotide with C1 promoter activity comprising: (a) a nucleotide sequence of SEQ ID NO:1, 9, 17, 25 and/or 33; (b) a subsequence of (a) comprising at least about 75 contiguous nucleotides of SEQ ID NO:1, 9, 17, 25 and/or 33; (c) a nucleotide sequence having at least about 90% sequence identity to (a) or (b); and/or (d) a nucleotide sequence that hybridizes to the complement of SEQ ID NO:1, 9, 17, 25 and/or 33.

The present invention also provides isolated and/or recombinant polynucleotide with C1 promoter activity comprising: (a) a nucleotide sequence of SEQ ID NO:1, 9, 17, 25 and/or 33; (b) a subsequence of (a) comprising at least about 75, about 150, about 200, about 300, about 400, about 500, about 600, about 700, about 800, about 900, about 1000, about 1100, about 1200, about 1300, or about 1400 contiguous nucleotides of SEQ ID NO:1, 9, 17, 25 and/or 33; (c) a nucleotide sequence having at least about 90% sequence identity to (a) or (b); and/or (d) a nucleotide sequence that hybridizes to the complement of SEQ ID NO:1, 9, 17, 25 and/or 33.

The present invention also provides isolated and/or recombinant polynucleotides with C1 promoter activity comprising: (a) a nucleotide sequence of SEQ ID NO:1, 9, 17, 25 and/or 33; (b) a subsequence of (a) comprising at least about 75 contiguous nucleotides of SEQ ID NO:1, 9, 17, 25 and/or 33; (c) a nucleotide sequence having at least about 95% sequence identity to (a) or (b); and/or (d) a nucleotide sequence that hybridizes to the complement of SEQ ID NO:1, 9, 17, 25 and/or 33.

The present invention also provides isolated and/or recombinant polynucleotides with C1 promoter activity comprising: (a) a nucleotide sequence of SEQ ID NO:2-8, 10-16, 18-24, 26-32, and/or 34-40; (b) a subsequence of (a) comprising at least about 75 contiguous nucleotides of SEQ ID NO:2-8, 10-16, 18-24, 26-32, and/or 34-40; (c) a nucleotide sequence having at least about 90% sequence identity to (a) or (b), and/or (d) a nucleotide sequence that hybridizes to the complement of SEQ ID NO: 2-8, 10-16, 18-24, 26-32, and/or 34-40.

In some embodiments, the present invention also provides isolated and/or recombinant polynucleotides with C1 promoter activity comprising: (a) a nucleotide sequence of SEQ ID NO:2-8, 10-16, 18-24, 26-32, and/or 34-40; (b) a subsequence of (a) comprising at least about 75, about 150, about 200, about 300, about 400, or about 500 contiguous nucleotides of SEQ ID NO:2-8, 10-16, 18-24, 26-32, and/or 34-40; (c) a nucleotide sequence having at least about 90% sequence identity to (a) or (b), and/or (d) a nucleotide sequence that hybridizes to the complement of SEQ ID NO: 2-8, 10-16, 18-24, 26-32, and/or 34-40.

In some embodiments, the present invention also provides isolated and/or recombinant polynucleotides with C1 promoter activity comprising: (a) a nucleotide sequence of SEQ ID NO:2-8, 10-16, 18-24, 26-32, and/or 34-40; (b) a subsequence of (a) comprising at least about 75 contiguous nucleotides of SEQ ID NO:2-8, 10-16, 18-24, 26-32, and/or 34-40; (c) a nucleotide sequence having at least about 90%, about 91%, about 92%, about 93%, about 94%, about 95%, about 96%, about 97%, about 98%, or about 99% sequence identity to (a) or (b), and/or (d) a nucleotide sequence that hybridizes to the complement of SEQ ID NO: 2-8, 10-16, 18-24, 26-32, and/or 34-40.

In some embodiments, the present invention also provides isolated and/or recombinant polynucleotides with C1 promoter activity comprising: (a) a nucleotide sequence set forth in any of SEQ ID NO:3, 11, 19, 27, and/or 35; (b) a subsequence of (a) comprising at least about 75, about 100, about 200, about 300, about 400, about 500, or about 600 contiguous nucleotides set forth in any of SEQ ID NO:3, 11, 19, 27, and/or 35; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:3, 11, 19, 27, and/or 35, and/or a complement thereof.

The present invention also provides isolated and/or recombinant polynucleotides having C1 promoter activity comprising: (a) a nucleotide sequence set forth in any of SEQ ID NO:4, 12, 20, 28, and/or 36; (b) a subsequence of (a) comprising at least about 75, about 100, about 200, about 300, about 400, or about 500 contiguous nucleotides set forth in any of SEQ ID NO:4, 12, 20, 28, and/or 36; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:4, 12, 20, 28, and/or 36, and/or a complement thereof.

The present invention also provide isolated and/or recombinant polynucleotides having C1 promoter activity comprising: (a) a nucleotide sequence set forth in any of SEQ ID NO:5, 13, 21, 29, and/or 37; (b) a subsequence of (a) comprising at least about 75, about 100, about 200, about 300, or about 400 contiguous nucleotides set forth in any of SEQ ID NO:5, 13, 21, 29, and/or 37; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:5, 13, 21, 29, and/or 37, and/or a complement thereof.

The present invention also provides isolated and/or recombinant polynucleotides having C1 promoter activity comprising: (a) a nucleotide sequence set forth in any of SEQ ID NO:6, 14, 22, 30, and/or 38; (b) a subsequence of (a) comprising at least about 75, about 100, about 200, about 300 or about 400 contiguous nucleotides set forth in any of SEQ ID NO:6, 14, 22, 30, and/or 38; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:6, 14, 22, 30, and/or 38, and/or a complement thereof.

The present invention also provides isolated and/or recombinant polynucleotides having C1 promoter activity comprising: (a) a nucleotide sequence set forth in any of SEQ ID NO:7, 15, 23, 31, and/or 39; (b) a subsequence of (a) comprising at least about 75, about 100, about 200, or about 300 contiguous nucleotides set forth in any of SEQ ID NO:7, 15, 23, 31, and/or 39; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:7, 15, 23, 31, and/or 39, and/or a complement thereof.

The present invention also provides isolated and/or recombinant polynucleotides having C1 promoter activity comprising: (a) a nucleotide sequence of set forth in any of SEQ ID NO:8, 16, 24, 32, and/or 40; (b) a subsequence of (a) comprising at least about 75, about 100, or about 200 contiguous nucleotides set forth in any of SEQ ID NO:8, 16, 24, 32, and/or 40; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:8, 16, 24, 32, and/or 40, and/or a complement thereof.

The present invention also provides expression constructs comprising at least one isolated polynucleotide having C1 promoter activity comprising: polynucleotides having C1 promoter activity comprising: (a) a nucleotide sequence set forth in any of SEQ ID NOS:1-40; (b) a subsequence of (a) comprising at least about 75 contiguous nucleotides set forth in any of SEQ ID NOS:1-40; (c) a nucleotide sequence having at least about 90% sequence identity to (a) or (b); and/or (d) a nucleotide sequence that hybridizes to any of SEQ ID NOS: 1-40, and/or the complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) nucleotide sequence set forth in any of SEQ ID NOS:1-40; (b) a subsequence of (a) comprising at least about 75, about 100, about 200, about 300, about 400, or about 500 contiguous nucleotides set forth in any of SEQ ID NOS:1-40; (c) a nucleotide sequence having at least about 90%, about 91%, about 92%, about 93%, about 94%, about 95%, about 96%, about 97%, about 98%, or about 99% sequence identity to (a) or (b); and/or (d) a nucleotide sequence that hybridizes to any of SEQ ID NOS:1-40, and/or the complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence set forth in any of SEQ ID NO:1, 9, 17, 25, and/or 33; (b) a subsequence of (a) comprising at least about 75, about 100, about 200, about 300, about 400, about 500, about 600, about 700, about 800, about 900, about 1000, about 1100, about 1200, about 1300, or about 1400 contiguous nucleotides set forth in any of SEQ ID NO:1, 9, 17, 25, or 33; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:1, 9, 17, 25, and/or 33, and/or a complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) nucleotide sequence set forth in any of SEQ ID NO:2, 10, 18, 26, and/or 34; (b) a subsequence of (a) comprising at least about 75, about 100, about 200, about 300, about 400, about 500, about 600, about 700, about 800, or about 900 contiguous nucleotides set forth in any of SEQ ID NO:2, 10, 18, 26, and/or 34; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:2, 10, 18, 26, and/or 34, and/or a complement thereof. In some embodiments, the expression constructs comprise the isolated promoter operably linked to a heterologous DNA sequence encoding a protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence set forth in any of SEQ ID NO:3, 11, 19, 27, and/or 35; (b) a subsequence of (a) comprising at least about 75, about 100, about 200, about 300, about 400, about 500 or about 600 contiguous nucleotides set forth in any of SEQ ID NO:3, 11, 19, 27, and/or 35; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:3, 11, 19, 27, and/or 35, and/or a complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence set forth in any of SEQ ID NO:4, 12, 20, 28, and/or 36; (b) a subsequence of (a) comprising at least about 75, about 100, about 200, about 300, about 400, or about 500 contiguous nucleotides set forth in any of SEQ ID NO:4, 12, 20, 28, and/or 36; (c) a nucleotide sequence having at least about 90%, about 91%, about 92%, about 93%, about 94%, about 95%, about 96%, about 97%, about 98%, or about 99% sequence identity to (a) or (b); or (d) a nucleotide sequence that hybridizes to any of SEQ ID NO:4, 12, 20, 28, and/or 36, and/or a complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence set forth in any of SEQ ID NO:5, 13, 21, 29, and/or 37; (b) a subsequence of (a) comprising at least about 75, about 100, about 200, about 300, or about 400 contiguous nucleotides set forth in any of SEQ ID NO:5, 13, 21, 29, and/or 37; (c) a nucleotide sequence having at least about 90%, about 91%, about 93%, about 94%, about 95%, about 96%, about 97%, about 98%, or about 99% sequence identity to (a) or (b); or (d) a nucleotide sequence that hybridizes to any of SEQ ID NO:5, 13, 21, 29, and/or 37, and/or a complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence set forth in any of SEQ ID NO:6, 14, 22, 30, and/or 38; (b) a subsequence of (a) comprising at least about 75, about 100, about 200, about 300, or about 400 contiguous nucleotides set forth in any of SEQ ID NO:6, 14, 22, 30, and/or 38; (c) a nucleotide sequence having at least about 90%, about 91%, about 93%, about 94%, about 95%, about 96%, about 97%, about 98%, or about 99% sequence identity to (a) or (b); or (d) a nucleotide sequence that hybridizes to any of SEQ ID NO:6, 14, 22, 30, and/or 38, and/or a complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence set forth in any of SEQ ID NO:7, 15, 23, 31, and/or 39; (b) a subsequence of (a) comprising at least about 75, about 100, about 200, or about 300 contiguous nucleotides set forth in any of SEQ ID NO:7, 15, 23, 31, and/or 39; (c) a nucleotide sequence having at least about 90%, about 91%, about 93%, about 94%, about 95%, about 96%, about 97%, about 98%, or about 99% sequence identity to (a) or (b); or (d) a nucleotide sequence that hybridizes to any of SEQ ID NO:7, 15, 23, 31, and/or 39, and/or a complement thereof. In some embodiments, the expression constructs comprise at least one isolated promoter operably linked to a heterologous DNA sequence encoding a protein. It is contemplated that any suitable protein will find use in the present invention. In some embodiments, the protein is an enzyme. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (a) a nucleotide sequence of set forth in any of SEQ ID NO:8, 16, 24, 32, and/or 40; (b) a subsequence of (a) comprising at least about 75, about 100, or about 200 contiguous nucleotides set forth in any of SEQ ID NO:8, 16, 24, 32, and/or 40; (c) a nucleotide sequence having at least about 90%, about 91%, about 93%, about 94%, about 95%, about 96%, about 97%, about 98%, or about 99% sequence identity to (a) or (b); or (d) a nucleotide sequence that hybridizes to any of SEQ ID NO:8, 16, 24, 32, and/or 40, and/or a complement thereof. In some embodiments, the expression constructs comprise at least one isolated promoter operably linked to at least one heterologous DNA sequence encoding at least one protein. It is contemplated that any suitable protein will find use in the present invention. In some embodiments, the protein is an enzyme. In some embodiments, the protein comprises at least one recombinant protein. In some embodiments, the at least one recombinant protein is at least one recombinant enzyme. In some embodiments, the enzyme is a cellulase (e.g., an endoglucanase, a cellobiohydrolase or a β-glucosidase), a glucoamylase, a protease, an alpha amylase, a hemicellulase, a xylanase, an esterase, a cutinase, a phytase, a lipase, an oxidoreductase, a laccase, an isomerase, a pullulanase, a phenol oxidizing enzyme, a mannase, a catalase, a glucose oxidase, a transferase or a lyase. In some embodiments, the protein comprises a signal peptide fused to a secreted protein sequence, which may be signal peptide not associated with the secreted protein in nature.

The present invention also provides expression constructs comprising at least one isolated polynucleotide having C1 promoter activity comprising: (i) a subsequence comprising at least about 100 contiguous nucleotides of SEQ ID NOS:3, 11, 19, 27, and/or 35; or (ii) a nucleotide sequence having at least about 90%, about 91%, about 92%, about 93%, about 94%, about 95%, about 96%, about 97%, about 98%, or about 99% sequence identity to (i).

The present invention also provides expression constructs comprising at least one isolated polynucleotide having C1 promoter activity comprising: (i) a subsequence comprising at least about 150 contiguous nucleotides of SEQ ID NO:3, 11, 19, 27, and/or 35; or (ii) a nucleotide sequence having at least about 90%, about 91%, about 92%, about 93%, about 94%, about 95%, about 96%, about 97%, about 98%, or about 99% sequence identity to (i).

The present invention also provides expression constructs comprising at least one isolated polynucleotide having C1 promoter activity comprising: (i) a subsequence comprising at least about 300 contiguous nucleotides of SEQ ID NO:3, 11, 19, 27, and/or 35; or (ii) a nucleotide sequence having at least about 90%, about 91%, about 92%, about 93%, about 94%, about 95%, about 96%, about 97%, about 98%, or about 99% sequence identity to (i).

The present invention also provides expression constructs comprising at least one isolated polynucleotide having C1 promoter activity comprising: (i) a subsequence comprising at least about 400 contiguous nucleotides of SEQ ID NO:3, 11, 19, 27, and/or 35; or (ii) a nucleotide sequence having at least about 90%, about 91%, about 92%, about 93%, about 94%, about 95%, about 96%, about 97%, about 98%, or about 99% sequence identity to (i).

The present invention also provides host cells comprising at least one expression construct as provided herein. In some embodiments, the host cell is a yeast or filamentous fungal cell. In some embodiments, the host cell is *Myceliophthora thermophila*. In some embodiments, the expression construct is integrated into the genome of said host cell.

The present invention also provides methods for producing a protein in a host cell, comprising culturing the host cell comprising at least one expression construct, under conditions such that the protein is produced by the host cell. In some embodiments, the methods further comprise the step of isolating the protein produced by the host cell.

BRIEF DESCRIPTION OF THE FIGURES

FIG. 1 shows the sequence of the C1 bgl1 gene (SEQ ID NO:41) and β-glucosidase protein (SEQ ID NO:42) from copending application No. 601/247379 (filed Sep. 30, 2009) which is incorporated herein by reference for all purposes.

DESCRIPTION OF THE INVENTION

Figure 2:
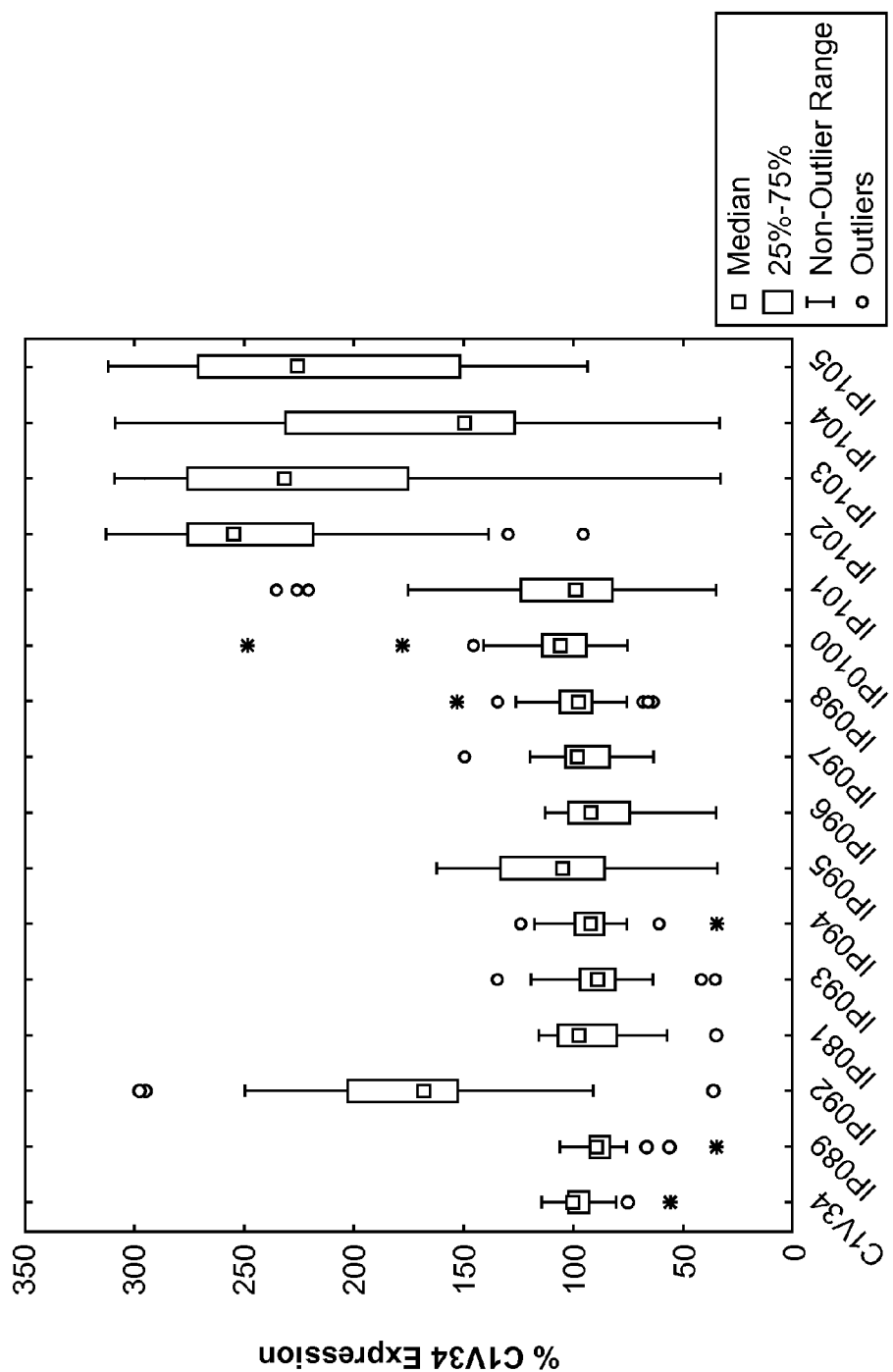
FIG. 2 is a bar graph showing the effect of different promoters on the level of expression of a C1 cellulase in a C1 strain (UV18#100.f [Δ]pyr5 [Δ]alp1).

The present invention provides promoters derived from a filamentous fungus. These promoters have application in the fields of molecular biology, microbiology, fungal genetics and production of biofuels and other products.

Promoters from the fungal strain C1 have been identified and characterized, and can be used for the expression of heterologous genes and recombinant protein production in host cells and particularly in fungal host cells. DNA constructs, vectors, cells and methods for protein production are also provided herein.

Definitions and Methods

Unless defined otherwise, technical and scientific terms used herein generally have the same meaning as commonly understood by one of ordinary skill in the art to which this invention belongs. All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Unless indicated otherwise, the techniques and procedures described or referred to herein are generally performed according to conventional methods well known in the art. Texts disclosing general methods and techniques in the field of recombinant genetics are widely available and known to those in the art. DNA sequences can be obtained by cloning, or by chemical synthesis.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the term "promoter" refers to a polynucleotide sequence, particularly a DNA sequence, that initiates and facilitates the transcription of a target gene sequence in the presence of RNA polymerase and transcription regulators. In some embodiments, promoters include DNA sequence elements that ensure proper binding and activation of RNA polymerase, influence where transcription will start, affect the level of transcription and, in the case of inducible promoters, regulate transcription in response to environmental conditions. Promoters are located 5' to the transcribed gene and, as used herein, include the sequence 5' from the translation start codon (i.e., in some embodiments, including the 5' untranslated region of the mRNA, typically comprising 100-200 bp). Most often, the core promoter sequences lie within 1-2 kb of the translation start site, more often within 1 kbp and often within 750 bp, 500 by or 200 by of the translation start site. By convention, the promoter sequence is usually provided as the sequence on the coding strand of the gene it controls.

As used herein, the term "inducible promoter" refers to a promoter that initiates transcription only when the host cell comprising the inducible promoter is exposed to particular environmental factors (e.g., temperature or light responsive promoters), chemical factors (e.g., promoters induced by small molecules, such as IPTG or tetracycline), metabolic factors (e.g., promoters induced or repressed by glucose or metabolites; promoters active during exponential growth phase), physical factors and the like.

As used herein, the term "constitutive promoter" refers to a promoter that drives transcription at about the same level under a variety of environmental or growth conditions. In some embodiments, the term "constitutive promoter" refers to a promoter that is glucose-independent (i.e., is not induced by or repressed by glucose levels). Glucose independent regulation can be determined as described in the Examples below. In additional embodiments, the term "constitutive promoter" refers to a promoter that is not growth dependent (i.e., drives transcription during both exponential and non-exponential growth phases).

As used herein, the term "promoter activity" refers to the level of expression or activity of the gene and/or polypeptide operably linked to the promoter of interest. Any suitable method for determining/measuring promoter activity finds use in the present invention. For example, promoter activity can be measured by estimating the levels of expression of transcript, production of protein, or protein activity by one of ordinary skill in the art by well known methods, including but not limited to quantitative real-time PCR (qRT-PCR), Northern blot hybridization, SDS-PAGE analysis, and/or enzyme activity assays.

As used herein, the term "C1C promoter" refers to any of the promoters encompassed by the invention, including but not limited to promoters comprising nucleic acid sequences provided in SEQ ID NO:1, SEQ ID NO:2, SEQ ID NO:3, SEQ ID NO:9, SEQ ID NO:10, SEQ ID NO:11, SEQ ID NO:17, SEQ ID NO:18, SEQ ID NO:19, SEQ ID NO:25, SEQ ID NO:26, SEQ ID NO:27, SEQ ID NO:33, SEQ ID NO:34, and/or SEQ ID NO:35, and subsequences (e.g., SEQ ID NOS:4-8, 12-16, 20-24, 28-32, and 36-40) and variants thereof. The term "C1a promoter" refers to the various promoters comprising a nucleic acid sequence of SEQ ID NOS:1, 2 and/or 3, and subsequences (e.g., SEQ ID NOS:4-8) and variants thereof. The term "C1Cb promoter" refers to the various promoters comprising a nucleic acid sequence of SEQ ID NOS:9,10, and/or 11, and subsequences (e.g., SEQ ID NOS:12-16) and variants thereof. The term "C1Cc promoter" refers to the various promoters comprising a nucleic acid sequence of SEQ ID NOS:17, 18 and/or 19, and subsequences (e.g., SEQ ID NOS:20-24) and variants thereof. The term "C1Cd promoter" refers to the various promoters comprising a nucleic acid sequence of SEQ ID NOS:25, 26, and/or 27, and subsequences (e.g., SEQ ID NOS:28-32) and variants thereof. The term "C1Ce promoter" refers to the various promoters comprising a nucleic acid sequence of SEQ ID NOS:33, 34, and/or 35, and subsequences (e.g., SEQ ID NOS:36-40) and variants thereof.

As used herein, the term "variant" used in reference to a promoter means a C1C promoter that comprises one or more modifications such as substitutions, additions or deletions of one or more nucleotides relative to a wild-type sequence or another "starting" or "parent sequence." In some embodiments, the term refers to a C1Ca promoter with one or more modifications such as substitutions, additions or deletions of one or more nucleotides relative to a wild-type sequence. In other embodiments this refers to C1Cb, C1Cc, C1Cd and/or C1Ce promoters with one or more modifications relative to the wild-type sequence. Such variants retain the ability to drive expression of a protein-encoding polynucleotide to which the promoter is operably linked.

As used herein, the terms "reference promoter" and "reference sequence" when used in the context of promoters, refer to a promoter to which a variant promoter of the present invention is compared in order to determine the presence of an improved property in the variant promoter being evaluated (e.g., expression). In some embodiments, a reference promoter is a wild-type promoter (e.g., SEQ ID NOS:1, 9, 17, 25, and/or 33). In some embodiments, a reference promoter is another variant promoter (e.g., a variant of a wild-type promoter, of the present invention).

As used herein, the term "reference enzyme" refers to an enzyme to which a variant enzyme of the present invention is compared in order to determine the presence of an improved property in the variant enzyme being evaluated, including but not limited to improved thermoactivity, improved thermostability, or improved stability. In some embodiments, a reference enzyme is a wild-type enzyme, while in some other embodiments, a reference enzyme is another variant enzyme.

As used herein, the term "wild-type promoter sequence" refers a promoter sequence that is found in nature (e.g., any one of SEQ ID NOS:1, 9, 17, 25, and/or 33), as well as functional fragments of such promoter sequences.

As used herein, the terms "modifications" and "mutations" when used in the context of substitutions, deletions, insertions and the like with respect to polynucleotides and polypeptides are used interchangeably herein and refer to changes that are introduced by genetic manipulation to create variants from a wild-type sequence.

As used herein, the term "functional fragment" refers to a promoter that contains a subsequence, usually of at least about 25, about 50, about 75, about 100, about 150, about 200, about 250, about 300, or about 350, or more, contiguous nucleotides relative to a reference sequence such as one of SEQ ID NOS:1-40 that has promoter activity to drive expression of a polynucleotide encoding a protein to which the promoter is operably linked. Functional fragments typically comprise at least about 20%, 25%, 30%, 35%, 40%, 45%, 50%, about 60%, about 70%, about 75%, about 80%, about 85%, about 90%, about 95% or more, of the promoter activity relative to the 1.5 kb promoter sequence of SEQ ID NO:1, SEQ ID NO:9, SEQ ID NO:17, SEQ ID NO:25, and/or SEQ ID NO:33.

In some embodiments, a variant or functional fragment of a wild-type promoter set forth in any of SEQ ID NOS:1-40, is evaluated for promoter activity in *M. thermophila* (e.g., in a suitable medium comprising complex sources of nitrogen, salts, and carbon), and assessing the level of at least one protein or RNA transcript that is produced from an expression construct comprising the variant promoter operably linked to a polynucleotide sequence encoding at least one protein. In some embodiments, a variant or functional fragment of a promoter is considered to have promoter activity if the promoter is able to produce at least about 25%, about 50%, about 60%, about 70%, about 80%, about 90%, or about 95% or greater, of the protein or RNA produced using a promoter having the sequence of SEQ ID NO:1, 9, 17, 25, and/or 33, when operably linked to a polynucleotide encoding a protein, as compared to a wild-type promoter under the same expression and testing conditions.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. A recombinant cell contains a recombinant polynucleotide or polypeptide. Thus, the term "recombinant" when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

As used herein, the term "recombinant nucleic acid", or equivalently, "recombinant polynucleotide", is one that is inserted into a heterologous location such that it is not associated with nucleotide sequences that normally flank the nucleic acid as it is found in nature (e.g., a nucleic acid inserted into a vector). Likewise, a nucleic acid sequence that does not appear in nature, for example a variant of a naturally occurring gene, is recombinant Thus, in the context of the present invention, an example of a recombinant nucleic acid includes a protein-encoding DNA sequence that is operably linked to a promoter of the present invention.

As used herein, the terms "reporter," "reporter protein," and "reporter sequence" refer to any polypeptide gene expression product that is encoded by a heterologous gene operably linked to a promoter set forth herein.

As used herein, a "signal sequence" is a DNA sequence that encodes a signal peptide. A signal peptide directs the polypeptide with which is associated through a secretory pathway of a cell in which it is synthesized. In some embodiments, the signal peptide is removed during transit through the secretory pathway.

As used herein, the term "vector," refers to a recombinant nucleic acid designed to carry a coding sequence of interest to be introduced into a host cell. In the present invention, vectors comprise at least one promoter sequence and at least one heterologous polynucleotide encoding at least one protein of interest to be expressed by the host cell. This term encompasses many different types of vectors, such as cloning vectors, expression vectors, shuttle vectors, plasmids, phage or virus particles, and the like. Vectors include PCR-based, as well as plasmid vectors. Vectors include an origin of replication and usually include a multicloning site and a selectable marker. In some embodiments, expression vectors also include, in addition to a coding sequence of interest, elements that direct the transcription and translation of the coding sequence (e.g., promoters, enhancers, and termination/polyadenylation sequences). In some embodiments, vectors comprising a promoter of the present invention are used as integration vectors, such that the promoter is integrated into the host cell genome.

As used herein, the term "expression cassette" refers to a nucleic acid molecule containing a protein coding sequence and nucleic acid elements that permit transcription of the sequence in a host cell (e.g., promoter and termination/polyadenylation sequences). In some embodiments, expression cassettes are components of expression vectors.

As used herein, the term "expression construct" refers to a polynucleotide comprising a promoter sequence operably linked to a protein encoding sequence. Expression cassettes and expression vectors are examples of "expression constructs." The term also encompasses PCR constructions for targeting DNA to direct integration into the host cell genome at a desired site.

As used herein, the term "expression" of a gene means transcription of the gene. In some embodiments, the term is used in reference to the production of a polypeptide encoded in the gene sequence.

As used herein, the term "overexpress" is intended to encompass increasing the expression of a protein to a level greater than the cell normally produces. It is intended that the term encompass overexpression of endogenous, as well as heterologous proteins.

As used herein, the term "increased expression" means at least about a 1.2-fold increase in the level of transcript for a given gene in the modified organism is observed as compared to the level of transcript for the same gene in the parental organism, when grown under identical or nearly identical conditions of medium composition, temperature, pH, cell density and age of culture. For example, the transcript level of a given gene in the modified organism can be increased by at least about 1.2-, about 1.5-, about 2.0-, about 2.5-, about 3.0-, about 3.5, about 4.0-, about 4.5, about 5.0-, about 5.5-, or 10-fold, or more, relative to the transcript level of the same gene in the parental organism when grown or cultured under essentially the same culture conditions. The modulation of expression of genes also can be measured by one of ordinary skill in the art through analysis of selected mRNA or transcript levels by well-known means, for example, quantitative real-time PCR (qRT-PCR), Northern blot hybridization, or global gene expression profiling using cDNA or oligo array hybridization.

As used herein, the terms "nucleic acid," "nucleotide," and "polynucleotide," refer to deoxyribonucleotides or ribonucleotides and polymers thereof in either single-stranded or double-stranded form. Except were specified or otherwise clear from context, reference to a nucleic acid sequence (e.g., any of SEQ ID NOS:1-40) encompasses a double stranded molecule.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, N.Y.), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

As used herein, the terms "identical" and "percent identity," in the context of describing two or more polynucleotide sequences, refer to two or more sequences that are the same or have a specified percentage of nucleotides that are the same when compared and aligned for maximum correspondence over a comparison window or designated region, as measured using one of the following sequence comparison algorithms or by manual alignment and visual inspection.

For sequence comparison, typically one sequence acts as a "reference sequence," to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of a wild-type promoter sequence (e.g., SEQ ID NOS:1, 9, 17, 25, and/or 33), with its variants, the BLAST and BLAST 2.0 algorithms and the default parameters discussed below may be used.

A "comparison window" as used herein, includes reference to a segment of any one of the number of contiguous positions selected from the group consisting of from 20 to 500, usually about 50 to about 300, also about 50 to 250, and also about 100 to about 200 in which a sequence may be compared to a reference sequence of the same number of contiguous positions after the two sequences are optimally aligned. Methods of alignment of sequences for comparison are well-known in the art. Optimal alignment of sequences for comparison can be conducted using any suitable method known in the art. Indeed, various methods are well-known to those of skill in the art, including manual alignment and visual inspection, as well as other methods, including computerized methods (See e.g., Smith and Waterman, Adv. Appl. Math., 2:482 [1981]; Needleman and Wunsch, J. Mol. Biol., 48:443 [1970]; Pearson and Lipman, Proc. Nat'l. Acad. Sci. USA 85:2444 [1988], and Wisconsin Genetics Software Package, Genetics Computer Group [e.g., GAP, BESTFIT, FASTA, and TFASTA]).

Examples of algorithms that are suitable for determining percent sequence identity and sequence similarity are the BLAST and BLAST 2.0 algorithms (See e.g., Altschul et al., J. Mol. Biol., 215: 403-410 [1990]; and Altschul et al., Nucleic Acids Res. 25: 3389-3402 [1977]). Software for performing BLAST analyses is publicly available at the National Center for Biotechnology Information website. The BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

As used herein, the term "heterologous" refers to a nucleic acid or polypeptide that is cloned and or expressed in a context different from how it is present in nature. The term "heterologous," when used to describe a promoter and an operably linked coding sequence, means that the promoter and the coding sequence are not associated with each other in nature. In some embodiments, a promoter and a heterologous coding sequence are from two different organisms. In some alternative embodiments, a promoter and a heterologous coding sequence are from the same organism, provided the particular promoter does not direct the transcription of the coding sequence in the wild-type organism.

When two elements (e.g., a promoter and a coding sequence), are said to be "operably linked," it is meant that the juxtaposition of the two elements allows them to be in a functionally active relationship. In other words, a promoter is "operably linked" to a coding sequence when the promoter controls the transcription of the coding sequence.

As used herein, the term "gene" refers to a segment of DNA that is transcribed. In some embodiments, it includes regions preceding and following the protein coding region (5' and 3' untranslated sequence), as well as intervening sequences (introns) between individual coding segments (exons).

The terms "polypeptide," "peptide," and "protein" are used interchangeably herein to refer to a polymer of amino acid residues.

As used herein, the term "isolated" refers to a compound, protein, cell, nucleic acid sequence and/or an amino acid sequence that is removed from at least one component with which it is naturally associated.

As used herein, the term "cellulase" refers to any enzyme that is capable of degrading cellulose. Thus, the term encompasses enzymes capable of hydrolyzing cellulose (β-1,4-glucan or β-D-glucosidic linkages) to shorter cellulose chains, oligosaccharides, cellobiose and/or glucose. "Cellulases" are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," or "BG"). These enzymes act in concert to catalyze the hydrolysis of cellulose-containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. (3-glucosidases split the cellobiose into glucose monomers.

As used herein, the terms "endoglucanase" and "EG" refer to a category of cellulases (EC 3.2.1.4) that catalyze the hydrolysis of internal β-1,4 glucosidic bonds of cellulose. The term "EG2" is used in reference to a carbohydrate active enzyme expressed from a nucleic acid sequence coding for a glycohydrolase (GH) Family 5 catalytic domain classified under EC 3.2.1.4 or any protein, polypeptide or catalytically active fragment thereof. In some embodiments, he EG2 may be functionally linked to a carbohydrate binding module (CBM) with a high affinity for crystalline cellulase, such as a Family 1 cellulose binding domain.

As used herein, the terms "cellobiohydrolase" and "CBH" refers to a category of cellulases (EC 3.2.1.91) that hydrolyze glycosidic bonds in cellulose. In some embodiments, the cellobiohydrolase is a "type 2 cellobiohydrolase," which is a cellobiohydrolase belonging to the glycoside hydrolase family 6 (GH6) family of cellulases and which is also commonly called "the Ce16 family." Cellobiohydrolases of the GH6 family are described, for example, in the Carbohydrate Active Enzymes (CAZY) database.

As used herein, the term "β-glucosidase," "cellobiase," or "BGL" refers to a category of cellulases (EC 3.2.1.21) that catalyze the hydrolysis of cellobiose to glucose.

As used herein, the term "glycoside hydrolase 61" or "GH61" refers to a category of cellulases that enhance cellulose hydrolysis when used in conjunction with one or more additional cellulases. The GH61 family of cellulases is described, for example, in the Carbohydrate Active Enzymes (CAZY) database (See e.g., Harris et al., Biochem., 49(15): 3305-16 [2010]).

A "hemicellulase" as used herein, refers to a polypeptide that can catalyze hydrolysis of hemicellulose into small polysaccharides such as oligosaccharides, or monomeric saccharides. Hemicelluloses include xylan, glucuonoxylan, arabinoxylan, glucomannan and xyloglucan. Hemicellulases include, for example, the following: endoxylanases, b-xylosidases, a-L-arabinofuranosidases, a-D-glucuronidases, feruloyl esterases, coumarolyl esterases, a-galactosidases, b-galactosidases, b-mannanases, and b-mannosidases. In some embodiments, the present invention provides enzyme mixtures that comprise EG1b and one or more hemicellulases.

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagensis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

An effective way to generate a large collection of functional variants is to use a random mutation strategy. There are numerous texts available known to those skilled in the art that describe techniques employing chemical mutagenesis, cassette mutagenesis, degenerate oligonucleotides, mutually priming oligonucleotides, linker-scanning mutagenesis, alanine-scanning mutagenesis, error-prone PCR, etc. Indeed, mutagenesis may be performed in accordance with any of the techniques known in the art, including random and site-specific mutagenesis. Directed evolution can be performed with any of the techniques known in the art to screen for production of variants including shuffling. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319, 713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

As used herein, the terms "host cell" and "host strain" refer to suitable hosts for expression vectors comprising DNA provided herein. In some embodiments, the host cells are prokaryotic or eukaryotic cells that have been transformed or transfected with vectors constructed using recombinant DNA techniques as know in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In some embodiments, host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by any suitable genetic engineering techniques and/or classical microbiological techniques (e.g., such as chemical or UV mutagenesis and subsequent selection). Using recombinant technology, nucleic acid molecules can be introduced, deleted, inhibited or modified, in a manner that results in increased yields of EGIb within the organism or in the culture. For example, knockout of Alp1 function results in a cell that is protease deficient. Knockout of pyr5 function results in a cell with a pyrimidine deficient phenotype. In some genetic engineering approaches, homologous recombination is used to induce targeted gene modifications by specifically targeting a gene in vivo to suppress expression of the encoded protein. In an alternative approach, siRNA, antisense, or ribozyme technology finds use in inhibiting gene expression.

As used herein, the term "recombinant host cell" refers to a cell into which at least one heterologous polynucleotide, gene and promoter set forth herein (e.g., an expression vector) has been introduced. The term is also used in reference to cells having at least one heterologous gene or polynucleotide integrated into their genomes.

As used herein, the term "introduced" used in the context of inserting a nucleic acid sequence into a cell, means transformation, transduction, conjugation, transfection, and/or any other suitable method(s) known in the art for inserting nucleic acid sequences into host cells. Any suitable means for the introduction of nucleic acid into host cells find use in the present invention.

As used herein, the terms "transformed" and "transformation" used in reference to a cell refer to a cell that has a non-native nucleic acid sequence integrated into its genome or has an episomal plasmid that is maintained through multiple generations.

As used herein, the term "C1" refers to a *Chrysosporium lucknowense* fungal strain described by Garg (See, Garg, Mycopathol., 30: 3-4 [1966]). "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophilia*. Other C1 strains include organisms deposited under accession numbers ATCC 44006, CBS (Centraalbureau voor Schimmelcultures) 122188, CBS 251.72, CBS 143.77, CBS 272.77, and VKM F-3500D. Exemplary C1 derivatives include modified organisms in which one or more endogenous genes or sequences have been deleted or modified and/or one or more heterologous genes or sequences have been introduced. Derivatives include UV18#100f Δalp1, UV 18#100f Δpyr5 Δalp1, UV 18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO2008073914, incorporated herein by reference.

Methods for recombinant expression of proteins in fungi and other organisms are well known in the art, and a number of suitable expression vectors are available or can be constructed using routine methods. Protocols for cloning and expression in fungal hosts and other organisms are well known in the art (See e.g., Zhu et al., Plasmid 6:128-33 [2009]). Standard references for techniques and protocols are widely available and known to those in the art (See e.g., U.S. Pat. Nos. 6,015,707, 5,811,381 and 6,573,086; US Pat. Pub. Nos. US 2003/0187243, US 2007/0238155, US 2008/0194005, US 2009/0099079; WO 2008/073914 and WO 98/15633, each of which is incorporated by reference herein for all purposes).

As used herein, the terms "culturing" and "cultivating" refer to growing a population of microbial cells (e.g., host cells and/or recombinant host cells) under suitable conditions in a liquid or solid medium. In some embodiments, culturing refers to fermentative bioconversion of a carbon substrate to an end-product. Suitable conditions for culturing and producing cells are well-known in the art. Any suitable methods and compositions for culturing find use in the present invention, including defined and undefined media, as well as rich and minimal media, as known in the art and are desired for the particular use of the present invention.

In some embodiments, the recombinant microorganisms (i.e., recombinant host cells) comprising a promoter of the present invention are grown under batch or continuous fermentations conditions. "Classical batch fermentation" is a closed system, wherein the compositions of the medium is set at the beginning of the fermentation and is not subject to artificial alternations during the fermentation. A variation of the batch system is a "fed-batch fermentation" which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. "Continuous fermentation" is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology. In some embodiments, fermentations are carried out a temperature of about 10° C. to about 60° C., about 15° C. to about 50° C., about 20° C. to about 45° C., about 20° C. to about 40° C., about 20° C. to about 35° C., or about 25° C. to about 45° C. In some embodiments, the fermentation is carried out at a temperature of about 28° C. and/or about 30° C. It will be understood that, in certain embodiments where thermostable host cells are used, fermentations are often carried out at higher temperatures. In some embodiments, the fermentation is carried out for a time period of about 8 hours to about 240 hours, about 8 hours to about 165 hours, about 8 hours to 145 hours, about 16 hours to about 120 hours, or about 24 hours to about 72 hours. In some embodiments, the fermentation will be carried out at a pH of about 3 to about 8, about 4.5 to about 7.5, about 5 to about 7, or about 5.5 to about 6.5. The temperature, time period, pH and other factors will vary depending upon the desired protein production system, and are well-known to those of skill in the art.

As used herein, the terms "biomass," "biomass substrate," "cellulosic biomass," "cellulosic feedstock," and "cellulosic substrate" refer to materials that contain cellulose. Biomass can be derived from any suitable material, including but not limited to plants, animals, or microorganisms (e.g., agricultural, industrial, and forestry residues, industrial and municipal wastes, and terrestrial and aquatic crops grown for energy purposes). Particular examples of cellulosic substrates include, but are not limited to, wood, wood pulp, paper pulp, corn fiber, corn grain, corn cobs, crop residues such as corn husks, corn stover, grasses, wheat, wheat straw, barley, barley straw, hay, rice straw, switchgrass, waste paper, paper and pulp processing waste, woody or herbaceous plants, fruit or vegetable pulp, distillers grain, rice hulls, cotton, hemp, flax, sisal, sugar cane bagasse, sorghum, soy, components obtained from milling of grains, trees, branches, roots, leaves, wood chips, sawdust, shrubs and bushes, vegetables, fruits, and flowers and mixtures thereof. In some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis.

As used herein, the term "saccharification" refers to the process in which substrates (e.g., cellulosic biomass) are broken down via the action of cellulases to produce fermentable sugars (e.g. monosaccharides such as but not limited to glucose).

As used herein, the term "fermentable sugars" refers to simple sugars (e.g., monosaccharides, disaccharides and short oligosaccharides), including but not limited to glucose, xylose, galactose, arabinose, mannose and sucrose. Indeed, a fermentable sugar is any sugar that a microorganism can utilize or ferment.

As used herein, the term "fermentation" is used broadly to refer to the cultivation of a microorganism or a culture of microorganisms that use simple sugars, such as fermentable sugars, as an energy source to obtain a desired product.

As used herein, the term "lignocellulose biomass" refers to any plant biomass comprising cellulose and hemicellulose, bound to lignin.

As used herein, the term "lignocellulosic feedstock" refers to any type of plant biomass such as, but not limited to cultivated crops (e.g., grasses, including C4 grasses, such as switch grass, cord grass, rye grass, miscanthus, reed canary grass, or any combination thereof), sugar processing residues, for example, but not limited to, baggase (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the lignocellulosic feedstock comprises cellulosic waste material and/or forestry waste materials, including but not limited to, paper and pulp processing waste, newsprint, cardboard and the like. The biomass may also comprise transgenic plants that express ligninase and/or cellulase enzymes (US 2008/0104724 A1). In some embodiments, the lignocellulosic feedstock comprises one species of fiber, while in some alternative embodiments, the lignocellulosic feedstock comprises a mixture of fibers that originate from different lignocellulosic feedstocks. In some other embodiments, the lignocellulosic feedstock comprises fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic materal comprises less than about 19%, less than about 18%, less than about 17%, less than about 16%, less than about 15%, less than about 14%, less than about 13%, less than about 12%, less than about 11%, less than about 10%, less than about 9%, less than about 8%,less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size reduction is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction. The biomass may optionally be pretreated to increase the susceptibility of cellulose to hydrolysis by chemical, physical and biological pretreatments (such as steam explosion, pulping, grinding, acid hydrolysis, solvent exposure, and the like, as well as combinations thereof).

C1C Promoters of the Invention

Promoter regions from the filamentous fungus designated C1 were identified and are set forth in SEQ ID NOS: 1, 9, 17, 25 and 33. These promoter sequences, designated C1Ca (SEQ ID NO:1), C1Cb (SEQ ID NO:9), C1Cc (SEQ ID NO:17), C1Cd (SEQ ID NO:25) and C1Ce (SEQ ID NO:33) are strong drivers of expression in C1, and function in a glucose-independent fashion. In some embodiments, the C1Ca, C1Cb, C1Cc, C1Cd and/or C1Ce promoter sequences are operably linked to at least one sequence encoding a heterologous protein, such that the heterologous protein is expressed by a host cell.

In some embodiments, the C1Ca promoter of the invention comprises the 1.5 kb sequence set forth in SEQ ID NO:1. In some embodiments, the C1Ca promoter comprises a subsequence of SEQ ID NO:1, or a variant thereof, as discussed below. In some embodiments, the C1Ca promoter of the invention comprises SEQ ID NO:2, which is the 3' (3-prime) 1 kb of SEQ ID NO:1 (i.e., comprising bases 501-1500 of SEQ ID NO:1). In some embodiments the C1Ca promoter of the invention comprises SEQ ID NO:3, which is the 3' (3-prime) 0.7 kb of SEQ ID NO:1 (i.e., comprising bases 801-1500 of SEQ ID NO:1). The sequences of SEQ ID NOS: 1-3 are provided below.

(SEQ ID NO: 1)
CTTGGGTAATGTAATCCGTCCAGCACATGTCTTGACATGCTTGATGTATGTACTCTATATATT
GAGTACAGTACCTGTCTTGAAGAGCAGTACAGTATACTCTCTGGATGGACTTCGGTGCTTGG
ACGGGAATAATAACTTAGGGTTTGCGCTAAGGTAGACTAGCAGCCAATGAAATCGGCTCAG
TGGCACGAGATACTTTAAAGTGTACGGAGTACTCCGTACGGAACACAGACTCAACAAATTG
CCATGACCATGCAGCTCTCTCTCGCAGCGAGATGAGAGACCCACATAGCATTCCAACCATGT
GAGGAAGTCTATTAGTACGGCTTATGAGTGTACTCCGGACCACTCTAGTTAGTTGTATGCAC
GATCTGTCGAAGAGATCGGTGGTAACTCGCCAGCATGGGCATACCATTTCAAACCAAGATTT
TTATGCGAGCATCAAACTCCACAACTCAGCGTCCGCAGCAGGCATCGGAGAGTTGGCACCCT
CAGCCCTTTTACACTAGAACTAGATTTCTGCAAAAGCTCTTGTGCAAGGCTGCATACAGATA
CACTAGAGTAAGGTGCTTAGCTAATATACTAAAGCGTATTAGTCCCAATCCCATGCAAGCTG
CGAGAGGTCGCAATTTCCCGACTCGGCGCCGCATGCGCTAGTGTGGACTGGGAATCGCGGCC
GAGCGCCTGCCGTAGCTCTTCGCCGCTTGAGAAGGAGACGTGAAGCAGCTGGAACAAACCC
TTTGGAACACCGGGCAGCTTAAAGTTGGCCAAGTAGGAGTTGAGCAACGACGAGGTTCCCG
TGTAGATTACATTGTTAATGTTGGTACTATTGTGCCACAAATAGGCCGCCGTTCCGAGCGAC
AAGAGAGCTATCGAGACCCATCGAACCTCAAATTCCAAGACCGGGACCCCGGCCAGCGTTC
CTTGTCTAGCCCTGGTCGCCCAGAGCTTCCGCCACGCCGCTTCCCCATTGCAACACTGATCTG
GGGTGCGCTAACAGGCGATAATTCTTTCTAGGCGTCCTATTGGCGTGACCCGGGAGAGAAGT
CACTCTCCCATGCCCTCATCGCGTTCCTACTACGGAGTACTCCGTAGTAGCTGCCCATTCCAG
GTCGGCTATTTTGGGTCCAGACGTGCCGCTGCCTTCTTCTTCCGCTCTTCCTTCTTCCTTCCCC
CCTTCCCCAGCCGTAGCTCACACCACACATCCGGCCTGACTGGCATTTCTCTGCCATACTAAT
TAACACTATCCCAACTTCTCCACGGTCGTTCATCTTTGGTTTTTCATTCTCAACTAGACTAATT
AATTACCGCATCGGCGCAGCCAATTCACTTAGGCAAGCTTTGGTAAGTCGCCCCTGTCTGCT
TTGCAGAGTTTCCCCGGCCTTTTCTCCTTGTGACAATCCGGTCCCGAATGGGTTTGTTCTCAA
GTGCATTGACTCACCGCCGAAAGTCGTTCATAGCACTCGCTTTAGATATCAAGCATAAATCC
GGTCCACA (SEQ ID NO: 2)
CTTTTACACTAGAACTAGATTTCTGCAAAAGCTCTTGTGCAAGGCTGCATACAGATACACTA
GAGTAAGGTGCTTAGCTAATATACTAAAGCGTATTAGTCCCAATCCCATGCAAGCTGCGAGA
GGTCGCAATTTCCCGACTCGGCGCCGCATGCGCTAGTGTGGACTGGGAATCGCGGCCGAGCG
CCTGCCGTAGCTCTTCGCCGCTTGAGAAGGAGACGTGAAGCAGCTGGAACAAACCCTTTGGA
ACACCGGGCAGCTTAAAGTTGGCCAAGTAGGAGTTGAGCAACGACGAGGTTCCCGTGTAGA
TTACATTGTTAATGTTGGTACTATTGTGCCACAAATAGGCCGCCGTTCCGAGCGACAAGAGA
GCTATCGAGACCCATCGAACCTCAAATTCCAAGACCGGGACCCCGGCCAGCGTTCCTTGTCT
AGCCCTGGTCGCCCAGAGCTTCCGCCACGCCGCTTCCCCATTGCAACACTGATCTGGGGTGC
GCTAACAGGCGATAATTCTTTCTAGGCGTCCTATTGGCGTGACCCGGGAGAGAAGTCACTCT
CCCATGCCCTCATCGCGTTCCTACTACGGAGTACTCCGTAGTAGCTGCCCATTCCAGGTCGGC
TATTTTGGGTCCAGACGTGCCGCTGCCTTCTTCTTCCGCTCTTCCTTCTTCCTTCCCCCCTTCC
CCAGCCGTAGCTCACACCACACATCCGGCCTGACTGGCATTTCTCTGCCATACTAATTAACA
CTATCCCAACTTCTCCACGGTCGTTCATCTTTGGTTTTTCATTCTCAACTAGACTAATTAATTA
CCGCATCGGCGCAGCCAATTCACTTAGGCAAGCTTTGGTAAGTCGCCCCTGTCTGCTTTGCA
GAGTTTCCCCGGCCTTTTCTCCTTGTGACAATCCGGTCCCGAATGGGTTTGTTCTCAAGTGCA

-continued

TTGACTCACCGCCGAAAGTCGTTCATAGCACTCGCTTTAGATATCAAGCATAAATCCGGTCC

ACA (SEQ ID NO: 3)
CCGTGTAGATTACATTGTTAATGTTGGTACTATTGTGCCACAAATAGGCCGCCGTTCCGAGC

GACAAGAGAGCTATCGAGACCCATCGAACCTCAAATTCCAAGACCGGGACCCCGGCCAGCG

TTCCTTGTCTAGCCCTGGTCGCCCAGAGCTTCCGCCACGCCGCTTCCCCATTGCAACACTGAT

CTGGGGTGCGCTAACAGGCGATAATTCTTTCTAGGCGTCCTATTGGCGTGACCCGGGAGAGA

AGTCACTCTCCCATGCCCTCATCGCGTTCCTACTACGGAGTACTCCGTAGTAGCTGCCCATTC

CAGGTCGGCTATTTTGGGTCCAGACGTGCCGCTGCCTTCTTCTTCCGCTCTTCCTTCTTCCTTC

CCCCCTTCCCCAGCCGTAGCTCACACCACACATCCGGCCTGACTGGCATTTCTCTGCCATACT

AATTAACACTATCCCAACTTCTCCACGGTCGTTCATCTTTGGTTTTTCATTCTCAACTAGACT

AATTAATTACCGCATCGGCGCAGCCAATTCACTTAGGCAAGCTTTGGTAAGTCGCCCCTGTC

TGCTTTGCAGAGTTTCCCCGGCCTTTTCTCCTTGTGACAATCCGGTCCCGAATGGGTTTGTTC

TCAAGTGCATTGACTCACCGCCGAAAGTCGTTCATAGCACTCGCTTTAGATATCAAGCATAA

ATCCGGTCCACA

In some embodiments, the C1Ca promoter of the invention comprises a subsequence of SEQ ID NO:1, SEQ ID NO:2, and/or SEQ ID NO:3 that retains promoter activity, referred to herein as a "short" promoter sequence. Subsequences that retain promoter activity are identified using any suitable routine methods. Provided with SEQ ID NO:1, 2, and/or 3, any of a number of different functional deletion mutants of the starting sequence can be readily prepared. In some embodiments, the subsequences retain constitutive promoter activity (e.g., glucose-independent promoter activity).

In some embodiments, constructs with short promoter sequences are prepared using any of a variety of routine molecular biological techniques. For illustration and not limitation, SEQ ID NO:1 may be cloned into an expression vector so that it is 5' to and operably linked to a sequence encoding a reporter protein. One or a series of deletion constructs may be made to produce one or a library of expression vectors with subsequences of SEQ ID NO:1 operably linked to the sequence encoding the reporter protein. Deletions may be made from the 5' end, the 3' end or internally. Methods for making deletions include, for illustration and not limitation, using restriction and ligation to remove a portion of SEQ ID NO:1 from the vector, using exonucleases to trim the end(s) of the parent sequence, randomly fragmenting the parent sequence and preparing a library of clones containing fragments, etc. In some embodiments, PCR techniques find use. The expression vector(s) is then introduced into a host cell and the cell is cultured under conditions in which the protein is produced, with the presence and level of production being indicative of promoter activity. The reporter protein may be one frequently used to assess promoter strength and properties, such as luciferase. An advantage of using "standard" reporters is the ready availability of commercial assays and materials for assessing transcription. Alternatively the reporter may be another protein, such as a fungal protein and/or a protein product for which high expression is desired.

In some embodiments, the C1Ca promoter sequence comprises at least about 1000 contiguous nucleotides of SEQ ID NO:1 or 2; at least about 900 contiguous nucleotides of SEQ ID NO:1 or 2; at least about 800 contiguous nucleotides of SEQ ID NO:1 or 2; at least about 700 contiguous nucleotides of SEQ ID NO:1, 2, or 3; at least about 600 contiguous nucleotides of SEQ ID NO:1, 2, or 3; at least about 500 contiguous nucleotides of SEQ ID NO:1, 2, or 3; at least about 450 contiguous nucleotides of SEQ ID NO:1, 2, or 3; at least about 400 contiguous nucleotides of SEQ ID NO:1, 2, or 3; at least about 350 contiguous nucleotides of SEQ ID NO:1, 2, or 3; at least about 300 contiguous nucleotides of SEQ ID NO:1, 2, or 3; at least about 250 contiguous nucleotides of SEQ ID NO:1, 2, or 3; at least about 200 contiguous nucleotides of SEQ ID NO: 1, 2, or 3; at least about 150 contiguous nucleotides of SEQ ID NO: 1, 2, or 3; at least about 100 contiguous nucleotides of SEQ ID NO: 1, 2, or 3; or at least about 75 contiguous nucleotides of SEQ ID NO: 1, 2, or 3.

In some embodiments, the C1Ca promoter sequence comprises a subsequence of SEQ ID NO:1 comprising about 75 to about 1000 contiguous nucleotides of SEQ ID NO:1 or 2. In some other embodiments, the C1Ca promoter sequence comprises a subsequence of SEQ ID NO:1, 2, or 3 comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides.

In some embodiments, the subsequence comprises at least about 25, at least about 50, at least about 100, at least about 150, or at least about 200 contiguous nucleotides of SEQ ID NO:3. In some further embodiments, the C1Ca promoter sequence comprises at least one of SEQ ID NOS:4-8, as provided herein. SEQ ID NO:4 comprises bases 871-1430 of SEQ ID NO:1 (0.56 kb), while SEQ ID NO:5 comprises bases 941-1430 of SEQ ID NO:1 (0.49 kb), SEQ ID NO:6 comprises bases 1001-1450 of SEQ ID NO:1 (0.45 kb), SEQ ID NO:7 comprises bases 1001-1400 of SEQ ID NO:1 (0.40 kb), and SEQ ID NO:8 comprises bases 1201-1450 of SEQ ID NO:1 (0.25 kb).

(SEQ ID NO: 4)
AGCTATCGAGACCCATCGAACCTCAAATTCCAAGACCGGGACCCCGGCCAGCGTTCCTTGTC

TAGCCCTGGTCGCCCAGAGCTTCCGCCACGCCGCTTCCCCATTGCAACACTGATCTGGGGTG

CGCTAACAGGCGATAATTCTTTCTAGGCGTCCTATTGGCGTGACCCGGGAGAGAAGTCACTC

TCCCATGCCCTCATCGCGTTCCTACTACGGAGTACTCCGTAGTAGCTGCCCATTCCAGGTCGG

CTATTTTGGGTCCAGACGTGCCGCTGCCTTCTTCTTCCGCTCTTCCTTCTTCCTTCCCCCCTTC

CCCAGCCGTAGCTCACACCACACATCCGGCCTGACTGGCATTTCTCTGCCATACTAATTAAC

ACTATCCCAACTTCTCCACGGTCGTTCATCTTTGGTTTTTCATTCTCAACTAGACTAATTAATT

ACCGCATCGGCGCAGCCAATTCACTTAGGCAAGCTTTGGTAAGTCGCCCCTGTCTGCTTTGC

AGAGTTTCCCCGGCCTTTTCTCCTTGTGACAATCCGGTCCCGAATGGGTTTGTTCTCAA (SEQ ID NO: 5)
GTCGCCCAGAGCTTCCGCCACGCCGCTTCCCCATTGCAACACTGATCTGGGGTGCGCTAACA

GGCGATAATTCTTTCTAGGCGTCCTATTGGCGTGACCCGGGAGAGAAGTCACTCTCCCATGC

CCTCATCGCGTTCCTACTACGGAGTACTCCGTAGTAGCTGCCCATTCCAGGTCGGCTATTTTG

GGTCCAGACGTGCCGCTGCCTTCTTCTTCCGCTCTTCCTTCTTCCTTCCCCCCTTCCCCAGCCG

TAGCTCACACCACACATCCGGCCTGACTGGCATTTCTCTGCCATACTAATTAACACTATCCCA

ACTTCTCCACGGTCGTTCATCTTTGGTTTTTCATTCTCAACTAGACTAATTAATTACCGCATCG

GCGCAGCCAATTCACTTAGGCAAGCTTTGGTAAGTCGCCCCTGTCTGCTTTGCAGAGTTTCCC

CGGCCTTTTCTCCTTGTGACAATCCGGTCCCGAATGGGTTTGTTCTCAA (SEQ ID NO: 6)
CGCCGCTTCCCCATTGCAACACTGATCTGGGGTGCGCTAACAGGCGATAATTCTTTCTAGGC

GTCCTATTGGCGTGACCCGGGAGAGAAGTCACTCTCCCATGCCCTCATCGCGTTCCTACTAC

GGAGTACTCCGTAGTAGCTGCCCATTCCAGGTCGGCTATTTTGGGTCCAGACGTGCCGCTGC

CTTCTTCTTCCGCTCTTCCTTCTTCCTTCCCCCCTTCCCCAGCCGTAGCTCACACCACACATCC

GGCCTGACTGGCATTTCTCTGCCATACTAATTAACACTATCCCAACTTCTCCACGGTCGTTCA

TCTTTGGTTTTTCATTCTCAACTAGACTAATTAATTACCGCATCGGCGCAGCCAATTCACTTA

GGCAAGCTTTGGTAAGTCGCCCCTGTCTGCTTTGCAGAGTTTCCCCGGCCTTTTCTCCTTGTG

ACAATCCGGTC (SEQ ID NO: 7)
CAGGCGATAATTCTTTCTAGGCGTCCTATTGGCGTGACCCGGGAGAGAAGTCACTCTCCCAT

GCCCTCATCGCGTTCCTACTACGGAGTACTCCGTAGTAGCTGCCCATTCCAGGTCGGCTATTT

TGGGTCCAGACGTGCCGCTGCCTTCTTCTTCCGCTCTTCCTTCTTCCTTCCCCCCTTCCCCAGC

CGTAGCTCACACCACACATCCGGCCTGACTGGCATTTCTCTGCCATACTAATTAACACTATCC

CAACTTCTCCACGGTCGTTCATCTTTGGTTTTTCATTCTCAACTAGACTAATTAATTACCGCAT

CGGCGCAGCCAATTCACTTAGGCAAGCTTTGGTAAGTCGCCCCTGTCTGCTTTGCAGAGTTTC

CCCGGCCTTTTCTCCTTGTGA (SEQ ID NO: 8)
CTTCCTTCTTCCTTCCCCCCTTCCCCAGCCGTAGCTCACACCACACATCCGGCCTGACTGGCA

TTTCTCTGCCATACTAATTAACACTATCCCAACTTCTCCACGGTCGTTCATCTTTGGTTTTTCA

TTCTCAACTAGACTAATTAATTACCGCATCGGCGCAGCCAATTCACTTAGGCAAGCTTTGGT

AAGTCGCCCCTGTCTGCTTTGCAGAGTTTCCCCGGCCTTTTCTCCTTGTGACAATCCGGTC

In some embodiments, the C1Cb promoter of the present invention comprises SEQ ID NO:9 (1.5 kb). In some embodiments the C1Cb promoter comprises a subsequence of SEQ ID NO:9, or a variant thereof, as provided herein. In some embodiments, the C1Cb promoter of the invention comprises SEQ ID NO:10, which is the 3' (3-prime) 1 kb of SEQ ID NO:9, comprising bases 501-1500 of SEQ ID NO:9. In some embodiments, the C1Cb promoter of the invention comprises SEQ ID NO:11, which is the 3' (3-prime) 0.7 kb of SEQ ID NO:9, comprising bases 801-1500 of SEQ ID NO:9.

```
                                                            (SEQ ID NO: 9)
ACAGGCTTGTTAAAGGAAGTCTTCACGGTCGGCATACAAATCGGCCAAGACGTTGAAGATG

CCATAATACATAATATGTATGTACAATAACCGGGCACATACGGTGCAACTGCTAGTCAGCAA

TTGCGCCTCGCTTTTTGACACAGAGGGCAATGCAGAACGTCGAATCGACCGAGTCAGTTGCT

GTTGGCGTCATGATGGCTCTAGGGTCAGACAGAAGGTCAGAGAAAGCATGCCTTAGCTCGA

AGCCGCTCAGATGTAATTACGCAACGCTCGGCGTTCGAGTTTACGGAGGACGACGGCTACA

AGATGGGGCTGCTTAAAGTTACCTTAAATAGAAAATAGTGCCTGGCTTAAGAGATCATGTCC

GCGGGGCTAGCAAGGATGTCGGGTCTTAACTCGACGGCTCGCCTAGATTTCGTGAAAAGGG

AACTCACTCCCCGACAGGCCCGCAAGTGAATATGTAATTACTCAATGGAAGTTCTCGAAACG

GAGTCCAGAAATGATGTGGTTCTGTGGGAATGCGGCAAGAGGCGACGTTGCCGTGAATGCG

TGAACATTCCCGCCTCTTCTTCTTCTCGTCTTCTTCCTTCTTCTTCTTTCGGGTCGCGGATGGT

TGACGGCCAGCGTGCGCACGGCTGCGTGTTATCGAGCGTCGGTACGTCTAGCCAACATCCCG

TAGACACGACGACCAAGCGTCTTGAGAATGCAACAACGTCTCGGAACCTGGCACGCATCTTC

CGCCGCAGGTCGGCAGACGCCGCCTGGGCAATACCACCCCTGTCCAGGCCCTTTCCCCGCAG

GCAGAGCCGCGCTCTTCCTTTCATGGTTATTCAGGAACGTGGCTTCCGAGATTCTCGCCTGTT

CTCCCCCAGTCAACCTGCCGACCGTAACCCGGTTCCACCACCGCGGACTGTCCGCAAAACCT

GGTTCGCCCGAGATTAATATGCTATTTCCGGACTAAGTGCACAACACACAAGCACCCCTTCC

GCCTCGCGCTCTAGAATCTGCTTTCTAACCCGGTTCTCGGGCCCTTCCCTTTCGCGACGCCTC

CGCTCTCCTTACCAGGCACCATCCGCAATAGGTAAGGTAGCCAACCGTTTTGGAGCGTGATT

CTGCCAAGGACCGCATCCTTGCATTCGCCATCTGGTCAAGGACCCCTCTTTCCCGCTCCATTC

TGGTGGCTCTATCGGGACGGCGTTCCCCATGGCTCTCCAGGAGAGTGATGTGCGAGTCTGGA

GAGCCGGGGTTGGCGTCACGATGCTGCCCACCTAGGGCCGGCCAGCCCGGCACTGCGCTCCC

GTTGATCCGTCTATCCCCGTCAAGAGCACCAGCCCCGGCGCTCGTGAATTTTCGACTTGTTCG

ACTTGCTACAGGTGATAAAGAGGATGCACGCCGCCCTCGATCGGCCTGTGTGGTTTCTCTCC

CTCGTGCCAAACCACTCCCACCTCCCGCCCCGAGATAGTTGCTTGTTTCGCTCCGTGAGAGG

GACACACACCA
                                                            (SEQ ID NO: 10)
AAATGATGTGGTTCTGTGGGAATGCGGCAAGAGGCGACGTTGCCGTGAATGCGTGAACATT

CCCGCCTCTTCTTCTTCTCGTCTTCTTCCTTCTTCTTCTTTCGGGTCGCGGATGGTTGACGGCC

AGCGTGCGCACGGCTGCGTGTTATCGAGCGTCGGTACGTCTAGCCAACATCCCGTAGACACG

ACGACCAAGCGTCTTGAGAATGCAACAACGTCTCGGAACCTGGCACGCATCTTCCGCCGCAG

GTCGGCAGACGCCGCCTGGGCAATACCACCCCTGTCCAGGCCCTTTCCCCGCAGGCAGAGCC

GCGCTCTTCCTTTCATGGTTATTCAGGAACGTGGCTTCCGAGATTCTCGCCTGTTCTCCCCCA

GTCAACCTGCCGACCGTAACCCGGTTCCACCACCGCGGACTGTCCGCAAAACCTGGTTCGCC

CGAGATTAATATGCTATTTCCGGACTAAGTGCACAACACACAAGCACCCCTTCCGCCTCGCG

CTCTAGAATCTGCTTTCTAACCCGGTTCTCGGGCCCTTCCCTTTCGCGACGCCTCCGCTCTCCT

TACCAGGCACCATCCGCAATAGGTAAGGTAGCCAACCGTTTTGGAGCGTGATTCTGCCAAGG

ACCGCATCCTTGCATTCGCCATCTGGTCAAGGACCCCTCTTTCCCGCTCCATTCTGGTGGCTC

TATCGGGACGGCGTTCCCCATGGCTCTCCAGGAGAGTGATGTGCGAGTCTGGAGAGCCGGG

GTTGGCGTCACGATGCTGCCCACCTAGGGCCGGCCAGCCCGGCACTGCGCTCCCGTTGATCC
```

-continued
```
GTCTATCCCCGTCAAGAGCACCAGCCCCGGCGCTCGTGAATTTTCGACTTGTTCGACTTGCTA

CAGGTGATAAAGAGGATGCACGCCGCCCTCGATCGGCCTGTGTGGTTTCTCTCCCTCGTGCC

AAACCACTCCCACCTCCCGCCCCGAGATAGTTGCTTGTTTCGCTCCGTGAGAGGGACACACA

CCA
```

(SEQ ID NO: 11)
```
CAGGCAGAGCCGCGCTCTTCCTTTCATGGTTATTCAGGAACGTGGCTTCCGAGATTCTCGCCT

GTTCTCCCCCAGTCAACCTGCCGACCGTAACCCGGTTCCACCACCGCGGACTGTCCGCAAAA

CCTGGTTCGCCCGAGATTAATATGCTATTTCCGGACTAAGTGCACAACACACAAGCACCCCT

TCCGCCTCGCGCTCTAGAATCTGCTTTCTAACCCGGTTCTCGGGCCCTTCCCTTTCGCGACGC

CTCCGCTCTCCTTACCAGGCACCATCCGCAATAGGTAAGGTAGCCAACCGTTTTGGAGCGTG

ATTCTGCCAAGGACCGCATCCTTGCATTCGCCATCTGGTCAAGGACCCCTCTTTCCCGCTCCA

TTCTGGTGGCTCTATCGGGACGGCGTTCCCCATGGCTCTCCAGGAGAGTGATGTGCGAGTCT

GGAGAGCCGGGGTTGGCGTCACGATGCTGCCCACCTAGGGCCGGCCAGCCCGGCACTGCGC

TCCCGTTGATCCGTCTATCCCCGTCAAGAGCACCAGCCCCGGCGCTCGTGAATTTTCGACTTG

TTCGACTTGCTACAGGTGATAAAGAGGATGCACGCCGCCCTCGATCGGCCTGTGTGGTTTCT

CTCCCTCGTGCCAAACCACTCCCACCTCCCGCCCCGAGATAGTTGCTTGTTTCGCTCCGTGAG

AGGGACACACACCA
```

In some embodiments, the C1Cb promoter of the present invention comprises a subsequence of SEQ ID NO:9, SEQ ID NO:10, and/or SEQ ID NO:11 that retains promoter activity, referred to herein as a "short" promoter sequence. Provided with SEQ ID NO:9, 10, and/or 11, any of a number of different functional deletion mutants of the starting sequence can be readily prepared as described above. In some embodiments, the subsequences retain constitutive promoter activity (e.g., glucose-independent promoter activity).

In some embodiments, the C1Cb promoter sequence comprise at least about 1000 contiguous nucleotides of SEQ ID NO:9 or 10; at least about 900 nucleotides of SEQ ID NO:9 or 10; at least about 800 nucleotides of SEQ ID NO:9 or 10; at least about 700 nucleotides of SEQ ID NO:9, 10, or 11; at least about 600 nucleotides of SEQ ID NO:9, 10, or 11; at least about 500 nucleotides of SEQ ID NO:9, 10, or 11; at least about 450 nucleotides of SEQ ID NO:9, 10, or 11; at least about 400 nucleotides of SEQ ID NO:9, 10, or 11; at least about 350 nucleotides of SEQ ID NO:9, 10, or 11; at least about 300 nucleotides of SEQ ID NO:9, 10, or 11; at least 250 nucleotides of SEQ ID NO:9, 10, or 11; at least about 200 nucleotides of SEQ ID NO:9, 10, or 11; at least about 150 nucleotides of SEQ ID NO:9, 10, or 11; at least about 100 nucleotides of SEQ ID NO:9, 10, or 11; or at least about 75 contiguous nucleotides of SEQ ID NO:9, 10, or 11.

In some embodiments, the C1Cb promoter sequence comprises a subsequence of SEQ ID NO:9, comprising about 75 to about 1000 contiguous nucleotides of SEQ ID NO:9 or 10. In some other embodiments, the C1Cb promoter sequence comprises a subsequence of SEQ ID NO:9, 10, or 11, comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides.

In some embodiments, the subsequence comprises at least about 25, at least about 50, at least about 100, at least about 150 or at least about 200 contiguous nucleotides of SEQ ID NO:11. In some embodiments, the C1Cb promoter sequence comprises at least one of SEQ ID NOs:12-16, as provided below. SEQ ID NO:12 comprises bases 871-1430 of SEQ ID NO:9 (0.56 kb), while SEQ ID NO:13 comprises bases 941-1430 of SEQ ID NO:9 (0.49 kb), SEQ ID NO:14 comprises bases 1001-1450 of SEQ ID NO:9 (0.45 kb), SEQ ID NO:15 comprises bases 1001-1400 of SEQ ID NO:9 (0.40 kb), and SEQ ID NO:16 comprises bases 1201-1450 of SEQ ID NO:9 (0.25 kb).

(SEQ ID NO: 12)
```
CCCAGTCAACCTGCCGACCGTAACCCGGTTCCACCACCGCGGACTGTCCGCAAAACCTGGTT

CGCCCGAGATTAATATGCTATTTCCGGACTAAGTGCACAACACACAAGCACCCCTTCCGCCT

CGCGCTCTAGAATCTGCTTTCTAACCCGGTTCTCGGGCCCTTCCCTTTCGCGACGCCTCCGCT

CTCCTTACCAGGCACCATCCGCAATAGGTAAGGTAGCCAACCGTTTTGGAGCGTGATTCTGC

CAAGGACCGCATCCTTGCATTCGCCATCTGGTCAAGGACCCCTCTTTCCCGCTCCATTCTGGT

GGCTCTATCGGGACGGCGTTCCCCATGGCTCTCCAGGAGAGTGATGTGCGAGTCTGGAGAGC

CGGGGTTGGCGTCACGATGCTGCCCACCTAGGGCCGGCCAGCCCGGCACTGCGCTCCCGTTG
```

-continued

```
ATCCGTCTATCCCCGTCAAGAGCACCAGCCCCGGCGCTCGTGAATTTTCGACTTGTTCGACTT

GCTACAGGTGATAAAGAGGATGCACGCCGCCCTCGATCGGCCTGTGTGGTTTCTCTCCCTC
```

(SEQ ID NO: 13)
```
ATTAATATGCTATTTCCGGACTAAGTGCACAACACACAAGCACCCCTTCCGCCTCGCGCTCT

AGAATCTGCTTTCTAACCCGGTTCTCGGGCCCTTCCCTTTCGCGACGCCTCCGCTCTCCTTAC

CAGGCACCATCCGCAATAGGTAAGGTAGCCAACCGTTTTGGAGCGTGATTCTGCCAAGGACC

GCATCCTTGCATTCGCCATCTGGTCAAGGACCCCTCTTTCCCGCTCCATTCTGGTGGCTCTAT

CGGGACGGCGTTCCCCATGGCTCTCCAGGAGAGTGATGTGCGAGTCTGGAGAGCCGGGGTT

GGCGTCACGATGCTGCCCACCTAGGGCCGGCCAGCCCGGCACTGCGCTCCCGTTGATCCGTC

TATCCCCGTCAAGAGCACCAGCCCCGGCGCTCGTGAATTTTCGACTTGTTCGACTTGCTACA

GGTGATAAAGAGGATGCACGCCGCCCTCGATCGGCCTGTGTGGTTTCTCTCCCTC
```

(SEQ ID NO: 14)
```
CTAGAATCTGCTTTCTAACCCGGTTCTCGGGCCCTTCCCTTTCGCGACGCCTCCGCTCTCCTT

ACCAGGCACCATCCGCAATAGGTAAGGTAGCCAACCGTTTTGGAGCGTGATTCTGCCAAGG

ACCGCATCCTTGCATTCGCCATCTGGTCAAGGACCCCTCTTTCCCGCTCCATTCTGGTGGCTC

TATCGGGACGGCGTTCCCCATGGCTCTCCAGGAGAGTGATGTGCGAGTCTGGAGAGCCGGG

GTTGGCGTCACGATGCTGCCCACCTAGGGCCGGCCAGCCCGGCACTGCGCTCCCGTTGATCC

GTCTATCCCCGTCAAGAGCACCAGCCCCGGCGCTCGTGAATTTTCGACTTGTTCGACTTGCTA

CAGGTGATAAAGAGGATGCACGCCGCCCTCGATCGGCCTGTGTGGTTTCTCTCCCTCGTGCC

AAACCACTCCCACCT
```

(SEQ ID NO: 15)
```
CTAGAATCTGCTTTCTAACCCGGTTCTCGGGCCCTTCCCTTTCGCGACGCCTCCGCTCTCCTT

ACCAGGCACCATCCGCAATAGGTAAGGTAGCCAACCGTTTTGGAGCGTGATTCTGCCAAGG

ACCGCATCCTTGCATTCGCCATCTGGTCAAGGACCCCTCTTTCCCGCTCCATTCTGGTGGCTC

TATCGGGACGGCGTTCCCCATGGCTCTCCAGGAGAGTGATGTGCGAGTCTGGAGAGCCGGG

GTTGGCGTCACGATGCTGCCCACCTAGGGCCGGCCAGCCCGGCACTGCGCTCCCGTTGATCC

GTCTATCCCCGTCAAGAGCACCAGCCCCGGCGCTCGTGAATTTTCGACTTGTTCGACTTGCTA

CAGGTGATAAAGAGGATGCACGCCGCC
```

(SEQ ID NO: 16)
```
TTCCCCATGGCTCTCCAGGAGAGTGATGTGCGAGTCTGGAGAGCCGGGGTTGGCGTCACGAT

GCTGCCCACCTAGGGCCGGCCAGCCCGGCACTGCGCTCCCGTTGATCCGTCTATCCCCGTCA

AGAGCACCAGCCCCGGCGCTCGTGAATTTTCGACTTGTTCGACTTGCTACAGGTGATAAAGA

GGATGCACGCCGCCCTCGATCGGCCTGTGTGGTTTCTCTCCCTCGTGCCAAACCACTCCCACC

T
```

In some embodiments, the C1Cc promoter of the invention comprises SEQ ID NO:17 (1.5 kb). In some embodiments, the C1Cc promoter comprises a subsequence of SEQ ID NO:17, or a variant thereof, as provided herein. In some embodiments, the C1Cc promoter of the invention comprises SEQ ID NO:18, which is the 3' (3-prime) 1 kb of SEQ ID NO:17, which comprises bases 501-1500 of SEQ ID NO:17. In some other embodiments, the C1Cc promoter of the invention comprises SEQ ID NO:19, which is the 3' (3-prime) 0.7 kb of SEQ ID NO:17, which comprises bases 801-1500 of SEQ ID NO:17.

(SEQ ID NO: 17)
```
ATGCGCTCCGCCTTGTGCGCCTCGTGCAGCCGCAGCACCTCGATCAGCACGCGCACCGAGCC

GATCGGGTGGTACAGGTACTCGGACGCCGGCGGGAGCATGTCGGCGAAGGGGACGTCCTC
```

```
TGGAACGAGAGGGCGAACGTGTAGATGGCCAGCCCCGTGAGCGTGCCCTGTTGTTTTGTTTT

TTTGTTTTGTTTTGTTTCCCGTGGTTAGAGGAGGTTTTTTTCGTTTTAGAATGGGAAGGAAGA

AAGGAAAGAAGGAAACTTTGGGGCCGGGTAATGAGGGAGGGAAACGTACGACGGTGATGA

CAACATGGATCCAGCGGCTATGCAGGAACCAGTGGGCGAACGTGTTTGGCGGCGGCGGCAG

GCCCGGGTAGTCGCGGGAGGCTTGCGCGCTGGCCTCCTCGAAGCTGAGGTCGCCGCCGTAGT

GGCGCGGGATGCTCTTCTTCGGCAGGCGGGAGCCGTGTGAGGGGGGATTGAAGCGCTCCGG

CTTGGCGAGCACCCGCTGGCCGGACGGAGTGCCGGCGTTGCTGCTGCTGCTGCTGCTGCTGC

TGTTCCTGGCGAGCCGCAGGAATACGCGGCTCCGGGTCGAGACGGAGGCCGGAGCCGAGGC

CGCCGGAGCCGCCCGGCGCCATATCAGGCCGGTCTGCGGGAGGAGGAAGCGGGGGATGATG

GGTGCTGCTGGTGCCGGCGTCATGACTACTATAACTAACTGCCGCCGCGCGTGTCCGCACAA

ATTTCGAGTGAGCGAGGAATGAATTCGGATTGAGGTAATCCGTAGTGTACGAGCGAGATCC

CTCGAAACGAGGGGAGGCAATCAAAGATTCTTTGTCTCCTCTCCTCCCTCTTTTTTTTGC

TTATCCCCGGTTCCTCTCGGCGACAGAAATGCAACTCGGTTTTTCTGGGTGCCCGATCGGGG

GTCCCTCGGCGTCGGGGCAACAAGGCAATTCGCAGGGTCGCGGACGTTGCGGTGCGGCTCA

ATCAGGCGATATGCGAGTGGTCAGAAAATTCGCCTGCGTCAAGTTGCTGCAGGTTTCTGCTG

CTATCCCATTCCGGCTAGCGCTTCTCTTCTGCTGTGCAGTACTCCGTACACTATAGTAGCTCG

CGGTCCTCGGGCCAAGGCGCGTCTTTGGGTTGCCCGGGGGGGGGTGGCGGCGCGCCAAC

AGTGCCGGTCGCTCCCGAATTTGCCCGGGGCGACTGACTAACAGTCGAAACATGATTGGCAC

AAGTTAGAAAATAGGTGGGTCATTTTTCCACGGATTACCATGGCTCGCTCGTTGGATGATCA

AGGCTTGGCAGTGTTCATCGATGCAAAAAATCCGGCGCGCGGACCTGGCACGGCGATTGCA

GCAAACTAACACCTCATTCCGAAATTTTTCTTGAACTCTTTCCTACTTCCCTTCACATCCGAC

CTTGCTTCGCAATATCTGCTCTTCCTCACCAACACCGACTCCTCTCAGACACTCAATCCTCTC

ACTACCCCAACCGTCAAG (SEQ ID NO: 18)
GCACCCGCTGGCCGGACGGAGTGCCGGCGTTGCTGCTGCTGCTGCTGCTGCTGCTGTTCCTG

GCGAGCCGCAGGAATACGCGGCTCCGGGTCGAGACGGAGGCCGGAGCCGAGGCCGCCGGA

GCCGCCCGGCGCCATATCAGGCCGGTCTGCGGGAGGAGGAAGCGGGGGATGATGGGTGCTG

CTGGTGCCGGCGTCATGACTACTATAACTAACTGCCGCCGCGCGTGTCCGCACAAATTTCGA

GTGAGCGAGGAATGAATTCGGATTGAGGTAATCCGTAGTGTACGAGCGAGATCCCTCGAAA

CGAGGGGAGGCAATCAAAGATTCTTTGTCTCCTCTCCTCCCTCTTTTTTTTGCTTATCCCC

GGTTCCTCTCGGCGACAGAAATGCAACTCGGTTTTTCTGGGTGCCCGATCGGGGGTCCCTCG

GCGTCGGGGCAACAAGGCAATTCGCAGGGTCGCGGACGTTGCGGTGCGGCTCAATCAGGCG

ATATGCGAGTGGTCAGAAAATTCGCCTGCGTCAAGTTGCTGCAGGTTTCTGCTGCTATCCCA

TTCCGGCTAGCGCTTCTCTTCTGCTGTGCAGTACTCCGTACACTATAGTAGCTCGCGGTCCTC

GGGCCAAGGCGCGTCTTTGGGTTGCCCGGGGGGGGGTGGCGGCGCGCCAACAGTGCCGG

TCGCTCCCGAATTTGCCCGGGGCGACTGACTAACAGTCGAAACATGATTGGCACAAGTTAGA

AAATAGGTGGGTCATTTTTCCACGGATTACCATGGCTCGCTCGTTGGATGATCAAGGCTTGG

CAGTGTTCATCGATGCAAAAAATCCGGCGCGCGGACCTGGCACGGCGATTGCAGCAAACTA

ACACCTCATTCCGAAATTTTTCTTGAACTCTTTCCTACTTCCCTTCACATCCGACCTTGCTTCG

CAATATCTGCTCTTCCTCACCAACACCGACTCCTCTCAGACACTCAATCCTCTCACTACCCCA

ACCGTCAAG
```

-continued (SEQ ID NO: 19)
```
TCGAAACGAGGGGAGGCAATCAAAGATTCTTTGTCTCCTCTCTCCTCCCTCTTTTTTTTGCTT

ATCCCCGGTTCCTCTCGGCGACAGAAATGCAACTCGGTTTTTCTGGGTGCCCGATCGGGGGT

CCCTCGGCGTCGGGGCAACAAGGCAATTCGCAGGGTCGCGGACGTTGCGGTGCGGCTCAAT

CAGGCGATATGCGAGTGGTCAGAAAATTCGCCTGCGTCAAGTTGCTGCAGGTTTCTGCTGCT

ATCCCATTCCGGCTAGCGCTTCTCTTCTGCTGTGCAGTACTCCGTACACTATAGTAGCTCGCG

GTCCTCGGGCCAAGGCGCGTCTTTGGGTTGCCCGGGGGGGGGGTGGCGGCGCGCCAACAG

TGCCGGTCGCTCCCGAATTTGCCCGGGGCGACTGACTAACAGTCGAAACATGATTGGCACAA

GTTAGAAAATAGGTGGGTCATTTTTCCACGGATTACCATGGCTCGCTCGTTGGATGATCAAG

GCTTGGCAGTGTTCATCGATGCAAAAAATCCGGCGCGCGGACCTGGCACGGCGATTGCAGC

AAACTAACACCTCATTCCGAAATTTTTCTTGAACTCTTTCCTACTTCCCTTCACATCCGACCTT

GCTTCGCAATATCTGCTCTTCCTCACCAACACCGACTCCTCTCAGACACTCAATCCTCTCACT

ACCCCAACCGTCAAG
```

In some embodiments, the C1Cc promoter of the invention comprises a subsequence of SEQ ID NO:17, SEQ ID NO:18, and/or SEQ ID NO:19 that retains promoter activity, referred to herein as a "short" promoter sequence. Subsequences that retain promoter activity are identified using routine methods well known to those in the art. Provided with SEQ ID NO:17, 18, and/or 19, any of a number of different functional deletion mutants of the starting sequence can be readily prepared. In some embodiments, the subsequences retain constitutive promoter activity (e.g., glucose-independent promoter activity).

In some embodiments, the C1Cc promoter sequence comprises at least about 1000 contiguous nucleotides of SEQ ID NO:17 or 18; at least about 900 nucleotides of SEQ ID NO:17 or18; at least about 800 nucleotides of SEQ ID NO:17 or 18; at least about 700 nucleotides of SEQ ID NO:17, 18, or 19; at least about 600 nucleotides of SEQ ID NO:17, 18, or 19; at least about 500 nucleotides of SEQ ID NO:17, 18, or 19; at least about 450 nucleotides of SEQ ID NO:17, 18, or 19; at least about 400 nucleotides of SEQ ID NO:17, 18, or 19; at least about 350 nucleotides of SEQ ID NO:17, 18, or 19; at least about 300 nucleotides of SEQ ID NO:17, 18, or 19; at least about 250 nucleotides of SEQ ID NO:17, 18, or 19; at least about 200 nucleotides of SEQ ID NO:17, 18, or 19; at least about 150 nucleotides of SEQ ID NO:17, 18, or 19; at least about 100 nucleotides of SEQ ID NO:17, 18, or 19; or at least about 75 contiguous nucleotides of SEQ ID NO:17, 18, or 19.

In some embodiments, the C1Cc promoter sequence comprises a subsequence of comprising about 75 to about 1000 contiguous nucleotides of SEQ ID NO:17 or 18. In some other embodiments the C1Cc promoter sequence comprises a subsequence of SEQ ID NO:17, 18, or 19 comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides.

In some embodiments the subsequence comprises at least about 25, at least about 50, at least about 100, at least about 150 or at least about 200 contiguous nucleotides of SEQ ID NO:19. In some embodiments, the C1Cc promoter sequence comprises at least one of SEQ ID NOS:20-24. SEQ ID NO:20 comprises bases 871-1430 of SEQ ID NO:17 (0.56 kb), while SEQ ID NO:21 comprises bases 941-1430 of SEQ ID NO:17 (0.49 kb), SEQ ID NO:22 comprises bases 1001-1450 of SEQ ID NO:17 (0.45 kb), SEQ ID NO:23 comprises bases 1001-1400 of SEQ ID NO:17 (0.40 kb), and SEQ ID NO:24 comprises bases 1201-1450 of SEQ ID NO:17 (0.25 kb).

(SEQ ID NO: 20)
```
GGTTCCTCTCGGCGACAGAAATGCAACTCGGTTTTTCTGGGTGCCCGATCGGGGGTCCCTCG

GCGTCGGGGCAACAAGGCAATTCGCAGGGTCGCGGACGTTGCGGTGCGGCTCAATCAGGCG

ATATGCGAGTGGTCAGAAAATTCGCCTGCGTCAAGTTGCTGCAGGTTTCTGCTGCTATCCCA

TTCCGGCTAGCGCTTCTCTTCTGCTGTGCAGTACTCCGTACACTATAGTAGCTCGCGGTCCTC

GGGCCAAGGCGCGTCTTTGGGTTGCCCGGGGGGGGGGTGGCGGCGCGCCAACAGTGCCGG

TCGCTCCCGAATTTGCCCGGGGCGACTGACTAACAGTCGAAACATGATTGGCACAAGTTAGA

AAATAGGTGGGTCATTTTTCCACGGATTACCATGGCTCGCTCGTTGGATGATCAAGGCTTGG

CAGTGTTCATCGATGCAAAAAATCCGGCGCGCGGACCTGGCACGGCGATTGCAGCAAACTA

ACACCTCATTCCGAAATTTTTCTTGAACTCTTTCCTACTTCCCTTCACATCCGACCTTGCTTCG

CA
```

```
                                                             (SEQ ID NO: 21)
GCAACAAGGCAATTCGCAGGGTCGCGGACGTTGCGGTGCGGCTCAATCAGGCGATATGCGA

GTGGTCAGAAAATTCGCCTGCGTCAAGTTGCTGCAGGTTTCTGCTGCTATCCCATTCCGGCTA

GCGCTTCTCTTCTGCTGTGCAGTACTCCGTACACTATAGTAGCTCGCGGTCCTCGGGCCAAGG

CGCGTCTTTGGGTTGCCCGGGGGGGGGGTGGCGGCGCGCCAACAGTGCCGGTCGCTCCCG

AATTTGCCCGGGGCGACTGACTAACAGTCGAAACATGATTGGCACAAGTTAGAAAATAGGT

GGGTCATTTTTCCACGGATTACCATGGCTCGCTCGTTGGATGATCAAGGCTTGGCAGTGTTCA

TCGATGCAAAAAATCCGGCGCGCGGACCTGGCACGGCGATTGCAGCAAACTAACACCTCAT

TCCGAAATTTTTCTTGAACTCTTTCCTACTTCCCTTCACATCCGACCTTGCTTCGCA (SEQ ID NO: 22)
AGTGGTCAGAAAATTCGCCTGCGTCAAGTTGCTGCAGGTTTCTGCTGCTATCCCATTCCGGCT

AGCGCTTCTCTTCTGCTGTGCAGTACTCCGTACACTATAGTAGCTCGCGGTCCTCGGGCCAAG

GCGCGTCTTTGGGTTGCCCGGGGGGGGGGTGGCGGCGCGCCAACAGTGCCGGTCGCTCCC

GAATTTGCCCGGGGCGACTGACTAACAGTCGAAACATGATTGGCACAAGTTAGAAAATAGG

TGGGTCATTTTTCCACGGATTACCATGGCTCGCTCGTTGGATGATCAAGGCTTGGCAGTGTTC

ATCGATGCAAAAAATCCGGCGCGCGGACCTGGCACGGCGATTGCAGCAAACTAACACCTCA

TTCCGAAATTTTTCTTGAACTCTTTCCTACTTCCCTTCACATCCGACCTTGCTTCGCAATATCT

GCTCTTCCTCACCA (SEQ ID NO: 23)
AGTGGTCAGAAAATTCGCCTGCGTCAAGTTGCTGCAGGTTTCTGCTGCTATCCCATTCCGGCT

AGCGCTTCTCTTCTGCTGTGCAGTACTCCGTACACTATAGTAGCTCGCGGTCCTCGGGCCAAG

GCGCGTCTTTGGGTTGCCCGGGGGGGGGGTGGCGGCGCGCCAACAGTGCCGGTCGCTCCC

GAATTTGCCCGGGGCGACTGACTAACAGTCGAAACATGATTGGCACAAGTTAGAAAATAGG

TGGGTCATTTTTCCACGGATTACCATGGCTCGCTCGTTGGATGATCAAGGCTTGGCAGTGTTC

ATCGATGCAAAAAATCCGGCGCGCGGACCTGGCACGGCGATTGCAGCAAACTAACACCTCA

TTCCGAAATTTTTCTTGAACTCTTTCCT (SEQ ID NO: 24)
GCGACTGACTAACAGTCGAAACATGATTGGCACAAGTTAGAAAATAGGTGGGTCATTTTTCC

ACGGATTACCATGGCTCGCTCGTTGGATGATCAAGGCTTGGCAGTGTTCATCGATGCAAAAA

ATCCGGCGCGCGGACCTGGCACGGCGATTGCAGCAAACTAACACCTCATTCCGAAATTTTTC

TTGAACTCTTTCCTACTTCCCTTCACATCCGACCTTGCTTCGCAATATCTGCTCTTCCTCACCA
```

In some embodiments, the C1Cd promoter of the invention comprises SEQ ID NO:25 (1.5 kb). In some embodiments, the C1Cd promoter comprises a subsequence of SEQ ID NO:25, or a variant thereof, as provided herein. In some embodiments, the C1Cd promoter of the invention comprises SEQ ID NO:26, which is the 3' (3-prime) 1 kb of SEQ ID NO:25, comprising bases 501-1500 of SEQ ID NO:25. In some embodiments, the C1Cd promoter of the invention comprises SEQ ID NO:27, which is the 3' (3-prime) 0.7 kb of SEQ ID NO:25, comprising bases 801-1500 of SEQ ID NO:25.

```
                                                             (SEQ ID NO: 25)
              GCTCGAGGATGTCAAAGTCCACATTTCATTTTTTTCTTTTTCTTTTTTTTTTCCGGATAGGC

ATCTTCCATTTGGGAATCATAGATGTCTGCTTACGGGCGGTGTGCGAGCCGTGGTGCTCGG

CTTTTTGGGGTAAGAATGGCCCATGACGGAGCGATGGCGGTTTTAGTTCAAGGTGCTCGTGT

CCTGATGATAGATGATATTGGTGTGACGTGGTGTGTTCTGCAGATTTTTGAAGCTTGGGGGA

TGTAACTCGGCCCAAGAGGAAAGTGCGGAGATGTGTGCTCAATCGAGGTACTTAATGTTCCG

TATTCTTTCCTCCTCAGGCTATTATCTCGTGCAGTGGCGAATCTGAAGAGTGTCACGGGTACT
```

-continued

```
TCGTAGGTACCAAAGCTTCACCGTCTTTGGACACGTCGATAGCGACGTACCTGCAGCAGTGG

TCTGATGTGTCTGAAATTTGTCTTGATTCCCGATGGCGACAGGTGTCTGTTATGAGAACCTAC

CTGACCGAGAGTGGCCAGGCAAGAGAACCAATAGCTATATTTTCAAACTCGCTATTTCAAGC

TTGACCTCGAAATGGAAAACCGACTATCAGCAGTGACAATCAATCACGGGCCAGAGTGCAT

TAAATGGATGTACTGTGGGATGCGGAAAGCGAACTATAGTATCTTCGTTTAACTGCTACTGC

TGCTGGTAAGTGGTGGTCGAAGGAAGCGAAGGCTGACTGGGGCCACCGTGCAGGAAGATAT

GGGTGGCTGTAACCCTGGTGGGGCCGGGAGCCCTAGTGGGGCCCGACCACCACAAGTATGT

ACTGTGTACGTCCGTATATACGGATTACATACATACCTACACAGTATAATTATCTGCGCATTG

ATTTCCGGAGAAACTACTCCGTACCTAGGTATACAGAAAAGAACCGCCAACGAAAAGTAAT

TAATTACGTACGCATCACGACTCGCACTCCTTTCCAGCGTACAAGGATTGTTTTGATTCCCTT

TGAGGATGACATTCATTCCACGATACCAATGAGATAGCGGGTTTGGACATTTTTGACTCGAA

CGGAAATGATGAACAGCAAGCAGTATTAGTCGGCTCTCACACGCACACTGGCATCAAGCAG

CAATCGAACACTTGCCGACTCAACGCATCATGACGGCAAAAACCCACGTGGGCATGATGTC

CAAGTCCCTATATTCAGGAACCCCCCGGACCAGATGACGCATGGTACGGTACCTATGTGACA

TCAGGCTCGCCACCAGTTGTCTGTTCCCTATTATAATCCGCCTATTAATTAATTAGTAGCTCT

GATTTGTAAAAGTGCAAGCCTGTTCTGATCATCTTCATGACCTCTACTCTGCAAGTCCGAACA

AGAGATCACCATCAATTGCATATTATTTGATAATTAATACACTGTATCTGTACAAAGAACAG

CACAAAACATATTTTTCTCCTGAATAATTATTACTACTCCCCCAGACCCAAACAAAAAAGTC

TAATTACACC
```

(SEQ ID NO: 26)
```
CTGACCGAGAGTGGCCAGGCAAGAGAACCAATAGCTATATTTTCAAACTCGCTATTTCAAGC

TTGACCTCGAAATGGAAAACCGACTATCAGCAGTGACAATCAATCACGGGCCAGAGTGCAT

TAAATGGATGTACTGTGGGATGCGGAAAGCGAACTATAGTATCTTCGTTTAACTGCTACTGC

TGCTGGTAAGTGGTGGTCGAAGGAAGCGAAGGCTGACTGGGGCCACCGTGCAGGAAGATAT

GGGTGGCTGTAACCCTGGTGGGGCCGGGAGCCCTAGTGGGGCCCGACCACCACAAGTATGT

ACTGTGTACGTCCGTATATACGGATTACATACATACCTACACAGTATAATTATCTGCGCATTG

ATTTCCGGAGAAACTACTCCGTACCTAGGTATACAGAAAAGAACCGCCAACGAAAAGTAAT

TAATTACGTACGCATCACGACTCGCACTCCTTTCCAGCGTACAAGGATTGTTTTGATTCCCTT

TGAGGATGACATTCATTCCACGATACCAATGAGATAGCGGGTTTGGACATTTTTGACTCGAA

CGGAAATGATGAACAGCAAGCAGTATTAGTCGGCTCTCACACGCACACTGGCATCAAGCAG

CAATCGAACACTTGCCGACTCAACGCATCATGACGGCAAAAACCCACGTGGGCATGATGTC

CAAGTCCCTATATTCAGGAACCCCCCGGACCAGATGACGCATGGTACGGTACCTATGTGACA

TCAGGCTCGCCACCAGTTGTCTGTTCCCTATTATAATCCGCCTATTAATTAATTAGTAGCTCT

GATTTGTAAAAGTGCAAGCCTGTTCTGATCATCTTCATGACCTCTACTCTGCAAGTCCGAACA

AGAGATCACCATCAATTGCATATTATTTGATAATTAATACACTGTATCTGTACAAAGAACAG

CACAAAACATATTTTTCTCCTGAATAATTATTACTACTCCCCCAGACCCAAACAAAAAAGTC

TAATTACACC
```

(SEQ ID NO: 27)
```
AGTATGTACTGTGTACGTCCGTATATACGGATTACATACATACCTACACAGTATAATTATCTG

CGCATTGATTTCCGGAGAAACTACTCCGTACCTAGGTATACAGAAAAGAACCGCCAACGAA

AAGTAATTAATTACGTACGCATCACGACTCGCACTCCTTTCCAGCGTACAAGGATTGTTTTG

ATTCCCTTTGAGGATGACATTCATTCCACGATACCAATGAGATAGCGGGTTTGGACATTTTTG
```

-continued

```
ACTCGAACGGAAATGATGAACAGCAAGCAGTATTAGTCGGCTCTCACACGCACACTGGCAT

CAAGCAGCAATCGAACACTTGCCGACTCAACGCATCATGACGGCAAAAACCCACGTGGGCA

TGATGTCCAAGTCCCTATATTCAGGAACCCCCCGGACCAGATGACGCATGGTACGGTACCTA

TGTGACATCAGGCTCGCCACCAGTTGTCTGTTCCCTATTATAATCCGCCTATTAATTAATTAG

TAGCTCTGATTTGTAAAAGTGCAAGCCTGTTCTGATCATCTTCATGACCTCTACTCTGCAAGT

CCGAACAAGAGATCACCATCAATTGCATATTATTTGATAATTAATACACTGTATCTGTACAA

AGAACAGCACAAAACATATTTTTCTCCTGAATAATTATTACTACTCCCCCAGACCCAAACAA

AAAAGTCTAATTACACC
```

In some embodiments, the C1Cd promoter of the invention comprises a subsequence of SEQ ID NO:25, SEQ ID NO:26, and/or SEQ ID NO:27 that retains promoter activity, referred to herein as a "short" promoter sequence. Subsequences that retain promoter activity are identified using routine methods well known to those in the art. Provided with SEQ ID NO:25, 26, and/or 27, any of a number of different functional deletion mutants of the starting sequence can be readily prepared. In some embodiments, the subsequences retain constitutive promoter activity (e.g., glucose-independent promoter activity).

In some embodiments, the C1Cd promoter sequence comprises at least about 1000 contiguous nucleotides of SEQ ID NO:25 or 26; at least about 900 nucleotides of SEQ ID NO:25 or 26; at least about 800 nucleotides of SEQ ID NO:25 or 26; at least about 700 nucleotides of SEQ ID NO:25, 26, or 27; at least about 600 nucleotides of SEQ ID NO:25, 26, or 27; at least about 500 nucleotides of SEQ ID NO:25, 26, or 27; at least about 450 nucleotides of SEQ ID NO:25, 26, or 27; at least about 400 nucleotides of SEQ ID NO:25, 26, or 27; at least about 350 nucleotides of SEQ ID NO:25, 26, or 27; at least about 300 nucleotides of SEQ ID NO:25, 26, or 27; at least about 250 nucleotides of SEQ ID NO:25, 26, or 27; at least about 200 nucleotides of SEQ ID NO:25, 26, or 27; at least about 150 nucleotides of SEQ ID NO:25, 26 or 27; at least about 100 nucleotides of SEQ ID NO:25, 26, or 27; or at least about 75 contiguous nucleotides of SEQ ID NO:25, 26, or 27.

In some embodiments, the C1Cd promoter sequence comprises a subsequence comprising about 75 to about 1000 contiguous nucleotides of SEQ ID NO:25 or 26. In some other embodiments, the C1Cd promoter sequence comprises a subsequence of SEQ ID NO:25, 26, or 27 comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides. In some embodiments, the subsequence comprises at least about 25, at least about 50, at least about 100, at least about 150, or at least about 200 contiguous nucleotides of SEQ ID NO:27. In some embodiments the C1Cd promoter sequence comprises at least one of SEQ ID NOS:28-32. SEQ ID NO:28 comprises bases 871-1430 of SEQ ID NO:25 (0.56 kb), while SEQ ID NO:29 comprises bases 941-1430 of SEQ ID NO:25(0.49 kb), SEQ ID NO:30 comprises bases 1001-1450 of SEQ ID NO:25 (0.45 kb), SEQ ID NO:31 comprises bases 1001-1400 of SEQ ID NO:25 (0.40 kb), and SEQ ID NO:32 comprises bases 1201-1450 of SEQ ID NO:25 (0.25 kb).

```
                                                          (SEQ ID NO: 28)
ATTTCCGGAGAAACTACTCCGTACCTAGGTATACAGAAAAGAACCGCCAACGAAAAGTAAT

TAATTACGTACGCATCACGACTCGCACTCCTTTCCAGCGTACAAGGATTGTTTTGATTCCCTT

TGAGGATGACATTCATTCCACGATACCAATGAGATAGCGGGTTTGGACATTTTTGACTCGAA

CGGAAATGATGAACAGCAAGCAGTATTAGTCGGCTCTCACACGCACACTGGCATCAAGCAG

CAATCGAACACTTGCCGACTCAACGCATCATGACGGCAAAAACCCACGTGGGCATGATGTC

CAAGTCCCTATATTCAGGAACCCCCCGGACCAGATGACGCATGGTACGGTACCTATGTGACA

TCAGGCTCGCCACCAGTTGTCTGTTCCCTATTATAATCCGCCTATTAATTAATTAGTAGCTCT

GATTTGTAAAAGTGCAAGCCTGTTCTGATCATCTTCATGACCTCTACTCTGCAAGTCCGAACA

AGAGATCACCATCAATTGCATATTATTTGATAATTAATACACTGTATCTGTACAAAGAACAG

CA
                                                          (SEQ ID NO: 29)
ACGCATCACGACTCGCACTCCTTTCCAGCGTACAAGGATTGTTTTGATTCCCTTTGAGGATGA

CATTCATTCCACGATACCAATGAGATAGCGGGTTTGGACATTTTTGACTCGAACGGAAATGA

TGAACAGCAAGCAGTATTAGTCGGCTCTCACACGCACACTGGCATCAAGCAGCAATCGAAC

ACTTGCCGACTCAACGCATCATGACGGCAAAAACCCACGTGGGCATGATGTCCAAGTCCCTA
```

-continued

```
TATTCAGGAACCCCCCGGACCAGATGACGCATGGTACGGTACCTATGTGACATCAGGCTCGC

CACCAGTTGTCTGTTCCCTATTATAATCCGCCTATTAATTAATTAGTAGCTCTGATTTGTAAA

AGTGCAAGCCTGTTCTGATCATCTTCATGACCTCTACTCTGCAAGTCCGAACAAGAGATCAC

CATCAATTGCATATTATTTGATAATTAATACACTGTATCTGTACAAAGAACAGCA
```

(SEQ ID NO: 30)
```
TGACATTCATTCCACGATACCAATGAGATAGCGGGTTTGGACATTTTTGACTCGAACGGAAA

TGATGAACAGCAAGCAGTATTAGTCGGCTCTCACACGCACACTGGCATCAAGCAGCAATCG

AACACTTGCCGACTCAACGCATCATGACGGCAAAAACCCACGTGGGCATGATGTCCAAGTC

CCTATATTCAGGAACCCCCCGGACCAGATGACGCATGGTACGGTACCTATGTGACATCAGGC

TCGCCACCAGTTGTCTGTTCCCTATTATAATCCGCCTATTAATTAATTAGTAGCTCTGATTTGT

AAAAGTGCAAGCCTGTTCTGATCATCTTCATGACCTCTACTCTGCAAGTCCGAACAAGAGAT

CACCATCAATTGCATATTATTTGATAATTAATACACTGTATCTGTACAAAGAACAGCACAAA

ACATATTTTTCTCCTG
```

(SEQ ID NO: 31)
```
TGACATTCATTCCACGATACCAATGAGATAGCGGGTTTGGACATTTTTGACTCGAACGGAAA

TGATGAACAGCAAGCAGTATTAGTCGGCTCTCACACGCACACTGGCATCAAGCAGCAATCG

AACACTTGCCGACTCAACGCATCATGACGGCAAAAACCCACGTGGGCATGATGTCCAAGTC

CCTATATTCAGGAACCCCCCGGACCAGATGACGCATGGTACGGTACCTATGTGACATCAGGC

TCGCCACCAGTTGTCTGTTCCCTATTATAATCCGCCTATTAATTAATTAGTAGCTCTGATTTGT

AAAAGTGCAAGCCTGTTCTGATCATCTTCATGACCTCTACTCTGCAAGTCCGAACAAGAGAT

CACCATCAATTGCATATTATTTGATAAT
```

(SEQ ID NO: 32)
```
CCCCGGACCAGATGACGCATGGTACGGTACCTATGTGACATCAGGCTCGCCACCAGTTGTCT

GTTCCCTATTATAATCCGCCTATTAATTAATTAGTAGCTCTGATTTGTAAAAGTGCAAGCCTG

TTCTGATCATCTTCATGACCTCTACTCTGCAAGTCCGAACAAGAGATCACCATCAATTGCATA

TTATTTGATAATTAATACACTGTATCTGTACAAAGAACAGCACAAAACATATTTTTCTCCTG
```

In some embodiments, the C1Ce promoter of the invention comprises SEQ ID NO:33 (1.5 kb). In some embodiments, the C1Ce promoter comprises a subsequence of SEQ ID NO:33, or a variant thereof, as provided herein. In some embodiments, the C1Ce promoter of the invention comprises SEQ ID NO:34, which is the 3' (3-prime) 1 kb of SEQ ID NO:33, comprising bases 501-1500 of SEQ ID NO:33. In some embodiments, the C1Ce promoter of the invention comprises SEQ ID NO:35, which is the 3' (3-prime) 0.7 kb of SEQ ID NO:33, comprising bases 801-1500 of SEQ ID NO:33.

(SEQ ID NO: 33)
```
CCAACCGAACCCCCATCGTCGCAGCCCCTCTCGCTTTTGAAACGGCTCCCAAGCCACTTAAA

CCCGCTAGAGCACTCTCTCAAGCCAGCGCGGTGGGTCTAGCCTACGTACGATACACCCCCAC

CCCCAAACAACCGTGACAGGATACACGACTCCCACAACACAATGGATAGGATGCACGATGG

ATGAACCGAGGACGGAGGCACACAAGAAATGCAATGTGGCCCTTCTCGGCGGAAGCACACG

GGCTGTAGGGAGCGGGGGGAAAAGGAGACAGACAGGCGTCCTTGCAGCAGAGGGTTTGA

AGTCGACCCACACACACCGATGAAGCCGCCTTTTGCAGCCTCTCTCTCGTCATCACCGCCCTC

CTCGAGTTCAGGCAGTTTGCCGCTTTGCCTCGTGCACACATAGGGCCCGGCATTTTTCCTGGG

CATGGAATTCTGGAATGAAGACCAGGACATCAATCTGCGTCGGGCGAGGCAACGCCGAAGA

GCTGTTGTATTCCGGACACTCGTATACTGACCCTAAACGTGTATGTATGCACAGTACAATGA

AAGATTCGAAATGGGGAAAAAGTAGCCAATGCATACGTACGTACGAAGGAACGCATTGAGC

ATTCGACACTAGTTCTGACCTTCAAAAAACCGTCATTCGAATCTGGACCTGGCTTGTCAGTTA
```

-continued

```
TGGTGTTTGACTGAGTGCCAGGTGAGTCGAGCACTAACGAAGGGAGTGCTTTAAAACCCTTC

CAGGCTGCTCCAGACACCCTGATTCTGGGGCTGCTGCAGGAATCGACACGGGGAAGAAGCA

GCATTGTTTCAGAATGTAGACATCAAGCGGGTCCGGAAAGCACATGTATGGAAAGTAAGTA

CCTCCGTACGGAGTACTGCATGTCCATCCGTACTTGAGGAAACGCTGAGGTAACATGGAGGT

AGAAGAAACCACGAGAGACTATGGGTTACACCTGCTCAAACCCACTGCACCTCTCCTCTGGG

GATTTTCCGACTCTTCCCCTGCTTGAATGCACAGACAGCTGTGTCTTTGGTACACTTTACTAA

AGACCACAGCCAAGCGGGAGAAAACGGGGACGATGAGTCACGTCCGGGAGATTCCGGCCTG

CTGTGTCGGAAGCAATCAGCTGAGCTGCTCAATCCTGAACTTTCAGTACACGGCTGCCAACT

GAGTTGCAGCGGTCCGAAGCGTTCCGAGTCCTTTGTCAGTTGCTTTTTCGCTTAGTTTATTCC

TTGGACCAGCTCTTGTCAAAGACCGAAAATGCTTTCGGGAGTAAGAGCGCTTGGGATTTGGG

GTTATGTCATAGACCGGATGAAGTCGGCCTGTGGTCCCTTCGTTTTCCTGCCTTCCCCTTGAG

GTGGCTTGCGAACAAACGTATAAATGATGTATCACTCTCCAAGACATGCCCGTACTCGCCTT

GATGAATCTCAGACTCGTGATCCATCGCGACAAGACAGTATATTGGCAGCCATCTGTCTGTT

GAAGCTTTCAACCCC (SEQ ID NO: 34)
TATTCCGGACACTCGTATACTGACCCTAAACGTGTATGTATGCACAGTACAATGAAAGATTC

GAAATGGGGAAAAAGTAGCCAATGCATACGTACGTACGAAGGAACGCATTGAGCATTCGAC

ACTAGTTCTGACCTTCAAAAAACCGTCATTCGAATCTGGACCTGGCTTGTCAGTTATGGTGTT

TGACTGAGTGCCAGGTGAGTCGAGCACTAACGAAGGGAGTGCTTTAAAACCCTTCCAGGCT

GCTCCAGACACCCTGATTCTGGGGCTGCTGCAGGAATCGACACGGGGAAGAAGCAGCATTG

TTTCAGAATGTAGACATCAAGCGGGTCCGGAAAGCACATGTATGGAAAGTAAGTACCTCCG

TACGGAGTACTGCATGTCCATCCGTACTTGAGGAAACGCTGAGGTAACATGGAGGTAGAAG

AAACCACGAGAGACTATGGGTTACACCTGCTCAAACCCACTGCACCTCTCCTCTGGGGATTT

TCCGACTCTTCCCCTGCTTGAATGCACAGACAGCTGTGTCTTTGGTACACTTTACTAAAGACC

ACAGCCAAGCGGGAGAAAACGGGGACGATGAGTCACGTCCGGGAGATTCCGGCCTGCTGTG

TCGGAAGCAATCAGCTGAGCTGCTCAATCCTGAACTTTCAGTACACGGCTGCCAACTGAGTT

GCAGCGGTCCGAAGCGTTCCGAGTCCTTTGTCAGTTGCTTTTTCGCTTAGTTTATTCCTTGGA

CCAGCTCTTGTCAAAGACCGAAAATGCTTTCGGGAGTAAGAGCGCTTGGGATTTGGGGTTAT

GTCATAGACCGGATGAAGTCGGCCTGTGGTCCCTTCGTTTTCCTGCCTTCCCCTTGAGGTGGC

TTGCGAACAAACGTATAAATGATGTATCACTCTCCAAGACATGCCCGTACTCGCCTTGATGA

ATCTCAGACTCGTGATCCATCGCGACAAGACAGTATATTGGCAGCCATCTGTCTGTTGAAGC

TTTCAACCCC (SEQ ID NO: 35)
CAGCATTGTTTCAGAATGTAGACATCAAGCGGGTCCGGAAAGCACATGTATGGAAAGTAAG

TACCTCCGTACGGAGTACTGCATGTCCATCCGTACTTGAGGAAACGCTGAGGTAACATGGAG

GTAGAAGAAACCACGAGAGACTATGGGTTACACCTGCTCAAACCCACTGCACCTCTCCTCTG

GGGATTTTCCGACTCTTCCCCTGCTTGAATGCACAGACAGCTGTGTCTTTGGTACACTTTACT

AAAGACCACAGCCAAGCGGGAGAAAACGGGGACGATGAGTCACGTCCGGGAGATTCCGGC

CTGCTGTGTCGGAAGCAATCAGCTGAGCTGCTCAATCCTGAACTTTCAGTACACGGCTGCCA

ACTGAGTTGCAGCGGTCCGAAGCGTTCCGAGTCCTTTGTCAGTTGCTTTTTCGCTTAGTTTAT

TCCTTGGACCAGCTCTTGTCAAAGACCGAAAATGCTTTCGGGAGTAAGAGCGCTTGGGATTT
```

-continued
```
GGGGTTATGTCATAGACCGGATGAAGTCGGCCTGTGGTCCCTTCGTTTTCCTGCCTTCCCCTT

GAGGTGGCTTGCGAACAAACGTATAAATGATGTATCACTCTCCAAGACATGCCCGTACTCGC

CTTGATGAATCTCAGACTCGTGATCCATCGCGACAAGACAGTATATTGGCAGCCATCTGTCT

GTTGAAGCTTTCAACCCC
```

In some embodiments, the C1Ce promoter of the invention comprises a subsequence of SEQ ID NO:33, SEQ ID NO:34, and/or SEQ ID NO:35 that retains promoter activity, referred to herein as a "short" promoter sequence. Subsequences that retain promoter activity are identified using routine methods well known to those in the art. Provided with SEQ ID NO:33, SEQ ID NO:34, and/or SEQ ID NO:35, any of a number of different functional deletion mutants of the starting sequence can be readily prepared. In some embodiments, the subsequences retain constitutive promoter activity (e.g., glucose-independent promoter activity).

In some embodiments, the C1Ce promoter sequence comprises at least about 1000 contiguous nucleotides of SEQ ID NO:33 or 34; at least about 900 nucleotides of SEQ ID NO:33 or 34; at least about 800 nucleotides of SEQ ID NO:33 or 34; at least about 700 nucleotides of SEQ ID NO:33, SEQ ID NO:34, or SEQ ID NO:35; at least about 600 nucleotides of SEQ ID NO:33, SEQ ID NO:34, or SEQ ID NO:35; at least about 500 nucleotides of SEQ ID NO:33, SEQ ID NO:34, or SEQ ID NO:35; at least about 450 nucleotides of SEQ ID NO:33, SEQ ID NO:34, or SEQ ID NO:35; at least about 400 nucleotides of SEQ ID NO:33, SEQ ID NO:34, or SEQ ID NO:35; at least about 350 nucleotides of SEQ ID NO:33, SEQ ID NO:34, or SEQ ID NO:35; at least about 300 nucleotides of SEQ ID NO:33, SEQ ID NO:34, or SEQ ID NO:35; at least about 250 nucleotides SEQ ID NO:33, SEQ ID NO:34, or SEQ ID NO:35; at least about 200 nucleotides of SEQ ID NO:33, SEQ ID NO:34, or SEQ ID NO:35; at least about 150 nucleotides of SEQ ID NO:33, SEQ ID NO:34, or SEQ ID NO:35; at least about 100 nucleotides of SEQ ID NO:33, SEQ ID NO:34, or SEQ ID NO:35; or at least about 75 contiguous nucleotides of SEQ ID NO:33, SEQ ID NO:34, or SEQ ID NO:35.

In some embodiments, the C1Ce promoter sequence comprises a subsequence comprising about 75 to about 1000 contiguous nucleotides of SEQ ID NO:33 or 34. In some other embodiments, the C1Ce promoter sequence comprises a subsequence of SEQ ID NO:33, SEQ ID NO:34, or SEQ ID NO:35, comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides. In some embodiments, the subsequence comprises at least about 25, at least about 50, at least about 100, at least about 150, or at least about 200 contiguous nucleotides of SEQ ID NO:35. In some embodiments, the C1Ce promoter sequence comprises at least one of SEQ ID NOS:36-40. SEQ ID NO:36 comprises bases 871-1430 of SEQ ID NO:33 (0.56 kb), while SEQ ID NO:37 comprises bases 941-1430 of SEQ ID NO:33 (0.49 kb), SEQ ID NO:38 comprises bases 1001-1450 of SEQ ID NO:33 (0.45 kb), SEQ ID NO:39 comprises bases 1001-1400 of SEQ ID NO:33 (0.40 kb), and SEQ ID NO:40 comprises bases 1201-1450 of SEQ ID NO:33 (0.25 kb).

```
                                                                 (SEQ ID NO: 36)
ACGGAGTACTGCATGTCCATCCGTACTTGAGGAAACGCTGAGGTAACATGGAGGTAGAAGA

AACCACGAGAGACTATGGGTTACACCTGCTCAAACCCACTGCACCTCTCCTCTGGGGATTTT

CCGACTCTTCCCCTGCTTGAATGCACAGACAGCTGTGTCTTTGGTACACTTTACTAAAGACCA

CAGCCAAGCGGGAGAAAACGGGGACGATGAGTCACGTCCGGGAGATTCCGGCCTGCTGTGT

CGGAAGCAATCAGCTGAGCTGCTCAATCCTGAACTTTCAGTACACGGCTGCCAACTGAGTTG

CAGCGGTCCGAAGCGTTCCGAGTCCTTTGTCAGTTGCTTTTTCGCTTAGTTTATTCCTTGGAC

CAGCTCTTGTCAAAGACCGAAAATGCTTTCGGGAGTAAGAGCGCTTGGGATTTGGGGTTATG

TCATAGACCGGATGAAGTCGGCCTGTGGTCCCTTCGTTTTCCTGCCTTCCCCTTGAGGTGGCT

TGCGAACAAACGTATAAATGATGTATCACTCTCCAAGACATGCCCGTACTCGCCTTGATGAA

T (SEQ ID NO: 37)
AGACTATGGGTTACACCTGCTCAAACCCACTGCACCTCTCCTCTGGGGATTTTCCGACTCTTC

CCCTGCTTGAATGCACAGACAGCTGTGTCTTTGGTACACTTTACTAAAGACCACAGCCAAGC

GGGAGAAAACGGGGACGATGAGTCACGTCCGGGAGATTCCGGCCTGCTGTGTCGGAAGCAA

TCAGCTGAGCTGCTCAATCCTGAACTTTCAGTACACGGCTGCCAACTGAGTTGCAGCGGTCC

GAAGCGTTCCGAGTCCTTTGTCAGTTGCTTTTTCGCTTAGTTTATTCCTTGGACCAGCTCTTGT

CAAAGACCGAAAATGCTTTCGGGAGTAAGAGCGCTTGGGATTTGGGGTTATGTCATAGACC
```

```
                                                         -continued
GGATGAAGTCGGCCTGTGGTCCCTTCGTTTTCCTGCCTTCCCCTTGAGGTGGCTTGCGAACAA

ACGTATAAATGATGTATCACTCTCCAAGACATGCCCGTACTCGCCTTGATGAAT (SEQ ID NO: 38)
TTCCCCTGCTTGAATGCACAGACAGCTGTGTCTTTGGTACACTTTACTAAAGACCACAGCCA

AGCGGGAGAAAACGGGGACGATGAGTCACGTCCGGGAGATTCCGGCCTGCTGTGTCGGAAG

CAATCAGCTGAGCTGCTCAATCCTGAACTTTCAGTACACGGCTGCCAACTGAGTTGCAGCGG

TCCGAAGCGTTCCGAGTCCTTTGTCAGTTGCTTTTTCGCTTAGTTTATTCCTTGGACCAGCTCT

TGTCAAAGACCGAAAATGCTTTCGGGAGTAAGAGCGCTTGGGATTTGGGGTTATGTCATAGA

CCGGATGAAGTCGGCCTGTGGTCCCTTCGTTTTCCTGCCTTCCCCTTGAGGTGGCTTGCGAAC

AAACGTATAAATGATGTATCACTCTCCAAGACATGCCCGTACTCGCCTTGATGAATCTCAGA

CTCGTGATCCATCG (SEQ ID NO: 39)
TTCCCCTGCTTGAATGCACAGACAGCTGTGTCTTTGGTACACTTTACTAAAGACCACAGCCA

AGCGGGAGAAAACGGGGACGATGAGTCACGTCCGGGAGATTCCGCCTGCTGTGTCGGAAG

CAATCAGCTGAGCTGCTCAATCCTGAACTTTCAGTACACGGCTGCCAACTGAGTTGCAGCGG

TCCGAAGCGTTCCGAGTCCTTTGTCAGTTGCTTTTTCGCTTAGTTTATTCCTTGGACCAGCTCT

TGTCAAAGACCGAAAATGCTTTCGGGAGTAAGAGCGCTTGGGATTTGGGGTTATGTCATAGA

CCGGATGAAGTCGGCCTGTGGTCCCTTCGTTTTCCTGCCTTCCCCTTGAGGTGGCTTGCGAAC

AAACGTATAAATGATGTATCACTCTC (SEQ ID NO: 40)
GTCCTTTGTCAGTTGCTTTTTCGCTTAGTTTATTCCTTGGACCAGCTCTTGTCAAAGACCGAA

AATGCTTTCGGGAGTAAGAGCGCTTGGGATTTGGGGTTATGTCATAGACCGGATGAAGTCGG

CCTGTGGTCCCTTCGTTTTCCTGCCTTCCCCTTGAGGTGGCTTGCGAACAAACGTATAAATGA

TGTATCACTCTCCAAGACATGCCCGTACTCGCCTTGATGAATCTCAGACTCGTGATCCATCG
```

In some embodiments, the present invention provides sequences comprising tandem duplication of at least two promoters, derived sub-sequences and/or "short" sequences, comprising C1Ca, C1Cb, C1Cc, C1Cd and/or C1Ce, in any combination.

Promoter Variants

It is not intended that the present invention be limited specifically to SEQ ID NO:1, SEQ ID NO:2, SEQ ID NO:3; SEQ ID NO:9, SEQ ID NO:10, SEQ ID NO:11, SEQ ID NO:17, SEQ ID NO:18, SEQ ID NO:19, SEQ ID NO:25, SEQ ID NO:26, SEQ ID NO:27, SEQ ID NO:33, SEQ ID NO:34, and/or SEQ ID NO:35 or subsequences thereof (e.g., short promoters provided herein). It will be appreciated by a person of skill guided by this disclosure that promoter regions can tolerate considerable variation and without diminution of activity. Thus, the invention encompasses C1C promoters that (a) hybridize under stringent conditions to SEQ ID NO:1; SEQ ID NO:9; SEQ ID NO:17; SEQ ID NO:25 and/or SEQ ID NO:33; or (b) comprise a sequence substantially identical to SEQ ID NO:1; SEQ ID NO:9; SEQ ID NO:17; SEQ ID NO:25 and/or SEQ ID NO:33 and/or a subsequence thereof. Variants are further described herein. Any suitable method for introducing variation into a promoter sequence and identifying variants that retains promoter activity find use in the present invention, including but not limited to the specific methods set forth herein.

In some embodiments, promoters of the invention include sequences (e.g., variant sequences) having promoter activity and with at least about 20%, at least about 25%, at least about 30%, at least about 35%, about 40%, at least about 45%, at least about 50%, at least about 55%, about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, and/or at least about 99% sequence identity to any of the subsequences provided herein (i.e., SEQ ID NOS:2-8, 10-16, 18-24, 26-32, and 34-40). In some embodiments, the variant sequences comprise about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides of SEQ ID NOS:2-8, 10-16, 18-24, 26-32, and/or 34-40. In some embodiments the promoter comprises a sequence of at least about 100 nucleotides that differs from the corresponding subsequence of SEQ ID NOS:2-8, 10-16, 18-24, 26-32, and/or 34-40, at one or more (e.g., 1, 2, 3, 4, 5, 6, 7, 8, 9, 10, 20, 25, 30, or 40) nucleotides.

The promoters provided in the present invention can be characterized using any suitable method known in the art. For example, in some embodiments, the specific C1C promoters (e.g., C1Ca, C1Cb, C1Cc, C1Cd and/or C1Ce) of the present invention are characterized by their ability to hybridize under high stringency hybridization conditions to SEQ ID NO:1;

SEQ ID NO:9; SEQ ID NO:17; SEQ ID NO:25 and/or SEQ ID NO:33 or the complement of, SEQ ID NO:1; SEQ ID NO:9; SEQ ID NO:17; SEQ ID NO:25 and/or SEQ ID NO:33. In some embodiments, the C1Ca promoter of the invention can be characterized by its ability to hybridize under high stringency hybridization conditions to SEQ ID NO:1 and/or the complement of SEQ ID NO:1. In some embodiments, the C1Cb promoter of the invention can be characterized by its ability to hybridize under high stringency hybridization conditions to SEQ ID NO:9 and/or the complement of SEQ ID NO:9. In some embodiments, the C1Cc promoter of the invention can be characterized by its ability to hybridize under high stringency hybridization conditions to SEQ ID NO:17 and/or the complement of SEQ ID NO:17. In some embodiments, the C1Cd promoter of the invention can be characterized by its ability to hybridize under high stringency hybridization conditions to SEQ ID NO:25 and/or the complement of SEQ ID NO:25. In some embodiments, the C1Ce promoter of the invention can be characterized by its ability to hybridize under high stringency hybridization conditions to SEQ ID NO:33 and/or the complement of SEQ ID NO:33. As used herein, the phrase "high stringency hybridization conditions" refers to hybridization at about 5° C. to 10° C. below the $T_M$ of the respective C1Ca promoter (e.g., SEQ ID NO:1), C1Cb (e.g., SEQ ID NO:9), C1Cc (e.g., SEQ ID NO: 17), C1Cd (e.g., SEQ ID NO 25), and/or C1Ce (e.g., SEQ ID NO:33) melting temperature (TM) of the hybridized duplex sequence, followed by washing at 0.2×SSC/0.1% SDS at 37° C. for 45 minutes. The melting temperature of the nucleic acid hybrid can be calculated using methods well known to those in the art.

In some embodiments, C1Ca promoters of the invention are characterized based on alignment with SEQ ID NO:1 (e.g., C1Ca promoter sequences less than 1.5 kb are aligned to the corresponding subsequence of SEQ ID NO:1.) C1Ca promoters of the invention include sequences with at least about 80%, at least about 90%, at least about 91%, at least about 92%, at least about 93%, at least about 94%, at least about 95%, at least about 96%, at least about 97%, at least about 98%, and at least about 99% sequence identity to SEQ ID NO: 1, 2, or 3 or to short promoters described herein having promoter activity. Thus, in some embodiments, the C1Ca promoter has a sequence that has at least about 80%, at least about 90%, at least about 91%, at least about 92%, at least about 93%, at least about 94%, at least about 95%, at least about 96%, at least about 97%, at least about 98%,and/or at least 99% sequence identity to a subsequence of SEQ ID NO:1 comprising about 75 to about 1000 contiguous nucleotides of SEQ ID NO:1 or 2, and/or a subsequence of SEQ ID NO:1, 2 or 3 comprising about 50 to about 700; about 50 to about 600, about 50 to about 500; about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides. For example, in some embodiments, the C1Ca promoter sequence has at least about 90% or at least about 95% sequence identity to SEQ ID NO:3, or a subsequence of at least about 100, at least about 200, at least about 300, at least about 400 or at least about 500 bases of SEQ ID NO:3. In another example, the C1Ca promoter sequence may have at least 90% or at least 95% sequence identity to SEQ ID NO:2, or a subsequence of at least about 100, at least about 200, at least about 300, at least about 400 or at least about 500 bases of SEQ ID NO:2. In some embodiments, the C1Ca promoter comprises a sequence of at least about 100 bases that differs from the corresponding subsequence of SEQ ID NO:1 at one or more (e.g., 1, 2, 3, 4, 5, 6, 7, 8, 9, 10 or more) bases.

In some embodiments, the C1Cb promoters of the invention can be characterized based on alignment with SEQ ID NO:9 (i.e., C1Cb promoter sequences less than about 1.5 kb are aligned to the corresponding subsequence of SEQ ID NO:9.) In some embodiments, C1Cb promoters of the invention include sequences with at least about 80%, at least about 90%, at least about 91%, at least about 92%, at least about 93%, at least about 94%, at least about 95%, at least about 96%, at least about 97%, at least about 98%, and at least about 99% sequence identity to SEQ ID NO: 9, 10, and/or 11, and/or to short promoters described herein having promoter activity. Thus, in some embodiments the C1Cb promoter has a sequence that has at least about 80%, at least about 90%, at least about 91%, at least about 92%, at least about 93%, at least about 94%, at least about 95%, at least about 96%, at least about 97%, at least about 98%, and/or at least about 99% sequence identity to a subsequence comprising about 75 to about 1000 contiguous nucleotides of SEQ ID NO:9 or 10, or a subsequence of SEQ ID NO:9, 10 or 11 comprising about 50 to about 700, about 50 to about 600, about 50 to about 500, about 50 to about 400, about 50 to about 300, 50 to 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides SEQ ID NO:9, 10 and/or 11. For example, in some embodiments, the C1Cb promoter sequence comprises at least about 90%, or at least about 95% sequence identity to SEQ ID NO:11, and/or a subsequence of at least about 100, at least about 200, at least about 300, at least about 400, or at least about 500 bases of SEQ ID NO:11. In some embodiments, the C1Cb promoter sequence comprises at least about 90% or at least about 95% sequence identity to SEQ ID NO:10, or a subsequence of at least about 100, at least about 200, at least about 300, at least about 400, or at least about 500 bases of SEQ ID NO:10. In some embodiments, the C1Cb promoter comprises a sequence of at least about 100 bases that differs from the corresponding subsequence SEQ ID NO:9 at one or more (e.g., 1, 2, 3, 4, 5, 6, 7, 8, 9, 10 or more) bases.

In some embodiments, C1Cc promoter of the invention are characterized based on alignment with SEQ ID NO:17 (i.e., C1Cc promoter sequences less than 1.5 kb are aligned to the corresponding subsequence of SEQ ID NO:17.) C1Cc promoters of the invention include sequences with at least about 80%, at least about 90%, at least about 91%, at least about 92%, at least about 93%, at least about 94%, at least about 95%, at least about 96%, at least about 97%, at least about 98%, and/or at least about 99% sequence identity to SEQ ID NOS: 17, 18, and/or 19 and/or to short promoters described hereinabove having promoter activity. Thus, in some embodiments, the C1Cc promoters have sequence that are at least about 80%, at least about 90%, at least about 91%, at least about 92%, at least about 93%, at least about 94%, at least about 95%, at least about 96%, at least about 97%, at least about 98%, and/or at least about 99% sequence identity to a subsequence comprising about 75 to about 1000 contiguous nucleotides of SEQ ID NO: 17 and/or 18, and/or a subsequence of SEQ ID NO:17, 18, and/or 19, comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides. In some embodiments, the C1Cc promoter sequences comprise at least 90% or at least 95% sequence identity to SEQ ID NO:19, or a subsequence of at least about 100, at least about 200, at least about 300, at least about 400 or at least about 500 bases of SEQ ID NO:19. In some other embodiments, the C1Cc promoter sequences comprise at least about 90% or at least about 95% sequence identity to SEQ ID NO:18, or a subsequence of at least about 100, at least about 200, at least about 300, at least about 400 or at least about 500 bases of SEQ ID NO:18. In some embodiments the C1Cc promoter comprises a sequence of at least about 100 bases that differs from the corresponding subsequence SEQ ID NO:17 at one or more (e.g., 1, 2, 3, 4, 5, 6, 7, 8, 9, 10 or more) bases.

In some embodiments, C1Cd promoters of the present invention are characterized based on alignment with SEQ ID NO:25 (i.e., C1Cd promoter sequences less than about 1.5 kb are aligned to the corresponding subsequence of SEQ ID NO:25.) C1Cd promoters of the invention include sequences with at least about 80%, at least about 90%, at least about 91%, at least about 92%, at least about 93%, at least about 94%, at least about 95%, at least about 96%, at least about 97%, at least about 98%, and/or at least about 99% sequence identity to SEQ ID NO: 25, 26, and/or 27, and/or to short promoters described herein having promoter activity. Thus, in some embodiments, the C1Cd promoter has a sequence that has at least about 80%, at least about 85%, at least about 90%, at least about 91%, at least about 92%, at least about 93%, at least about 94%, at least about 95%, at least about 96%, at least about 97%, at least about 98%, and/or at least about 99% sequence identity to a subsequence comprising about 75 to about 1000 contiguous nucleotides of SEQ ID NO:25 and/or 26, and/or a subsequence of SEQ ID NO:25, 26, and/or 27, comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides. In some embodiments, the C1Cd promoter sequences have at least about 90% or at least about 95% sequence identity to SEQ ID NO:27, and/or a subsequence of at least about 100, at least about 200, at least about 300, at least about 400, or at least about 500 bases of SEQ ID NO:27. In some other embodiments, the C1Cd promoter sequences have at least about 90% or at least about 95% sequence identity to SEQ ID NO:26, and/or a subsequence of at least about 100, at least about 200, at least about 300, at least about 400, or at least about 500 bases of SEQ ID NO:26. In some embodiments, the C1Cd promoter comprises a sequence of at least about 100 bases that differs from the corresponding subsequence SEQ ID NO:25 at one or more (e.g., 1, 2, 3, 4, 5, 6, 7, 8, 9, 10 or more) bases.

In some embodiments, the C1Ce promoters of the present invention are characterized based on alignment with SEQ ID NO:33 (i.e., C1Ce promoter sequences less than about 1.5 kb are aligned to the corresponding subsequence of SEQ ID NO:33.) C1Ce promoters of the invention include sequences with at least about 80%, at least about 85%, at least about 90%, at least about 91%, at least about 92%, at least about 93%, at least about 94%, at least about 95%, at least about 96%, at least about 97%, at least about 98%, and at least about 99% sequence identity to SEQ ID NOS:33, 34, and/or 35, and/or to short promoters described herein having promoter activity. Thus, in some embodiments, the C1Ce promoter has a sequence that has at least about 80%, at least about 90%, at least about 91%, at least about 92%, at least about 93%, at least about 94%, at least about 95%, at least about 96%, at least about 97%, at least about 98%, and at least about 99% sequence identity to a subsequence comprising about 75 to about 1000 contiguous nucleotides of SEQ ID NOS:33 and/or 34, and/or a subsequence of SEQ ID NOS: 33, 34, and/or 35 comprising about 50 to about 700, about 50 to about 600, about 50 to about 500, about 50 to about 400, about 50 to about 300, about 50 to about 200, about 75 to about 700, about 75 to about 600, about 75 to about 500, about 75 to about 400, about 75 to about 300, about 75 to about 200, about 100 to about 700, about 100 to about 600, about 100 to about 500, about 100 to about 400, about 100 to about 300, or about 100 to about 200 contiguous nucleotides. For example, in some embodiments, the ClCe promoter sequences have at least about 90% or at least about 95% sequence identity to SEQ ID NO:35, and/or a subsequence of at least about 100, at least about 200, at least about 300, at least about 400, or at least about 500 bases of SEQ ID NO:35. In some other embodiments, the C1Ce promoter sequences have at least about 90% or at least about 95% sequence identity to SEQ ID NO:34, and/or a subsequence of at least about 100, at least about 200, at least about 300, at least about 400, or at least about 500 bases of SEQ ID NO:34. In some embodiments, the C1Ce promoter comprises a sequence of at least about 100 bases that differs from the corresponding subsequence SEQ ID NO:33 at one or more (e.g., 1, 2, 3, 4, 5, 6, 7, 8, 9, 10 or more) bases.

Any of the sequences provided herein can be prepared and screened for activity utilizing standard methods known in the art. For example, any of SEQ ID NOS:1, 2, 3, 9, 10, 11, 17, 18, 19, 25, 26, 27, 33, 34 and 35, and short promoter sequences disclosed herein, as well as any of a number of different functional variant sequences can be readily prepared and screened for function. For example, mutagenesis and, optionally, directed evolution methods can be readily applied to polynucleotides such as, for example, the wild-type C1Ca promoter sequence (e.g., SEQ ID NO: 1), C1Cb (e.g., SEQ ID NO:9), C1Cc (e.g., SEQ ID NO:17), C1Cd (e.g., SEQ ID NO:25), and/or the wild-type C1Ce promoter sequence (e.g., SEQ ID NO: 33). Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455, 253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2): 157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391: 288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

One targeted method for preparing mutagenized promoters relies upon the identification of putative regulatory elements within the target sequence by, for example, comparison with promoter sequences known to be expressed in a similar manner. Sequences that are shared are likely candidates for the binding of transcription factors and are thus likely elements which confer expression patterns. Confirmation of such putative regulatory elements can be achieved by deletion analysis of each putative regulatory region followed by functional analysis of each deletion construct by assay of a reporter gene which is functionally attached to each construct.

To produce a vector such as an expression cassette utilizing the C1C promoters of this invention for gene expression, a variety of methods well known in the art find use in obtaining the polynucleotide sequences for the promoter and the coding sequence of interest, and join the two sequences so that they are operably linked for gene expression. In some embodiments, the polypeptide coding sequence encodes at least one detectable protein (e.g., proteins of interest for production and conventional reporter proteins for routine screening for promoter activity).

In some embodiments, the protein is an or at least one enzyme, including but not limited to cellulases, hemicellulases, glucoamylases, amylases (e.g., alpha amylases and/or abeta amylases), proteases (e.g., acid proteases, alkali proteases, neutral proteases, pepsin, peptidases, trypsin, chymosin, or subtilisin), phytases, lipases, esterases, xylanases, reductases, oxidoreductases, laccases, oxidases, cutinases, isomerases (e.g., glucose isomerase or xylose isomerase), pullulanases, phenol oxidizing enzymes, starch hydrolyzing enzymes, mannanases, mannases, catalases, glucose oxidases, transferases, lyases (e.g., pectate lyase or acetolactate decarboxylase), cellobiohydrolases, endoglucanases, beta-glucoidases, alpha-glucosidases, aminopeptidases, carbohydrases, carboxypeptidases, catalases, chitinases, cutinases, cyclodextrin glycosyltransferases, deoxyribonucleases, alpha-galactosidases, beta-galactosidases, glucocerebrosidases, invertases, mannosidases, mutanases, oxidases, pectinolytic enzymes, peroxidases, phospholipases, phytases, polyphenoloxidases, ribonucleases, and trans-glutaminases. In some embodiments, the enzyme is a bacterial enzyme, while in some other embodiments, the enzyme is a fungal enzyme. Indeed, it is not intended that the present invention be limited to the enzyme source, as any suitable prokaryotic and/or eukaryotic enzymes find use in the present invention. Furthermore, in some embodiments, the protein and/or enzyme is a variant of a wild type or naturally occurring enzyme. In some embodiments, the recombinant expression constructs comprise a protein-coding sequence that is an endogenous gene operably linked to a promoter of the present invention.

It is not intended that the present invention be limited to any particular enzyme family or class. However, it is intended that the promoters of the present invention will find use in driving the expression of numerous families or classes of enzymes, including, but not limited to oxidoreductases (E.C.1); transferases (E.C.2); hydrolyases (E.C.3); lyases (E.C.4); isomerases (E.C. 5) and ligases (E.C. 6). More specific, but non-limiting subgroups of oxidoreductases include dehydrogenases (e.g., alcohol dehydrogenases (carbonyl reductases), xylulose reductases, aldehyde reductases, farnesol dehydrogenase, lactate dehydrogenases, arabinose dehydrogenases, glucose dehyrodgenase, fructose dehydrogenases, xylose reductases and succinate dehyrogenases), oxidases (e.g., glucose oxidases, hexose oxidases, galactose oxidases and laccases), monoamine oxidases, lipoxygenases, peroxidases, aldehyde dehydrogenases, reductases, long-chain acyl-[acyl-carrier-protein] reductases, acyl-CoA dehydrogenases, enereductases, synthases (e.g., glutamate synthases), nitrate reductases, mono and di-oxygenases, and catalases. More specific, but non-limiting subgroups of transferases include methyl, amidino, carboxyl, and phosphotransferases, transketolases, transaldolases, acyltransferases, glycosyltransferases, transaminases, transglutaminases and polymerases. More specific, but non-limiting subgroups of hydrolases include invertases, ester hydrolases, peptidases, glycosylases, amylases, cellulases, hemicellulases, xylanases, chitinases, glucosidases, glucanases, glucoamylases, acylases, galactosidases, pullulanases, phytases, lactases, arabinosidases, nucleosidases, nitrilases, phosphatases, lipases, phospholipases, proteases, ATPases, and dehalogenases. More specific, but non-limiting subgroups of lyases include decarboxylases, aldolases, hydratases, dehydratases (e.g., carbonic anhydrases), synthases (e.g., isoprene, pinene and farnesene synthases), pectinases (e.g., pectin lyases) and halohydrin dehydrogenases. More specific, but non-limiting subgroups of isomerases include racemases, epimerases, isomerases (e.g., xylose, arabinose, ribose, glucose, galactose and mannose isomerases), tautomerases, and mutases (e.g. acyl transferring mutases, phosphomutases, and aminomutases. More specific, but non-limiting subgroups of ligases include ester synthases.

In some embodiments, the enzyme is a cellulase such as an endoglucanase (E.C. 3.2.1.4 also called β-1,4 endoglucanases), an exoglucanases (E.C. 3.2.1.91, also called cellobiohydrolases), or beta-glucosidase (E.C. 3.2.1.21 also called cellobiases). Additional cellulases include, but are not limited to invertases, xylanases, and GH61s. Numerous cellulases are known and described in the literature (See e.g., U.S. Pat. Nos. 6,287,839 and 6,562,612; Jung et al., Appl. Environ. Microbiol. 59:3032-3043 [1993]; and Lao et al, J. Bacteriol. 173: 3397-3407 [1991]).

In some embodiments, the coding sequence encodes for a protein such as an enzyme, a therapeutic protein, a receptor protein, etc. In some further embodiments, the protein is a protease, such as a metallo, thiol, acid or serine protease (e.g., subtilisin). In some additional embodiments, the coding sequence which is operably linked to any of the C1C promoters of the invention encodes a protein other than an enzyme (e.g., hormones, receptors, growth factors, antigens and antibodies, including single chain antibodies and antibody heavy and light chains). In some additional embodiments, the protein coding sequences operably linked to any of the C1C promoters are chimeric or fusion proteins. For example, in some embodiments, the proteins include epitope tags (e.g., c-myc, $HIS_6$ or maltose-binding protein) to aid in purification. It is not intended that the present invention be limited to any specific protein, protein coding sequence, and/or epitope tag.

In some embodiments, the protein comprises a conventional or commercially available reporter protein such as but not limited to beta-galatosidase (lacZ), beta-glucuronidase (GUS), fluorescent protein (GFP), luciferase, chloramphenicol, or acetyl transferase (CAT). Any protein for which expression can be measured (e.g., by enzymatic, immunological or physical methods) finds use as a reporter. Although conventional reporters tend to be better suited to high throughput screening, production of any protein can be assayed by immunological methods, mass spectroscopy, etc. Alternatively, expression can be measured at the level of transcription by assaying for production of specific RNAs.

In some embodiments, the reporter protein is a fungal enzyme, such as a fungal cellulase, such as a C1 cellulase or variant thereof. For example, in some embodiments, the promoter(s) find use in driving expression of a C1 beta-glucosidase and expression of the enzyme measured using p-nitrophenyl-beta-D-glucoside-based assay. In some embodiments, the promoters are used to drive expression of a C1 cellobiohydrolase and expression of the cellobiohydrolase measured using a 4-methylumbelliferyl betaD-lactopyranoside (MUL) assay known in the art. In some embodiments, the promoters are used to drive expression of C1 endoglucanse (EG) and expression of EG measured using a azo-CMC assay known in the art.

Signal Peptides

In some embodiments, a polypeptide product is secreted extracellularly by host cells comprising vectors comprising at least one promoter provided herein. In some embodiments, a signal sequence is used to produce a protein comprising a signal peptide at the amino-terminus of the protein. The signal sequence may be endogenous or exogenous to the host organism. If an endogenous signal peptide is used, it may or may not be naturally associated with the protein. For example, the promoter may be operably linked to a sequence encoding (i) a C1 Cbh1a signal sequence fused to a C1 Cbh1a mature protein sequence (e.g, the wildtype C1 Cbh1a), (ii) a C1 Bgl1 signal sequence fused to a C1 Cbh1a mature protein sequence, or (iii) an exogenous, non-C1, signal peptide fused to a a C1 Cbh1a mature protein sequence. A signal sequence not naturally associated with the coding sequence may be required when the coding sequence does not normally contain a signal peptide coding region, or may replace the natural signal peptide coding region to enhance secretion of the protein relative to secretion achieved with the natural signal peptide.

Exemplary non-C1 signal peptides which may be used in C1 or other filamentous fungi include, for illustration and not limitation, a signal sequence from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. However, any signal peptide coding region capable of directing the expressed polypeptide into the secretory pathway of a host cell of choice may be used in the present invention, and one skilled in the art is well aware of numerous signal sequences that may be used depending on the protein being produced and secreted in a host organism.

Expression Construct

The promoter sequence of the present invention and any coding sequence of interest may be operably linked in an expression construct (e.g., an expression vector). A number of known methods are suitable for the purpose of ligating the two sequences, such as ligation methods based on PCR and ligation methods mediated by various ligases (e.g., bacteriophase T4 ligase). The promoter used to direct expression of a heterologous sequence is optionally positioned about the same distance from the heterologous translation start site as it is from the translation start site in its natural setting. However, as is known in the art, some variation in this distance can be accommodated without loss of promoter function. Where there is a 3' or internal deletion relative to the promoter sequence, this can be accomplished by inserting a number of nucleotides approximately equal to the number deleted (e.g., inserting from about 70 to about 130% of the number deleted, sometimes about 80 to about 120%, and sometimes about 90 to about 110%). It will be appreciated that the vector may comprise flanking sequences (i.e., additional nucleotides) 5' to the C1C promoter sequences and 3' to the protein coding sequence.

In some embodiments, when the C1C promoter sequence of the invention is not truncated at the 3'end (for example, SEQ ID NOS:1-3,9-11,17-19,25-27,and 33-35) the promoter sequence is linked to the protein coding sequence at or close to the start codon (e.g., the 5'-UTR of the heterologous gene is deleted). In another approach, all or a portion of the 5'-UTR of the heterologous gene is retained and a 3' portion of any of the C1C promoter is deleted to maintain the same spacing between upstream promoter elements and the translation start site. However, in general, it may be preferred to retain the complete promoter sequence.

In addition to the promoter, the expression construct optionally contains all the additional elements required for the expression of the heterologous sequence in host cells, such as signals required for efficient polyadenylation of the transcript, translation termination, and optionally enhancers. If genomic DNA is used as the heterologous coding sequence, introns may also be included.

The expression construct is typically contained in an expression vector that also includes a replicon that functions in bacterial and/or yeast and/or other host cells, and may contain a gene encoding a selectable marker to permit selection of microorganisms that harbor recombinant vectors. Selectable markers are well known and widely used in the art and include antibiotic resistance genes, metabolic selection markers, and the like. Exemplary selectable markers for use in filamentous fungi include amdS, argB, bar, hygB, niaD, pyrG, sC, trpC and the like.

In addition to episomal DNA based expression, the expression construct comprising any of the C1C promoter sequences (e.g., SEQ ID NOS: 1-40) and a polypeptide coding sequence may be integrated into the host genome such as by homologous recombination. In some alternative embodiments, the expression construct is randomly integrated into the host chromosome (e.g., by non-homologous recombination). In some embodiments, a promoter of the invention is introduced into a plasmid harboring a DNA fragment encoding a protein sequence of interest (e.g., a cellulase), for targeted integration into the genome at a desired site. Methods of targeted integration are known (See e.g., Gaillardin and Ribet, Curr. Genet., 11: 369-375 [1987]).

Host Cells

The present invention also provides a recombinant cell comprising a promoter of the invention operably linked to a protein coding sequence. In some embodiments, the host cell is a eukaryotic cell, such as fungal cells, algal cells, insect cells, and plant cells. In some other embodiments the host cell is a fungal cell such as a yeast cell or a filamentous fungus cell. In some embodiments, the host cell is filamentous fungal cell, including but not limited to *Aspergillus, Chrysosporium, Corynascus, Fusarium, Humicola, Hypocrea, Myceliopth-* thora, Mucor, Neurospora, Penicillium, Rhizomucor, Rhizopus, Talaromyces, Thermoascus, Thielavia, Trametes, Trichoderma, or teleomorphs, or anamorphs, and synonyms or taxonomic equivalents thereof. In some embodiments, the host cell is a *Myceliophthora* species, such as *Myceliophthora thermophilia*. Indeed, cross-species use of promoters is well known (See e.g., Punt et al., J. Biotechnol., 17:19-33 [1991]; and Roberts et al., Curr Genet, 15:177-80 [1989]).

As used herein, the term "C1" refers to *Myceliophthora thermophilia*, including a fungal strain described by Garg (See, Garg, Mycopathol., 30: 3-4 [1966]). As used herein, "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation, Chrysosporium lucknowense Garg 27K, VKM-F 3500 D (Accession No. VKM F-3500-D), C1 strain UV 13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV18#100f Δalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO2008073914 and WO2010107303, each of which is incorporated herein by reference.

Strains that find use in the practice of the invention include both prokaryotic and eukaryotic strains obtainable from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). However it is not intended that only strains available from these collections will find use with the present invention.

Promoters of the invention may be employed in host cells (e.g., a *Myceliopthera* strain such as *Myceliophthora thermophilia*) or any other suitable filamentous fungal host cells, that are genetically modified to have characteristics that improve expression (e.g., improve protein secretion, protein stability or other properties desirable for expression and/or secretion of a protein). Genetic modification can be achieved by any suitable known genetic engineering techniques and/or using classical microbiological techniques, such as chemical or UV mutagenesis and subsequent selection. A combination of recombinant modification and classical selection techniques may be used to produce the organism of interest. For example, using recombinant technology, nucleic acid molecules can be introduced, deleted, inhibited or otherwise modified in a host cell. In some embodiments, a host cell is modified to reduce or eliminate expression of an endogenous gene. For example, a genetically modified host cell may have a modification introduced into the cell using homologous recombination to specifically suppress expression a targeted gene. In an alternative approach, interfering RNA, antisense, or ribozyme technology can be used to inhibit gene expression in a host cell.

Thus, in some embodiments, the host cells are modified to have characteristics that improve protein secretion, protein stability and/or other properties desirable for expression and/or secretion of a protein. For example, knock out of alp1 function results in a cell that is protease deficient, while knock out of pyr5 function results in a cell with a pyrimidine-deficient phenotype. In some embodiments, host cells are modified to delete endogenous cellulase protein-encoding sequences or otherwise eliminate expression of one or more endogenous cellulases. In some embodiments, expression of one or more endogenous enzymes is inhibited to increase production of cellulases of interest. Genetic modification can be achieved by any suitable method, including but not limited to genetic engineering techniques or using classical microbiological techniques, such as chemical or UV mutagenesis and subsequent selection. In one genetic engineering approach, homologous recombination can be used to induce targeted gene modifications by specifically targeting a gene in vivo to suppress expression of the encoded protein. In one alternative approach, siRNA, antisense, or ribozyme technology can be used to inhibit gene expression.

Standard transformation methods find use in producing recombinant host cells harboring the expression vector of the present invention. For example, introduction of a vector into a host cell can be achieved by any suitable method, including but not limited to calcium phosphate transfection, DEAE-dextran mediated transfection, electroporation, PEG-mediated protoplast transformation, and/or other common techniques well known to those in the art.

The recombinant or engineered host cells can be cultured in conventional nutrient media modified as appropriate for activating promoters and selecting transformants. Culture conditions, such as temperature, pH and the like will be apparent to those skilled in the art. In addition, some culture conditions may be obtained from the American Type Culture Collection (ATCC).

Promoter Activity Assays

It will be understood that not every subsequence of, or variant of the promoter sequence (e.g., SEQ ID NO:1, 9, 17, 25 or 33), will have C1 promoter activity, or constitutive C1 promoter activity. However, routine screening may be used to identify those variants and subsequences with the desired properties. For example, starting with a given sequence (e.g., SEQ ID NO: 1, 9, 17, 25 or 33) fragments of different sizes can be operatively linked to a reporter protein and the ability of the fragment to drive expression can be measured. If desired, a deletion series can be made beginning at the 5' end of the sequence using exo- or endo-nucleases and the effect of truncation on promoter activity can be determined Alternatively, random fragments of the target sequence (e.g., SEQ ID NO: 1, 9, 17, 25 or 33) can be generated, cloned in front of the reporter protein coding sequence, and expression of the reporter measured. Controls, such as for differences in gene copy number, are typically employed. In addition, high-throughput methods may be used to assay promoter activity. Indeed various methods known in the art find use in the present invention (See e.g., McNabb et al., Eukary. Cell, 4:1539-49 [2005]; Bell et al., Yeast 15:1747-59 [1999]; Bron et al., Appl. Environ. Microbiol., 70:310-17 [2004]; Alper et al., Proc. Nat'l. Acad. Sci. USA, 102:12678-83 [2005]).

In some embodiments, the C1 promoter activity of a polynucleotide (i.e., "promoter sequence") can be determined using any suitable methods. For example, the promoter sequence is cloned into an expression vector encoding C1 beta-glucosidase (SEQ ID NO:41; See, FIG. 1), using any suitable method known in the art. Then, the expression construct is introduced into a C1 cell to produce a "host cell." Introduction of a vector or a DNA construct into a host cell using any suitable method known in the art (including but not limited to calcium phosphate transfection, DEAE-dextran mediated transfection, electroporation, or other common techniques). Next, the host cell is cultured under normal conditions. Suitable culture conditions for C1 host cells are well known in the art (See e.g., US Pat. Appln. Publ. Nos. 2008/0194005 and US 20030187243; WO 08/073914 and WO 01/79507, each of which is incorporated herein by reference). Wild-type or recombinant host cells can be cultured in conventional nutrient media as known in the art and described in the scientific literature. After a suitable period of incubation (e.g., 24-72 hours), the culture medium (i.e., broth) is removed and the β-glucosidase activity is measured. Several β-glucosidase activity assays are well known in the art. One suitable assay is the colorimetric pNPG (p-nitrophenyl-β-D-glucopyranoside)-based assay. Briefly, in a total volume of 100 μL, 20 μL clear media supernatant containing β-glucosidase enzyme is added to 4 mM pNPG (Sigma-Aldrich) solution in 50 mM sodium phosphate buffer at pH 5. The reactions are incubated at pH 5, 50° C. for 1.5 hours. The reaction mixture is quenched with 100 μL of 1M sodium carbonate pH 11 solution. The absorbance of the solution is measured at 405 nm to determine the conversion of pNPG to p-nitrophenol. The release of p-nitrophenol ($\epsilon=17,700$ M-1 cm-1) is measured at 405 nm to calculate β-glucosidase activity. Detectable β-glucosidase activity is observed under high throughput screening conditions (pH 7, 50° C.) (See e.g., Breves et al., Appl. Environmental Microbiol., 63:3902 [1997], incorporated herein by reference). Alternatively, the level of C1 β-glucosidase protein can be measured directly using well known methods. For example, immunological methods such as radioimmunoassays and/or quantitative "immunoblotting" may be used. In addition, promoter activity can be compared to expression of endogenous C1 beta-glucosidase. Promoter activity can be measured relative to the activity of wild-type promoter sequences (e.g., SEQ ID NO:1, 9, 17, 25 or 33).

Constitutive (i.e., glucose-independent) promoter activity can be assayed generally as above, but expression in the presence or absence of 10 g/L glucose can be compared. A promoter may be considered constitutive if the expression level in the presence of 10 g/L glucose for 1 hour differs from expression in the absence of glucose by no more than 50% of the non-glucose levels. In some embodiments, the difference is less than about 25%, while in some other embodiments, it is sometimes less than about 10%.

In some embodiments, short and/or variant C1C promoters have at least the same level of promoter activity as the activity exhibited by wild-type C1C promoter sequences (e,g.,SEQ ID NO:1, 9, 17, 25 or 33) under equivalent conditions (e.g., expression in C1). In some embodiments, the promoter activity is greater, for example at least about 5%, at least about 10%, at least about 15%, at least about 20%, at least about 25%, at least about 30%, at least about 40%, or at least about 50%.

Host cells comprising a C1C promoter of the invention operatively linked to a sequence encoding a cellulase or other cellulose degrading enzyme may be used, for illustration and not for limitation, in saccharification of cellulosic biomass. In some embodiments, cells comprising a C1C promoter and expressing a coding sequence are grown under batch, fed-batch or continuous culture conditions, well known in the art.

In some embodiments, the cells of the invention are used to produce a recombinant protein of interest, such as a therapeutic protein. In some embodiments the protein is isolated from the cells or culture media.

EXPERIMENTAL

The following examples are provided by way of illustration only and not by way of limitation. Those of skill in the art will readily recognize a variety of non-critical parameters that could be changed or modified to yield essentially the same or similar results. The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); by (base pair); kbp (kilo base pair); CDW (cell dry weight); HPLC (high pressure liquid chromatography); ARS (ARS Culture Collection or NRRL Culture Collection, Peoria, Ill.); and Sigma-Aldrich (Sigma-Aldrich, St. Louis, Mo.).

Example 1

Identification of Fungal Promoters from C1 Cells

Oligonucleotide microarrays were designed based on genes identified by bioinformatics analysis of the C1 genomic sequence. Each predicted gene was represented by at least four different oligonucleotides spanning the entire gene sequence.

C1 cells (wild-type and an Alp1-deficient strain) were grown in separate shake flasks in the presence of lactose. Cells were cultured for 3 days and then collected ("uninduced cells"), or cultured for an additional hour in the presence of 10 g/L glucose ("induced cells"). RNA was collected from induced and uninduced cells and used to prepare cDNA probes for hybridization in the microarrays.

Twenty-two genes regulated by constitutive promoters were identified. For each, a fragment containing approximately 1.5 kb of sequence upstream from the translation start site was cloned into an expression vector so that the upstream sequence was operably linked to a sequence encoding an endogenous C1 cellulase protein. Transformants were selected and a cellulase activity assay was used to determine amount of cellulase secreted into culture medium (See, FIG. 2). Five promoters (IP092, IP102, IP103, IP104 and IP105) were identified as strong constitutive promoters showing cellulase overexpression relative to expression of the endogenous cellulase (designated "C1V34" in FIG. 2). The C1Ca promoter corresponds to IP104. The C1Cb promoter corresponds to IP092. The C1Cc promoter corresponds to IP102. The C1Cd promoter corresponds to IP105. The C1Ce promoter corresponds to IP 103.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto. The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of this invention.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

What is claimed is:

1. An expression construct comprising a recombinant polynucleotide having promoter activity comprising a nucleotide sequence with at least 90% sequence identity to the nucleotide sequence set forth in any of SEQ ID NOs:1, 17, 25, or 33, operably linked to at least one heterologous DNA sequence encoding at least one protein.

2. The expression construct of claim 1, wherein the protein comprises a signal peptide fused to a secreted protein sequence.

3. The expression construct of claim 2, wherein the signal peptide is not associated with the secreted protein in nature.

4. The expression construct of claim 1, wherein said at least one protein comprises at least one enzyme.

5. The expression construct of claim 4, wherein said at least one enzyme comprises at least one cellulase.

6. The expression construct of claim 5, wherein the at least one cellulase comprises an endoglucanase, a cellobiohydrolase andor a p-glucosidase.

7. The expression construct of claim 4, wherein said at least one enzyme comprises a glucoamylase, protease, alpha amylase, cellulase, hemicellulase, xylanase, esterase, cutinase, phytase, lipase, oxidoreductase, reductase, dehydrogenase, synthase, invertase, laccase, isomerase, pullulanase, phenol oxidizing enzyme, mannanase, mannose, catalase, glucose oxidase, transferase, and/or lyase.

8. The expression construct of claim 4, wherein said at least one enzyme comprises at least one recombinant enzyme.

9. A host cell comprising the expression construct of claim 1.

10. The host cell of claim 9, wherein said cell is a yeast or filamentous fungal cell.

11. The host cell of claim 9, wherein said cell is *Myceliophthora thermophile*.

12. The host cell of claim 9, wherein said expression cassette is integrated into the genome of said host cell.

13. A method for producing a protein in a host cell, comprising culturing the host cell of claim 9, under conditions such that said protein is produced by said host cell.

14. The method of claim 13, further comprising the step of isolating said protein produced by said host cell.

* * * * *

SEQUENCE LISTING

```
<160> NUMBER OF SEQ ID NOS: 42

<210> SEQ ID NO 1
<211> LENGTH: 1500
<212> TYPE: DNA
<213> ORGANISM: Artificial sequence
<220> FEATURE:
<223> OTHER INFORMATION: Synthetic oligonucleotide

<400> SEQUENCE: 1
cttgggtaat gtaatccgtc cagcacatgt cttgacatgc ttgatgtatg tactctatat     60
attgagtaca gtacctgtct tgaagagcag tacagtatac tctctggatg gacttcggtg    120
cttggacggg aataataact tagggtttgc gctaaggtag actagcagcc aatgaaatcg    180
gctcagtggc acgagatact ttaaagtgta cggagtactc cgtacggaac acagactcaa    240
caaattgcca tgaccatgca gctctctctc gcagcgagat gagagaccca catagcattc    300
caaccatgtg aggaagtcta ttagtacggc ttatgagtgt actccggacc actctagtta    360
gttgtatgca cgatctgtcg aagagatcgg tggtaactcg ccagcatggg cataccattt    420
caaaccaaga tttttatgcg agcatcaaac tccacaactc agcgtccgca gcaggcatcg    480
gagagttggc accctcagcc cttttacact agaactagat ttctgcaaaa gctcttgtgc    540
aaggctgcat acagatacac tagagtaagg tgcttagcta atatactaaa gcgtattagt    600
cccaatccca tgcaagctgc gagaggtcgc aatttcccga ctcggcgccg catgcgctag    660
tgtggactgg gaatcgcggc cgagcgcctg ccgtagctct tcgccgcttg agaaggagac    720
gtgaagcagc tggaacaaac cctttggaac accgggcagc ttaaagttgg ccaagtagga    780
gttgagcaac gacgaggttc ccgtgtagat tacattgtta atgttggtac tattgtgcca    840
caaataggcc gccgttccga gcgacaagag agctatcgag acccatcgaa cctcaaattc    900
caagaccggg accccggcca gcgttccttg tctagccctg gtcgcccaga gcttccgcca    960
cgccgcttcc ccattgcaac actgatctgg ggtgcgctaa caggcgataa ttctttctag   1020
gcgtcctatt ggcgtgaccc gggagagaag tcactctccc atgccctcat cgcgttccta   1080
ctacggagta ctccgtagta gctgcccatt ccaggtcggc tattttgggt ccagacgtgc   1140
cgctgccttc ttcttccgct cttccttctt ccttcccccc ttcccagcc gtagctcaca    1200 ccacacatcc ggcctgactg gcatttctct gccatactaa ttaacactat cccaacttct   1260
ccacggtcgt tcatctttgg tttttcattc tcaactagac taattaatta ccgcatcggc   1320
gcagccaatt cacttaggca agctttggta agtcgcccct gtctgctttg cagagtttcc   1380
ccggcctttt ctccttgtga caatccggtc ccgaatgggt ttgttctcaa gtgcattgac   1440
```

```
tcaccgccga aagtcgttca tagcactcgc tttagatatc aagcataaat ccggtccaca    1500
```

<210> SEQ ID NO 2
<211> LENGTH: 1000
<212> TYPE: DNA
<213> ORGANISM: Artificial sequence
<220> FEATURE:
<223> OTHER INFORMATION: Synthetic oligonucleotide

<400> SEQUENCE: 2

```
cttttacact agaactagat ttctgcaaaa gctcttgtgc aaggctgcat acagatacac      60
tagagtaagg tgcttagcta atatactaaa gcgtattagt cccaatccca tgcaagctgc     120
gagaggtcgc aatttcccga ctcggcgccg catgcgctag tgtggactgg gaatcgcggc     180
cgagcgcctg ccgtagctct tcgccgcttg agaaggagac gtgaagcagc tggaacaaac     240
cctttggaac accgggcagc ttaaagttgg ccaagtagga gttgagcaac gacgaggttc     300
ccgtgtagat tacattgtta atgttggtac tattgtgcca caaataggcc gccgttccga     360
gcgacaagag agctatcgag acccatcgaa cctcaaattc caagaccggg accccggcca     420
gcgttccttg tctagccctg gtcgcccaga gcttccgcca cgccgcttcc ccattgcaac     480
actgatctgg ggtgcgctaa caggcgataa ttctttctag gcgtcctatt ggcgtgaccc     540
gggagagaag tcactctccc atgccctcat cgcgttccta ctacggagta ctccgtagta     600
gctgcccatt ccaggtcggc tattttgggt ccagacgtgc cgctgccttc ttcttccgct     660
cttccttctt ccttccccc  ttccccagcc gtagctcaca ccacacatcc ggcctgactg     720
gcatttctct gccatactaa ttaacactat cccaacttct ccacggtcgt tcatctttgg     780
ttttcattc tcaactagac taattaatta ccgcatcggc gcagccaatt cacttaggca     840
agctttggta agtcgcccct gtctgctttg cagagtttcc ccggccttt  ctccttgtga     900
caatccggtc ccgaatgggt tgttctcaa  gtgcattgac tcaccgccga aagtcgttca     960
tagcactcgc tttagatatc aagcataaat ccggtccaca                         1000
```

<210> SEQ ID NO 3
<211> LENGTH: 700
<212> TYPE: DNA
<213> ORGANISM: Artificial sequence
<220> FEATURE:
<223> OTHER INFORMATION: Synthetic oligonucleotide

<400> SEQUENCE: 3

```
ccgtgtagat tacattgtta atgttggtac tattgtgcca caaataggcc gccgttccga      60
gcgacaagag agctatcgag acccatcgaa cctcaaattc caagaccggg accccggcca     120
gcgttccttg tctagccctg gtcgcccaga gcttccgcca cgccgcttcc ccattgcaac     180
actgatctgg ggtgcgctaa caggcgataa ttctttctag gcgtcctatt ggcgtgaccc     240
gggagagaag tcactctccc atgccctcat cgcgttccta ctacggagta ctccgtagta     300
gctgcccatt ccaggtcggc tattttgggt ccagacgtgc cgctgccttc ttcttccgct     360
cttccttctt ccttccccc  ttccccagcc gtagctcaca ccacacatcc ggcctgactg     420
gcatttctct gccatactaa ttaacactat cccaacttct ccacggtcgt tcatctttgg     480
ttttcattc tcaactagac taattaatta ccgcatcggc gcagccaatt cacttaggca     540
agctttggta agtcgcccct gtctgctttg cagagtttcc ccggccttt  ctccttgtga     600
caatccggtc ccgaatgggt tgttctcaa  gtgcattgac tcaccgccga aagtcgttca     660
```
tagcactcgc tttagatatc aagcataaat ccggtccaca                    700

<210> SEQ ID NO 4
<211> LENGTH: 560
<212> TYPE: DNA
<213> ORGANISM: Artificial sequence
<220> FEATURE:
<223> OTHER INFORMATION: Synthetic oligonucleotide

<400> SEQUENCE: 4
agctatcgag acccatcgaa cctcaaattc caagaccggg accccggcca gcgttccttg     60
tctagccctg gtcgcccaga gcttccgcca cgccgcttcc ccattgcaac actgatctgg    120
ggtgcgctaa caggcgataa ttctttctag gcgtcctatt ggcgtgaccc gggagagaag    180
tcactctccc atgccctcat cgcgttccta ctacggagta ctccgtagta gctgcccatt    240
ccaggtcggc tattttgggt ccagacgtgc cgctgccttc ttcttccgct cttccttctt    300 ccttccccc ttccccagcc gtagctcaca ccacacatcc ggcctgactg gcatttctct    360
gccatactaa ttaacactat cccaacttct ccacggtcgt tcatctttgg ttttcattc    420 tcaactagac taattaatta ccgcatcggc gcagccaatt cacttaggca agctttggta    480
agtcgcccct gtctgctttg cagagtttcc ccggccttt ctccttgtga caatccggtc    540
ccgaatgggt ttgttctcaa                                             560

<210> SEQ ID NO 5
<211> LENGTH: 490
<212> TYPE: DNA
<213> ORGANISM: Artificial sequence
<220> FEATURE:
<223> OTHER INFORMATION: Synthetic oligonucleotide

<400> SEQUENCE: 5
gtcgcccaga gcttccgcca cgccgcttcc ccattgcaac actgatctgg ggtgcgctaa     60
caggcgataa ttctttctag gcgtcctatt ggcgtgaccc gggagagaag tcactctccc    120
atgccctcat cgcgttccta ctacggagta ctccgtagta gctgcccatt ccaggtcggc    180
tattttgggt ccagacgtgc cgctgccttc ttcttccgct cttccttctt ccttccccc    240 ttccccagcc gtagctcaca ccacacatcc ggcctgactg gcatttctct gccatactaa    300
ttaacactat cccaacttct ccacggtcgt tcatctttgg ttttcattc tcaactagac    360 taattaatta ccgcatcggc gcagccaatt cacttaggca agctttggta agtcgcccct    420
gtctgctttg cagagtttcc ccggccttt ctccttgtga caatccggtc ccgaatgggt    480
ttgttctcaa                                                        490

<210> SEQ ID NO 6
<211> LENGTH: 450
<212> TYPE: DNA
<213> ORGANISM: Artificial sequence
<220> FEATURE:
<223> OTHER INFORMATION: Synthetic oligonucleotide

<400> SEQUENCE: 6
cgccgcttcc ccattgcaac actgatctgg ggtgcgctaa caggcgataa ttctttctag     60
gcgtcctatt ggcgtgaccc gggagagaag tcactctccc atgccctcat cgcgttccta    120
ctacggagta ctccgtagta gctgcccatt ccaggtcggc tattttgggt ccagacgtgc    180
cgctgccttc ttcttccgct cttccttctt ccttccccc ttccccagcc gtagctcaca    240
ccacacatcc ggcctgactg gcatttctct gccatactaa ttaacactat cccaacttct    300

| ccacggtcgt tcatctttgg tttttcattc tcaactagac taattaatta ccgcatcggc | 360 |
| gcagccaatt cacttaggca agctttggta agtcgcccct gtctgctttg cagagtttcc | 420 |
| ccggcctttt ctccttgtga caatccggtc | 450 |

<210> SEQ ID NO 7
<211> LENGTH: 400
<212> TYPE: DNA
<213> ORGANISM: Artificial sequence
<220> FEATURE:
<223> OTHER INFORMATION: Synthetic oligonucleotide

<400> SEQUENCE: 7

| caggcgataa ttctttctag gcgtcctatt ggcgtgaccc gggagagaag tcactctccc | 60 |
| atgccctcat gcgttccta ctacggagta ctccgtagta gctgcccatt ccaggtcggc | 120 |
| tattttgggt ccagacgtgc cgctgccttc ttcttccgct cttccttctt ccttcccccc | 180 |
| ttccccagcc gtagctcaca ccacacatcc ggcctgactg gcatttctct gccatactaa | 240 |
| ttaacactat cccaacttct ccacggtcgt tcatctttgg tttttcattc tcaactagac | 300 |
| taattaatta ccgcatcggc gcagccaatt cacttaggca agctttggta agtcgcccct | 360 |
| gtctgctttg cagagtttcc ccggcctttt ctccttgtga | 400 |

<210> SEQ ID NO 8
<211> LENGTH: 250
<212> TYPE: DNA
<213> ORGANISM: Artificial sequence
<220> FEATURE:
<223> OTHER INFORMATION: Synthetic oligonucleotide

<400> SEQUENCE: 8

| cttccttctt ccttcccccc ttccccagcc gtagctcaca ccacacatcc ggcctgactg | 60 |
| gcatttctct gccatactaa ttaacactat cccaacttct ccacggtcgt tcatctttgg | 120 |
| tttttcattc tcaactagac taattaatta ccgcatcggc gcagccaatt cacttaggca | 180 |
| agctttggta agtcgcccct gtctgctttg cagagtttcc ccggcctttt ctccttgtga | 240 |
| caatccggtc | 250 |

<210> SEQ ID NO 9
<211> LENGTH: 1500
<212> TYPE: DNA
<213> ORGANISM: Artificial sequence
<220> FEATURE:
<223> OTHER INFORMATION: Synthetic oligonucleotide

<400> SEQUENCE: 9

| acaggcttgt taaaggaagt cttcacggtc ggcatacaaa tcggccaaga cgttgaagat | 60 |
| gccataatac ataatatgta tgtacaataa ccgggcacat acggtgcaac tgctagtcag | 120 |
| caattgcgcc tcgcttttg acacagaggg caatgcagaa cgtcgaatcg accgagtcag | 180 |
| ttgctgttgg cgtcatgatg gctctagggt cagacagaag gtcagagaaa gcatgcctta | 240 |
| gctcgaagcc gctcagatgt aattacgcaa cgctcggcgt tcgagtttac ggaggacgac | 300 |
| ggctacaaga tggggctgct taaagttacc ttaaatagaa aatagtgcct ggcttaagag | 360 |
| atcatgtccg cggggctagc aaggatgtcg ggtcttaact cgacggctcg cctagatttc | 420 |
| gtgaaaaggg aactcactcc ccgacaggcc cgcaagtgaa tatgtaatta ctcaatggaa | 480 |
| gttctcgaaa cggagtccag aaatgatgtg gttctgtggg aatgcggcaa gaggcgacgt | 540 |

```
tgccgtgaat gcgtgaacat tcccgcctct tcttcttctc gtcttcttcc ttcttcttct    600
ttcgggtcgc ggatggttga cggccagcgt gcgcacggct gcgtgttatc gagcgtcggt    660
acgtctagcc aacatcccgt agacacgacg accaagcgtc ttgagaatgc aacaacgtct    720
cggaacctgg cacgcatctt ccgccgcagg tcggcagacg ccgcctgggc aataccaccc    780
ctgtccaggc cctttccccg caggcagagc gcgctcttc ctttcatggt tattcaggaa     840
cgtggcttcc gagattctcg cctgttctcc cccagtcaac ctgccgaccg taacccggtt    900
ccaccaccgc ggactgtccg caaaacctgg ttcgcccgag attaatatgc tatttccgga    960
ctaagtgcac aacacacaag cacccctt cc gcctcgcgct ctagaatctg ctttctaacc    1020
cggttctcgg gcccttccct ttcgcgacgc ctccgctctc cttaccaggc accatccgca    1080
ataggtaagg tagccaaccg ttttggagcg tgattctgcc aaggaccgca tccttgcatt    1140
cgccatctgg tcaaggaccc ctctttcccg ctccattctg gtggctctat cgggacggcg    1200
ttccccatgg ctctccagga gagtgatgtg cgagtctgga gagccggggt tggcgtcacg    1260
atgctgccca cctagggccg gccagcccgg cactgcgctc ccgttgatcc gtctatcccc    1320
gtcaagagca ccagccccgg cgctcgtgaa ttttcgactt gttcgacttg ctacaggtga    1380
taaagaggat gcacgccgcc ctcgatcggc ctgtgtggtt tctctccctc gtgccaaacc    1440
actcccacct cccgccccga gatagttgct tgtttcgctc cgtgagaggg acacacacca    1500

<210> SEQ ID NO 10
<211> LENGTH: 1000
<212> TYPE: DNA
<213> ORGANISM: Artificial sequence
<220> FEATURE:
<223> OTHER INFORMATION: Synthetic oligonucleotide

<400> SEQUENCE: 10
aaatgatgtg gttctgtggg aatgcggcaa gaggcgacgt tgccgtgaat gcgtgaacat     60
tcccgcctct tcttcttctc gtcttcttcc ttcttcttct ttcgggtcgc ggatggttga   120
cggccagcgt gcgcacggct gcgtgttatc gagcgtcggt acgtctagcc aacatcccgt   180
agacacgacg accaagcgtc ttgagaatgc aacaacgtct cggaacctgg cacgcatctt   240
ccgccgcagg tcggcagacg ccgcctgggc aataccaccc ctgtccaggc cctttccccg   300
caggcagagc gcgctcttc ctttcatggt tattcaggaa cgtggcttcc gagattctcg    360
cctgttctcc cccagtcaac ctgccgaccg taacccggtt ccaccaccgc ggactgtccg   420
caaaacctgg ttcgcccgag attaatatgc tatttccgga ctaagtgcac aacacacaag   480 cacccctt cc gcctcgcgct ctagaatctg ctttctaacc cggttctcgg gcccttccct   540
ttcgcgacgc ctccgctctc cttaccaggc accatccgca ataggtaagg tagccaaccg   600
ttttggagcg tgattctgcc aaggaccgca tccttgcatt cgccatctgg tcaaggaccc   660
ctctttcccg ctccattctg gtggctctat cgggacggcg ttccccatgg ctctccagga   720
gagtgatgtg cgagtctgga gagccggggt tggcgtcacg atgctgccca cctagggccg   780
gccagcccgg cactgcgctc ccgttgatcc gtctatcccc gtcaagagca ccagccccgg   840
cgctcgtgaa ttttcgactt gttcgacttg ctacaggtga taaagaggat gcacgccgcc   900
ctcgatcggc ctgtgtggtt tctctccctc gtgccaaacc actcccacct cccgccccga   960
gatagttgct tgtttcgctc cgtgagaggg acacacacca                         1000

<210> SEQ ID NO 11
<211> LENGTH: 700
```

```
<212> TYPE: DNA
<213> ORGANISM: Artificial sequence
<220> FEATURE:
<223> OTHER INFORMATION: Synthetic oligonucleotide

<400> SEQUENCE: 11
caggcagagc cgcgctcttc ctttcatggt tattcaggaa cgtggcttcc gagattctcg      60
cctgttctcc cccagtcaac ctgccgaccg taacccggtt ccaccaccgc ggactgtccg     120
caaaacctgg ttcgcccgag attaatatgc tatttccgga ctaagtgcac aacacacaag     180
caccccttcc gcctcgcgct ctagaatctg ctttctaacc cggttctcgg gcccttccct     240
ttcgcgacgc ctccgctctc cttaccaggc accatccgca ataggtaagg tagccaaccg     300
ttttggagcg tgattctgcc aaggaccgca tccttgcatt cgccatctgg tcaaggaccc     360
ctctttcccg ctccattctg gtggctctat cgggacggcg ttccccatgg ctctccagga     420
gagtgatgtg cgagtctgga gagccggggt tggcgtcacg atgctgccca cctagggccg     480
gccagcccgg cactgcgctc ccgttgatcc gtctatcccc gtcaagagca ccagcccgg      540
cgctcgtgaa ttttcgactt gttcgacttg ctacaggtga taaagaggat gcacgccgcc     600
ctcgatcggc ctgtgtggtt tctctccctc gtgccaaacc actcccacct cccgccccga     660
gatagttgct tgtttcgctc cgtgagaggg acacacacca                           700

<210> SEQ ID NO 12
<211> LENGTH: 560
<212> TYPE: DNA
<213> ORGANISM: Artificial sequence
<220> FEATURE:
<223> OTHER INFORMATION: Synthetic oligonucleotide

<400> SEQUENCE: 12
cccagtcaac ctgccgaccg taacccggtt ccaccaccgc ggactgtccg caaaacctgg      60
ttcgcccgag attaatatgc tatttccgga ctaagtgcac aacacacaag caccccttcc     120
gcctcgcgct ctagaatctg ctttctaacc cggttctcgg gcccttccct ttcgcgacgc     180
ctccgctctc cttaccaggc accatccgca ataggtaagg tagccaaccg ttttggagcg     240
tgattctgcc aaggaccgca tccttgcatt cgccatctgg tcaaggaccc ctctttcccg     300
ctccattctg gtggctctat cgggacggcg ttccccatgg ctctccagga gagtgatgtg     360
cgagtctgga gagccggggt tggcgtcacg atgctgccca cctagggccg gccagcccgg     420
cactgcgctc ccgttgatcc gtctatcccc gtcaagagca ccagcccgg cgctcgtgaa      480
ttttcgactt gttcgacttg ctacaggtga taaagaggat gcacgccgcc ctcgatcggc     540
ctgtgtggtt tctctccctc                                                560

<210> SEQ ID NO 13
<211> LENGTH: 490
<212> TYPE: DNA
<213> ORGANISM: Artificial sequence
<220> FEATURE:
<223> OTHER INFORMATION: Synthetic oligonucleotide

<400> SEQUENCE: 13
attaatatgc tatttccgga ctaagtgcac aacacacaag caccccttcc gcctcgcgct      60
ctagaatctg ctttctaacc cggttctcgg gcccttccct ttcgcgacgc ctccgctctc     120
cttaccaggc accatccgca ataggtaagg tagccaaccg ttttggagcg tgattctgcc     180
aaggaccgca tccttgcatt cgccatctgg tcaaggaccc ctctttcccg ctccattctg     240
```

```
gtggctctat cgggacggcg ttccccatgg ctctccagga gagtgatgtg cgagtctgga    300
gagccggggt tggcgtcacg atgctgccca cctagggccg gccagcccgg cactgcgctc    360
ccgttgatcc gtctatcccc gtcaagagca ccagccccgg cgctcgtgaa ttttcgactt    420
gttcgacttg ctacaggtga taaagaggat gcacgccgcc ctcgatcggc ctgtgtggtt    480
tctctccctc                                                           490

<210> SEQ ID NO 14
<211> LENGTH: 450
<212> TYPE: DNA
<213> ORGANISM: Artificial sequence
<220> FEATURE:
<223> OTHER INFORMATION: Synthetic oligonucleotide

<400> SEQUENCE: 14
ctagaatctg ctttctaacc cggttctcgg gcccttccct ttcgcgacgc ctccgctctc     60
cttaccaggc accatccgca ataggtaagg tagccaaccg ttttggagcg tgattctgcc    120
aaggaccgca tccttgcatt cgccatctgg tcaaggaccc ctctttcccg ctccattctg    180
gtggctctat cgggacggcg ttccccatgg ctctccagga gagtgatgtg cgagtctgga    240
gagccggggt tggcgtcacg atgctgccca cctagggccg gccagcccgg cactgcgctc    300
ccgttgatcc gtctatcccc gtcaagagca ccagccccgg cgctcgtgaa ttttcgactt    360
gttcgacttg ctacaggtga taaagaggat gcacgccgcc ctcgatcggc ctgtgtggtt    420
tctctccctc gtgccaaacc actcccacct                                    450

<210> SEQ ID NO 15
<211> LENGTH: 400
<212> TYPE: DNA
<213> ORGANISM: Artificial sequence
<220> FEATURE:
<223> OTHER INFORMATION: Synthetic oligonucleotide

<400> SEQUENCE: 15
ctagaatctg ctttctaacc cggttctcgg gcccttccct ttcgcgacgc ctccgctctc     60
cttaccaggc accatccgca ataggtaagg tagccaaccg ttttggagcg tgattctgcc    120
aaggaccgca tccttgcatt cgccatctgg tcaaggaccc ctctttcccg ctccattctg    180
gtggctctat cgggacggcg ttccccatgg ctctccagga gagtgatgtg cgagtctgga    240
gagccggggt tggcgtcacg atgctgccca cctagggccg gccagcccgg cactgcgctc    300
ccgttgatcc gtctatcccc gtcaagagca ccagccccgg cgctcgtgaa ttttcgactt    360
gttcgacttg ctacaggtga taaagaggat gcacgccgcc                          400

<210> SEQ ID NO 16
<211> LENGTH: 250
<212> TYPE: DNA
<213> ORGANISM: Artificial sequence
<220> FEATURE:
<223> OTHER INFORMATION: Synthetic oligonucleotide

<400> SEQUENCE: 16
ttccccatgg ctctccagga gagtgatgtg cgagtctgga gagccggggt tggcgtcacg     60
atgctgccca cctagggccg gccagcccgg cactgcgctc ccgttgatcc gtctatcccc    120
gtcaagagca ccagccccgg cgctcgtgaa ttttcgactt gttcgacttg ctacaggtga    180
taaagaggat gcacgccgcc ctcgatcggc ctgtgtggtt tctctccctc gtgccaaacc    240
actcccacct                                                           250
```

<210> SEQ ID NO 17
<211> LENGTH: 1500
<212> TYPE: DNA
<213> ORGANISM: Artificial sequence
<220> FEATURE:
<223> OTHER INFORMATION: Synthetic oligonucleotide

<400> SEQUENCE: 17

```
atgcgctccg ccttgtgcgc ctcgtgcagc cgcagcacct cgatcagcac gcgcaccgag    60
ccgatcgggt ggtacaggta ctcggacgcc ggcgggagca tgtcggcgaa gggggacgtc   120
ctctggaacg agagggcgaa cgtgtagatg ccagccccg tgagcgtgcc ctgttgtttt    180
gttttttttgt tttgttttgt ttcccgtggt tagaggaggt ttttttcgtt ttagaatggg   240
aaggaagaaa ggaaagaagg aaactttggg gccgggtaat gagggaggga aacgtacgac   300
ggtgatgaca acatggatcc agcggctatg caggaaccag tgggcgaacg tgtttggcgg   360
cggcggcagg cccgggtagt cgcgggaggc ttgcgcgctg gcctcctcga agctgaggtc   420
gccgccgtag tggcgcggga tgctcttctt cggcaggcgg gagccgtgtg aggggggatt   480
gaagcgctcc ggcttggcga gcacccgctg gccggacgga gtgccggcgt tgctgctgct   540
gctgctgctg ctgctgttcc tggcgagccg caggaatacg cggctccggg tcgagacgga   600
ggccggagcc gaggccgccg gagccgcccg gcgccatatc aggccggtct gcgggaggag   660
gaagcggggg atgatgggtg ctgctggtgc cggcgtcatg actactataa ctaactgccg   720
ccgcgcgtgt ccgcacaaat ttcgagtgag cgaggaatga attcggattg aggtaatccg   780
tagtgtacga gcgagatccc tcgaaacgag gggaggcaat caaagattct ttgtctcctc   840
tctcctccct ctttttttt gcttatcccc ggttcctctc ggcgacagaa atgcaactcg   900
gttttctgg gtgcccgatc gggggtccct cggcgtcggg gcaacaaggc aattcgcagg   960
gtcgcggacg ttgcggtgcg gctcaatcag gcgatatgcg agtggtcaga aaattcgcct  1020
gcgtcaagtt gctgcaggtt tctgctgcta tcccattccg gctagcgctt ctcttctgct  1080
gtgcagtact ccgtacacta tagtagctcg cggtcctcgg gccaaggcgc gtctttgggt  1140
tgcccggggg ggggggtggc ggcgcgccaa cagtgccggt cgctcccgaa tttgcccggg  1200
gcgactgact aacagtcgaa acatgattgg cacaagttag aaaataggtg ggtcattttt  1260
ccacggatta ccatggctcg ctcgttggat gatcaaggct tggcagtgtt catcgatgca  1320
aaaaatccgg cgcgcggacc tggcacggcg attgcagcaa actaacacct cattccgaaa  1380
tttttcttga actctttcct acttcccttc acatccgacc ttgcttcgca atatctgctc  1440
ttcctcacca acaccgactc ctctcagaca ctcaatcctc tcactacccc aaccgtcaag  1500
```

<210> SEQ ID NO 18
<211> LENGTH: 1000
<212> TYPE: DNA
<213> ORGANISM: Artificial sequence
<220> FEATURE:
<223> OTHER INFORMATION: Synthetic oligonucleotide

<400> SEQUENCE: 18

```
gcacccgctg gccggacgga gtgccggcgt tgctgctgct gctgctgctg ctgctgttcc    60
tggcgagccg caggaatacg cggctccggg tcgagacgga ggccggagcc gaggccgccg   120
gagccgcccg gcgccatatc aggccggtct gcgggaggag gaagcggggg atgatgggtg   180
ctgctggtgc cggcgtcatg actactataa ctaactgccg ccgcgcgtgt ccgcacaaat   240
```

| | |
|---|---|
| ttcgagtgag cgaggaatga attcggattg aggtaatccg tagtgtacga gcgagatccc | 300 |
| tcgaaacgag gggaggcaat caaagattct tgtctcctc tctcctccct cttttttttt | 360 |
| gcttatcccc ggttcctctc ggcgacagaa atgcaactcg gttttctgg gtgcccgatc | 420 |
| gggggtccct cggcgtcggg gcaacaaggc aattcgcagg gtcgcggacg ttgcggtgcg | 480 |
| gctcaatcag gcgatatgcg agtggtcaga aaattcgcct gcgtcaagtt gctgcaggtt | 540 |
| tctgctgcta tcccattccg gctagcgctt ctcttctgct gtgcagtact ccgtacacta | 600 |
| tagtagctcg cggtcctcgg gccaaggcgc gtctttgggt tgcccggggg gggggtggc | 660 |
| ggcgcgccaa cagtgccggt cgctcccgaa tttgcccggg gcgactgact aacagtcgaa | 720 |
| acatgattgg cacaagttag aaaataggtg ggtcatttt ccacggatta ccatggctcg | 780 |
| ctcgttggat gatcaaggct tggcagtgtt catcgatgca aaaaatccgg cgcgcggacc | 840 |
| tggcacggcg attgcagcaa actaacacct cattccgaaa ttttttcttga actctttcct | 900 |
| acttcccttc acatccgacc ttgcttcgca atatctgctc ttcctcacca acaccgactc | 960 |
| ctctcagaca ctcaatcctc tcactacccc aaccgtcaag | 1000 |

<210> SEQ ID NO 19
<211> LENGTH: 700
<212> TYPE: DNA
<213> ORGANISM: Artificial sequence
<220> FEATURE:
<223> OTHER INFORMATION: Synthetic oligonucleotide

<400> SEQUENCE: 19

| | |
|---|---|
| tcgaaacgag gggaggcaat caaagattct tgtctcctc tctcctccct cttttttttt | 60 |
| gcttatcccc ggttcctctc ggcgacagaa atgcaactcg gttttctgg gtgcccgatc | 120 |
| gggggtccct cggcgtcggg gcaacaaggc aattcgcagg gtcgcggacg ttgcggtgcg | 180 |
| gctcaatcag gcgatatgcg agtggtcaga aaattcgcct gcgtcaagtt gctgcaggtt | 240 |
| tctgctgcta tcccattccg gctagcgctt ctcttctgct gtgcagtact ccgtacacta | 300 |
| tagtagctcg cggtcctcgg gccaaggcgc gtctttgggt tgcccggggg gggggtggc | 360 |
| ggcgcgccaa cagtgccggt cgctcccgaa tttgcccggg gcgactgact aacagtcgaa | 420 |
| acatgattgg cacaagttag aaaataggtg ggtcatttt ccacggatta ccatggctcg | 480 |
| ctcgttggat gatcaaggct tggcagtgtt catcgatgca aaaaatccgg cgcgcggacc | 540 |
| tggcacggcg attgcagcaa actaacacct cattccgaaa ttttttcttga actctttcct | 600 |
| acttcccttc acatccgacc ttgcttcgca atatctgctc ttcctcacca acaccgactc | 660 |
| ctctcagaca ctcaatcctc tcactacccc aaccgtcaag | 700 |

<210> SEQ ID NO 20
<211> LENGTH: 560
<212> TYPE: DNA
<213> ORGANISM: Artificial sequence
<220> FEATURE:
<223> OTHER INFORMATION: Synthetic oligonucleotide

<400> SEQUENCE: 20

| | |
|---|---|
| ggttcctctc ggcgacagaa atgcaactcg gttttctgg gtgcccgatc gggggtccct | 60 |
| cggcgtcggg gcaacaaggc aattcgcagg gtcgcggacg ttgcggtgcg gctcaatcag | 120 |
| gcgatatgcg agtggtcaga aaattcgcct gcgtcaagtt gctgcaggtt tctgctgcta | 180 |
| tcccattccg gctagcgctt ctcttctgct gtgcagtact ccgtacacta tagtagctcg | 240 |
| cggtcctcgg gccaaggcgc gtctttgggt tgcccggggg gggggtggc ggcgcgccaa | 300 |

```
cagtgccggt cgctcccgaa tttgcccggg gcgactgact aacagtcgaa acatgattgg    360
cacaagttag aaaataggtg ggtcattttt ccacggatta ccatggctcg ctcgttggat    420
gatcaaggct tggcagtgtt catcgatgca aaaaatccgg cgcgcggacc tggcacggcg    480
attgcagcaa actaacacct cattccgaaa ttttctcttga actctttcct acttcccttc    540
acatccgacc ttgcttcgca                                                560

<210> SEQ ID NO 21
<211> LENGTH: 490
<212> TYPE: DNA
<213> ORGANISM: Artificial sequence
<220> FEATURE:
<223> OTHER INFORMATION: Synthetic oligonucleotide

<400> SEQUENCE: 21
gcaacaaggc aattcgcagg gtcgcggacg ttgcggtgcg gctcaatcag gcgatatgcg     60
agtggtcaga aaattcgcct gcgtcaagtt gctgcaggtt tctgctgcta tcccattccg    120
gctagcgctt ctcttctgct gtgcagtact ccgtacacta tagtagctcg cggtcctcgg    180
gccaaggcgc gtctttgggt tgcccggggg gggggtggc ggcgcgccaa cagtgccggt     240
cgctcccgaa tttgcccggg gcgactgact aacagtcgaa acatgattgg cacaagttag    300
aaaataggtg ggtcattttt ccacggatta ccatggctcg ctcgttggat gatcaaggct    360
tggcagtgtt catcgatgca aaaaatccgg cgcgcggacc tggcacggcg attgcagcaa    420
actaacacct cattccgaaa ttttctcttga actctttcct acttcccttc acatccgacc    480
ttgcttcgca                                                           490

<210> SEQ ID NO 22
<211> LENGTH: 450
<212> TYPE: DNA
<213> ORGANISM: Artificial sequence
<220> FEATURE:
<223> OTHER INFORMATION: Synthetic oligonucleotide

<400> SEQUENCE: 22
agtggtcaga aaattcgcct gcgtcaagtt gctgcaggtt tctgctgcta tcccattccg     60
gctagcgctt ctcttctgct gtgcagtact ccgtacacta tagtagctcg cggtcctcgg    120
gccaaggcgc gtctttgggt tgcccggggg gggggtggc ggcgcgccaa cagtgccggt     180
cgctcccgaa tttgcccggg gcgactgact aacagtcgaa acatgattgg cacaagttag    240
aaaataggtg ggtcattttt ccacggatta ccatggctcg ctcgttggat gatcaaggct    300
tggcagtgtt catcgatgca aaaaatccgg cgcgcggacc tggcacggcg attgcagcaa    360
actaacacct cattccgaaa ttttctcttga actctttcct acttcccttc acatccgacc    420
ttgcttcgca atatctgctc ttcctcacca                                     450

<210> SEQ ID NO 23
<211> LENGTH: 400
<212> TYPE: DNA
<213> ORGANISM: Artificial sequence
<220> FEATURE:
<223> OTHER INFORMATION: Synthetic oligonucleotide

<400> SEQUENCE: 23
agtggtcaga aaattcgcct gcgtcaagtt gctgcaggtt tctgctgcta tcccattccg     60
gctagcgctt ctcttctgct gtgcagtact ccgtacacta tagtagctcg cggtcctcgg    120
```

```
gccaaggcgc gtctttgggt tgcccggggg gggggtggc ggcgcgccaa cagtgccggt        180
cgctcccgaa tttgcccggg gcgactgact aacagtcgaa acatgattgg cacaagttag        240
aaaataggtg ggtcattttt ccacggatta ccatggctcg ctcgttggat gatcaaggct        300
tggcagtgtt catcgatgca aaaaatccgg cgcgcggacc tggcacggcg attgcagcaa        360
actaacacct cattccgaaa ttttcttga actctttcct                               400
```

<210> SEQ ID NO 24  
<211> LENGTH: 250  
<212> TYPE: DNA  
<213> ORGANISM: Artificial sequence  
<220> FEATURE:  
<223> OTHER INFORMATION: Synthetic oligonucleotide

<400> SEQUENCE: 24

```
gcgactgact aacagtcgaa acatgattgg cacaagttag aaaataggtg ggtcattttt        60
ccacggatta ccatggctcg ctcgttggat gatcaaggct tggcagtgtt catcgatgca       120
aaaaatccgg cgcgcggacc tggcacggcg attgcagcaa actaacacct cattccgaaa       180 ttttcttga actctttcct acttcccttc acatccgacc ttgcttcgca atatctgctc        240
ttcctcacca                                                              250
```

<210> SEQ ID NO 25  
<211> LENGTH: 1500  
<212> TYPE: DNA  
<213> ORGANISM: Artificial sequence  
<220> FEATURE:  
<223> OTHER INFORMATION: Synthetic oligonucleotide

<400> SEQUENCE: 25

```
gctcgaggat gtcaaagtcc acatttcatt tttttctttt tcttttttt ttttccggat         60 aggcatcttc catttgggaa tcatagatgt ctgcttacgg ggcggtgtgc gagccgtggt       120
gctcggcttt tgggggtaag aatggcccat gacggagcga tggcggtttt agttcaaggt       180
gctcgtgtcc tgatgataga tgatattggt gtgacgtggt gtgttctgca gattttgaa        240 gcttgggga tgtaactcgg cccaagagga aagtgcggag atgtgtgctc aatcgaggta       300
cttaatgttc cgtattcttt cctcctcagg ctattatctc gtgcagtggc gaatctgaag       360
agtgtcacgg gtacttcgta ggtaccaaag cttcaccgtc tttggacacg tcgatagcga      420
cgtacctgca gcagtggtct gatgtgtctg aaatttgtct tgattcccga tggcgacagg      480
tgtctgttat gagaacctac ctgaccgaga gtggccaggc aagagaacca atagctatat     540
tttcaaactc gctatttcaa gcttgacctc gaaatggaaa accgactatc agcagtgaca      600
atcaatcacg ggccagagtg cattaaatgg atgtactgtg ggatgcggaa agcgaactat      660
agtatcttcg tttaactgct actgctgctg gtaagtggtg gtcgaaggaa gcgaaggctg      720
actggggcca ccgtgcagga agatatgggt ggctgtaacc ctggtggggc gggagccct       780 agtgggccc gaccaccaca gtatgtact gtgtacgtcc gtatatacgg attacataca       840
tacctacaca gtataattat ctgcgcattg atttccggag aaactactcc gtacctaggt      900
atacagaaaa gaaccgccaa cgaaaagtaa ttaattacgt acgcatcacg actcgcactc      960
ctttccagcg tacaaggatt gttttgattc cctttgagga tgacattcat tccacgatac     1020
caatgagata gcgggtttgg acattttga ctcgaacgga aatgatgaac agcaagcagt     1080
attagtcggc tctcacacgc acactggcat caagcagcaa tcgaacactt gccgactcaa     1140
cgcatcatga cggcaaaaac ccacgtgggc atgatgtcca agtccctata ttcaggaacc     1200
```

```
cccccggacca gatgacgcat ggtacggtac ctatgtgaca tcaggctcgc caccagttgt    1260
ctgttcccta ttataatccg cctattaatt aattagtagc tctgatttgt aaaagtgcaa    1320
gcctgttctg atcatcttca tgacctctac tctgcaagtc cgaacaagag atcaccatca    1380
attgcatatt atttgataat taatacactg tatctgtaca agaacagca caaacatat     1440 ttttctcctg aataattatt actactcccc cagacccaaa caaaaaagtc taattacacc    1500

<210> SEQ ID NO 26
<211> LENGTH: 1000
<212> TYPE: DNA
<213> ORGANISM: Artificial sequence
<220> FEATURE:
<223> OTHER INFORMATION: Synthetic oligonucleotide

<400> SEQUENCE: 26
ctgaccgaga gtggccaggc aagagaacca atagctatat tttcaaactc gctatttcaa      60
gcttgacctc gaaatggaaa accgactatc agcagtgaca tcaatcacg ggccagagtg      120 cattaaatgg atgtactgtg ggatgcggaa agcgaactat agtatcttcg tttaactgct     180
actgctgctg gtaagtggtg gtcgaaggaa gcgaaggctg actggggcca ccgtgcagga     240
agatatgggt ggctgtaacc tggtggggc cgggagccct agtggggccc gaccaccaca     300
agtatgtact gtgtacgtcc gtatatacgg attacataca tacctacaca gtataattat     360
ctgcgcattg atttccggag aaactactcc gtacctaggt atacagaaaa gaaccgccaa     420
cgaaaagtaa ttaattacgt acgcatcacg actcgcactc ctttccagcg tacaaggatt     480
gttttgattc cctttgagga tgacattcat tccacgatac caatgagata gcgggtttgg     540 acattttga ctcgaacgga aatgatgaac agcaagcagt attagtcggc tctcacacgc      600
acactggcat caagcagcaa tcgaacactt gccgactcaa cgcatcatga cggcaaaaac     660
ccacgtgggc atgatgtcca agtccctata ttcaggaacc cccggacca gatgacgcat      720 ggtacggtac ctatgtgaca tcaggctcgc caccagttgt ctgttcccta ttataatccg     780
cctattaatt aattagtagc tctgatttgt aaaagtgcaa gcctgttctg atcatcttca    840
tgacctctac tctgcaagtc cgaacaagag atcaccatca attgcatatt atttgataat    900
taatacactg tatctgtaca agaacagca caaacatat ttttctcctg aataattatt      960
actactcccc cagacccaaa caaaaaagtc taattacacc                           1000

<210> SEQ ID NO 27
<211> LENGTH: 700
<212> TYPE: DNA
<213> ORGANISM: Artificial sequence
<220> FEATURE:
<223> OTHER INFORMATION: Synthetic oligonucleotide

<400> SEQUENCE: 27
agtatgtact gtgtacgtcc gtatatacgg attacataca tacctacaca gtataattat      60
ctgcgcattg atttccggag aaactactcc gtacctaggt atacagaaaa gaaccgccaa     120
cgaaaagtaa ttaattacgt acgcatcacg actcgcactc ctttccagcg tacaaggatt     180
gttttgattc cctttgagga tgacattcat tccacgatac caatgagata gcgggtttgg     240 acattttga ctcgaacgga aatgatgaac agcaagcagt attagtcggc tctcacacgc      300
acactggcat caagcagcaa tcgaacactt gccgactcaa cgcatcatga cggcaaaaac     360
ccacgtgggc atgatgtcca agtccctata ttcaggaacc cccggacca gatgacgcat      420
```

```
ggtacggtac ctatgtgaca tcaggctcgc caccagttgt ctgttccctg ttataatccg      480
cctattaatt aattagtagc tctgatttgt aaaagtgcaa gcctgttctg atcatcttca      540
tgacctctac tctgcaagtc cgaacaagag atcaccatca attgcatatt atttgataat      600
taatacactg tatctgtaca aagaacagca caaaacatat ttttctcctg aataattatt      660
actactcccc cagacccaaa caaaaaagtc taattacacc                            700

<210> SEQ ID NO 28
<211> LENGTH: 560
<212> TYPE: DNA
<213> ORGANISM: Artificial sequence
<220> FEATURE:
<223> OTHER INFORMATION: Synthetic oligonucleotide

<400> SEQUENCE: 28
atttccggag aaactactcc gtacctaggt atacagaaaa gaaccgccaa cgaaaagtaa       60
ttaattacgt acgcatcacg actcgcactc cttccagcg tacaaggatt gttttgattc      120
cctttgagga tgacattcat tccacgatac caatgagata gcgggtttgg acattttga      180 ctcgaacgga aatgatgaac agcaagcagt attagtcggc tctcacacgc acactggcat      240
caagcagcaa tcgaacactt gccgactcaa cgcatcatga cggcaaaaac ccacgtgggc      300
atgatgtcca agtccctata ttcaggaacc ccccggacca gatgacgcat ggtacggtac      360
ctatgtgaca tcaggctcgc caccagttgt ctgttccctg ttataatccg cctattaatt      420
aattagtagc tctgatttgt aaaagtgcaa gcctgttctg atcatcttca tgacctctac      480
tctgcaagtc cgaacaagag atcaccatca attgcatatt atttgataat taatacactg      540
tatctgtaca aagaacagca                                                  560

<210> SEQ ID NO 29
<211> LENGTH: 490
<212> TYPE: DNA
<213> ORGANISM: Artificial sequence
<220> FEATURE:
<223> OTHER INFORMATION: Synthetic oligonucleotide

<400> SEQUENCE: 29
acgcatcacg actcgcactc cttccagcg tacaaggatt gttttgattc cctttgagga       60
tgacattcat tccacgatac caatgagata gcgggtttgg acattttga ctcgaacgga      120 aatgatgaac agcaagcagt attagtcggc tctcacacgc acactggcat caagcagcaa      180
tcgaacactt gccgactcaa cgcatcatga cggcaaaaac ccacgtgggc atgatgtcca      240
agtccctata ttcaggaacc ccccggacca gatgacgcat ggtacggtac ctatgtgaca      300
tcaggctcgc caccagttgt ctgttccctg ttataatccg cctattaatt aattagtagc      360
tctgatttgt aaaagtgcaa gcctgttctg atcatcttca tgacctctac tctgcaagtc      420
cgaacaagag atcaccatca attgcatatt atttgataat taatacactg tatctgtaca      480
aagaacagca                                                             490

<210> SEQ ID NO 30
<211> LENGTH: 450
<212> TYPE: DNA
<213> ORGANISM: Artificial sequence
<220> FEATURE:
<223> OTHER INFORMATION: Synthetic oligonucleotide

<400> SEQUENCE: 30
tgacattcat tccacgatac caatgagata gcgggtttgg acattttga ctcgaacgga       60
```

```
aatgatgaac agcaagcagt attagtcggc tctcacacgc acactggcat caagcagcaa    120
tcgaacactt gccgactcaa cgcatcatga cggcaaaaac ccacgtgggc atgatgtcca    180
agtccctata ttcaggaacc ccccggacca gatgacgcat ggtacggtac ctatgtgaca    240
tcaggctcgc caccagttgt ctgttcccta ttataatccg cctattaatt aattagtagc    300
tctgatttgt aaaagtgcaa gcctgttctg atcatcttca tgacctctac tctgcaagtc    360
cgaacaagag atcaccatca attgcatatt atttgataat taatacactg tatctgtaca    420
aagaacagca caaaacatat ttttctcctg                                     450

<210> SEQ ID NO 31
<211> LENGTH: 400
<212> TYPE: DNA
<213> ORGANISM: Artificial sequence
<220> FEATURE:
<223> OTHER INFORMATION: Synthetic oligonucleotide

<400> SEQUENCE: 31
tgacattcat tccacgatac caatgagata gcgggtttgg acattttga ctcgaacgga     60 aatgatgaac agcaagcagt attagtcggc tctcacacgc acactggcat caagcagcaa    120
tcgaacactt gccgactcaa cgcatcatga cggcaaaaac ccacgtgggc atgatgtcca    180
agtccctata ttcaggaacc ccccggacca gatgacgcat ggtacggtac ctatgtgaca    240
tcaggctcgc caccagttgt ctgttcccta ttataatccg cctattaatt aattagtagc    300
tctgatttgt aaaagtgcaa gcctgttctg atcatcttca tgacctctac tctgcaagtc    360
cgaacaagag atcaccatca attgcatatt atttgataat                          400

<210> SEQ ID NO 32
<211> LENGTH: 250
<212> TYPE: DNA
<213> ORGANISM: Artificial sequence
<220> FEATURE:
<223> OTHER INFORMATION: Synthetic oligonucleotide

<400> SEQUENCE: 32
ccccggacca gatgacgcat ggtacggtac ctatgtgaca tcaggctcgc caccagttgt     60
ctgttcccta ttataatccg cctattaatt aattagtagc tctgatttgt aaaagtgcaa    120
gcctgttctg atcatcttca tgacctctac tctgcaagtc cgaacaagag atcaccatca    180
attgcatatt atttgataat taatacactg tatctgtaca aagaacagca caaaacatat    240
ttttctcctg                                                           250

<210> SEQ ID NO 33
<211> LENGTH: 1500
<212> TYPE: DNA
<213> ORGANISM: Artificial sequence
<220> FEATURE:
<223> OTHER INFORMATION: Synthetic oligonucleotide

<400> SEQUENCE: 33
ccaaccgaac ccccatcgtc gcagcccctc tcgcttttga acggctccc aagccactta      60 aacccgctag agcactctct caagccagcg cggtgggtct agcctacgta cgatacaccc    120 ccaccccaa acaaccgtga caggatacac gactcccaca acacaatgga taggatgcac    180
gatggatgaa ccgaggacgg aggcacacaa gaaatgcaat gtggcccttc tcggcggaag    240
cacacgggct gtagggagcg ggggggaaaa ggagacagac aggcgtcctt gcagcagagg    300
```

```
gtttgaagtc gacccacaca caccgatgaa gccgcctttt gcagcctctc tctcgtcatc      360
accgccctcc tcgagttcag gcagtttgcc gctttgcctc gtgcacacat agggcccggc      420 attttttcctg ggcatggaat tctggaatga agaccaggac atcaatctgc gtcgggcgag     480
gcaacgccga agagctgttg tattccggac actcgtatac tgaccctaaa cgtgtatgta      540
tgcacagtac aatgaaagat tcgaaatggg gaaaaagtag ccaatgcata cgtacgtacg      600
aaggaacgca ttgagcattc gacactagtt ctgaccttca aaaaccgtc attcgaatct       660 ggacctggct tgtcagttat ggtgtttgac tgagtgccag gtgagtcgag cactaacgaa      720
gggagtgctt taaaacccctt ccaggctgct ccagacaccc tgattctggg gctgctgcag    780
gaatcgacac ggggaagaag cagcattgtt tcagaatgta gacatcaagc gggtccggaa     840
agcacatgta tggaaagtaa gtacctccgt acggagtact gcatgtccat ccgtacttga      900
ggaaacgctg aggtaacatg gaggtagaag aaaccacgag agactatggg ttacacctgc      960
tcaaacccac tgcacctctc ctctggggat tttccgactc ttccccctgct tgaatgcaca    1020 gacagctgtg tctttggtac actttactaa agaccacagc caagcgggag aaaacgggga   1080
cgatgagtca cgtccgggag attccggcct gctgtgtcgg aagcaatcag ctgagctgct     1140
caatcctgaa ctttcagtac acggctgcca actgagttgc agcggtccga agcgttccga    1200
gtcctttgtc agttgctttt tcgcttagtt tattccttgg accagctctt gtcaaagacc    1260
gaaaatgctt tcgggagtaa gagcgcttgg gatttggggt tatgtcatag accggatgaa   1320
gtcggcctgt ggtcccttcg ttttcctgcc ttccccttga ggtggcttgc gaacaaacgt     1380
ataaatgatg tatcactctc caagacatgc ccgtactcgc cttgatgaat ctcagactcg     1440
tgatccatcg cgacaagaca gtatattggc agccatctgt ctgttgaagc tttcaacccc    1500
```

<210> SEQ ID NO 34
<211> LENGTH: 1000
<212> TYPE: DNA
<213> ORGANISM: Artificial sequence
<220> FEATURE:
<223> OTHER INFORMATION: Synthetic oligonucleotide

<400> SEQUENCE: 34

```
tattccggac actcgtatac tgaccctaaa cgtgtatgta tgcacagtac aatgaaagat      60
tcgaaatggg gaaaaagtag ccaatgcata cgtacgtacg aaggaacgca ttgagcattc    120
gacactagtt ctgaccttca aaaaccgtc attcgaatct ggacctggct tgtcagttat     180
ggtgtttgac tgagtgccag gtgagtcgag cactaacgaa gggagtgctt taaaacccctt  240 ccaggctgct ccagacaccc tgattctggg gctgctgcag gaatcgacac ggggaagaag   300
cagcattgtt tcagaatgta gacatcaagc gggtccggaa agcacatgta tggaaagtaa    360
gtacctccgt acggagtact gcatgtccat ccgtacttga ggaaacgctg aggtaacatg   420
gaggtagaag aaaccacgag agactatggg ttacacctgc tcaaacccac tgcacctctc   480
ctctggggat tttccgactc ttccccctgct tgaatgcaca gacagctgtg tctttggtac   540
actttactaa agaccacagc caagcgggag aaaacgggga cgatgagtca cgtccgggag   600
attccggcct gctgtgtcgg aagcaatcag ctgagctgct caatcctgaa ctttcagtac    660
acggctgcca actgagttgc agcggtccga agcgttccga gtcctttgtc agttgctttt    720
tcgcttagtt tattccttgg accagctctt gtcaaagacc gaaaatgctt tcgggagtaa   780
gagcgcttgg gatttggggt tatgtcatag accggatgaa gtcggcctgt ggtcccttcg    840
ttttcctgcc ttccccttga ggtggcttgc gaacaaacgt ataaatgatg tatcactctc    900
```

```
caagacatgc ccgtactcgc cttgatgaat ctcagactcg tgatccatcg cgacaagaca    960
gtatattggc agccatctgt ctgttgaagc tttcaacccc                         1000
```

<210> SEQ ID NO 35
<211> LENGTH: 700
<212> TYPE: DNA
<213> ORGANISM: Artificial sequence
<220> FEATURE:
<223> OTHER INFORMATION: Synthetic oligonucleotide

<400> SEQUENCE: 35

```
cagcattgtt tcagaatgta gacatcaagc gggtccggaa agcacatgta tggaaagtaa     60
gtacctccgt acggagtact gcatgtccat ccgtacttga ggaaacgctg aggtaacatg    120
gaggtagaag aaaccacgag agactatggg ttacacctgc tcaaacccac tgcacctctc    180
ctctggggat tttccgactc ttcccctgct tgaatgcaca gacagctgtg tctttggtac    240
actttactaa agaccacagc caagcgggag aaaacgggga cgatgagtca cgtccgggag    300
attccggcct gctgtgtcgg aagcaatcag ctgagctgct caatcctgaa ctttcagtac    360
acggctgcca actgagttgc agcggtccga agcgttccga gtcctttgtc agttgctttt    420
tcgcttagtt tattccttgg accagctctt gtcaaagacc gaaaatgctt tcgggagtaa    480
gagcgcttgg gatttggggt tatgtcatag accggatgaa gtcggcctgt ggtcccttcg    540
ttttcctgcc ttccccttga ggtggcttgc gaacaaacgt ataaatgatg tatcactctc    600
caagacatgc ccgtactcgc cttgatgaat ctcagactcg tgatccatcg cgacaagaca    660
gtatattggc agccatctgt ctgttgaagc tttcaacccc                          700
```

<210> SEQ ID NO 36
<211> LENGTH: 560
<212> TYPE: DNA
<213> ORGANISM: Artificial sequence
<220> FEATURE:
<223> OTHER INFORMATION: Synthetic oligonucleotide

<400> SEQUENCE: 36

```
acggagtact gcatgtccat ccgtacttga ggaaacgctg aggtaacatg gaggtagaag     60
aaaccacgag agactatggg ttacacctgc tcaaacccac tgcacctctc ctctggggat    120
tttccgactc ttcccctgct tgaatgcaca gacagctgtg tctttggtac actttactaa    180
agaccacagc caagcgggag aaaacgggga cgatgagtca cgtccgggag attccggcct    240
gctgtgtcgg aagcaatcag ctgagctgct caatcctgaa ctttcagtac acggctgcca    300
actgagttgc agcggtccga agcgttccga gtcctttgtc agttgctttt tcgcttagtt    360
tattccttgg accagctctt gtcaaagacc gaaaatgctt tcgggagtaa gagcgcttgg    420
gatttggggt tatgtcatag accggatgaa gtcggcctgt ggtcccttcg ttttcctgcc    480
ttccccttga ggtggcttgc gaacaaacgt ataaatgatg tatcactctc caagacatgc    540
ccgtactcgc cttgatgaat                                                560
```

<210> SEQ ID NO 37
<211> LENGTH: 490
<212> TYPE: DNA
<213> ORGANISM: Artificial sequence
<220> FEATURE:
<223> OTHER INFORMATION: Synthetic oligonucleotide

<400> SEQUENCE: 37

```
agactatggg ttacacctgc tcaaacccac tgcacctctc ctctggggat tttccgactc    60
ttcccctgct tgaatgcaca gacagctgtg tctttggtac actttactaa agaccacagc   120
caagcgggag aaaacgggga cgatgagtca cgtccgggag attccggcct gctgtgtcgg   180
aagcaatcag ctgagctgct caatcctgaa ctttcagtac acggctgcca actgagttgc   240
agcggtccga agcgttccga gtcctttgtc agttgctttt tcgcttagtt tattccttgg   300
accagctctt gtcaaagacc gaaaatgctt tcgggagtaa gagcgcttgg gatttggggt   360
tatgtcatag accggatgaa gtcggcctgt ggtcccttcg ttttcctgcc ttccccttga   420
ggtggcttgc gaacaaacgt ataaatgatg tatcactctc caagacatgc ccgtactcgc   480
cttgatgaat                                                          490

<210> SEQ ID NO 38
<211> LENGTH: 450
<212> TYPE: DNA
<213> ORGANISM: Artificial sequence
<220> FEATURE:
<223> OTHER INFORMATION: Synthetic oligonucleotide

<400> SEQUENCE: 38
ttcccctgct tgaatgcaca gacagctgtg tctttggtac actttactaa agaccacagc    60
caagcgggag aaaacgggga cgatgagtca cgtccgggag attccggcct gctgtgtcgg   120
aagcaatcag ctgagctgct caatcctgaa ctttcagtac acggctgcca actgagttgc   180
agcggtccga agcgttccga gtcctttgtc agttgctttt tcgcttagtt tattccttgg   240
accagctctt gtcaaagacc gaaaatgctt tcgggagtaa gagcgcttgg gatttggggt   300
tatgtcatag accggatgaa gtcggcctgt ggtcccttcg ttttcctgcc ttccccttga   360
ggtggcttgc gaacaaacgt ataaatgatg tatcactctc caagacatgc ccgtactcgc   420
cttgatgaat ctcagactcg tgatccatcg                                    450

<210> SEQ ID NO 39
<211> LENGTH: 400
<212> TYPE: DNA
<213> ORGANISM: Artificial sequence
<220> FEATURE:
<223> OTHER INFORMATION: Synthetic oligonucleotide

<400> SEQUENCE: 39
ttcccctgct tgaatgcaca gacagctgtg tctttggtac actttactaa agaccacagc    60
caagcgggag aaaacgggga cgatgagtca cgtccgggag attccggcct gctgtgtcgg   120
aagcaatcag ctgagctgct caatcctgaa ctttcagtac acggctgcca actgagttgc   180
agcggtccga agcgttccga gtcctttgtc agttgctttt tcgcttagtt tattccttgg   240
accagctctt gtcaaagacc gaaaatgctt tcgggagtaa gagcgcttgg gatttggggt   300
tatgtcatag accggatgaa gtcggcctgt ggtcccttcg ttttcctgcc ttccccttga   360
ggtggcttgc gaacaaacgt ataaatgatg tatcactctc                         400

<210> SEQ ID NO 40
<211> LENGTH: 250
<212> TYPE: DNA
<213> ORGANISM: Artificial sequence
<220> FEATURE:
<223> OTHER INFORMATION: Synthetic oligonucleotide

<400> SEQUENCE: 40
gtcctttgtc agttgctttt tcgcttagtt tattccttgg accagctctt gtcaaagacc    60
```

```
gaaaatgctt tcgggagtaa gagcgcttgg gatttggggt tatgtcatag accggatgaa    120
gtcggcctgt ggtcccttcg ttttcctgcc ttcccttga ggtggcttgc gaacaaacgt    180
ataaatgatg tatcactctc caagacatgc ccgtactcgc cttgatgaat ctcagactcg    240
tgatccatcg                                                         250
```

<210> SEQ ID NO 41
<211> LENGTH: 2613
<212> TYPE: DNA
<213> ORGANISM: Chrysosporium lucknowense

<400> SEQUENCE: 41

```
atgaaggctg ctgcgctttc ctgcctcttc ggcagtaccc ttgccgttgc aggcgccatt     60
gaatcgagaa aggttcacca gaagcccctc gcgagatctg aaccttttta cccgtcgcca    120
tggatgaatc ccaacgccga cggctgggcg gaggcctatg cccaggccaa gtcctttgtc    180
tcccaaatga ctctgctaga aaggtcaac ttgaccacgg gagtcggctg ggggctgag     240 cagtgcgtcg gccaagtggg cgcgatccct cgccttggac ttcgcagtct gtgcatgcat    300
gactcccctc tcggcatccg aggagccgac tacaactcag cgttccctc tggccagacc    360 gttgctgcta cctgggatcg cggtctgatg taccgtcgcg gctacgcaat gggccaggag    420
gccaaaggca aggcatcaa tgtccttctc ggaccagtcg ccggcccct tggccgcatg    480 cccgagggcg gtcgtaactg ggaaggcttc gctccggatc ccgtccttac cggcatcggc    540
atgtccgaga cgatcaaggg cattcaggat gctggcgtca tcgcttgtgc gaagcacttt    600
attggaaacg agcaggagca cttcagacag gtgccagaag cccagggata cggttacaac    660
atcagcgaaa ccctctcctc caacattgac gacaagacca tgcacgagct ctaccttgg    720 ccgtttgccg atgccgtccg gccggcgtc ggctctgtca tgtgctcgta ccagcaggtc    780
aacaactcgt acgcctgcca gaactcgaag ctgctgaacg acctcctcaa gaacgagctt    840
gggtttcagg gcttcgtcat gagcgactgg caggcacagc acactggcgc agcaagcgcc    900
gtggctggtc tcgatatgtc catgccgggc gacacccagt tcaacactgg cgtcagttc    960 tggggcgcca atctcaccct cgccgtcctc aacggcacag tccctgccta ccgtctcgac   1020
gacatggcca tgcgcatcat ggccgccctc ttcaaggtca ccaagaccac cgacctggaa   1080
ccgatcaact tctccttctg gaccgacgac acttatggcc cgatccactg ggccgccaag   1140
cagggctacc aggagattaa ttcccacgtt gacgtccgcg ccgaccacgg caacctcatc   1200
cgggagattg ccgccaaggg tacggtgctg ctgaagaata ccggctctct accccctgaac   1260 aagccaaagt tcgtggccgt catcggcgag gatgctgggt cgagcccaa cgggcccaac   1320 ggctgcagcg accgcggctg taacgaaggc acgctcgcca tgggctgggg atccggcaca   1380
gccaactatc cgtacctcgt tccccccgac gccgcgctcc aggcccgggc catccaggac   1440
ggcacgaggt acgagagcgt cctgtccaac tacgccgagg aaaagacaaa ggctctggtc   1500
tcgcaggcca atgcaaccgc catcgtcttc gtcaatgccg actcaggcga ggctacatc   1560 aacgtggacg gtaacgaggg cgaccgtaag aacctgactc tctggaacaa cggtgatact   1620
ctggtcaaga acgtctcgag ctggtgcagc aacaccatcg tcgtcatcca ctcggtcggc   1680
ccggtcctcc tgaccgattg gtacgacaac cccaacatca cggccattct ctgggctggt   1740
cttccgggcc aggagtcggg caactccatc ccgacgtgc tttacggcaa ggtcaacccc   1800
gccgcccgct cgcccttcac ttggggcaag accgcgaaa gctatggcgc ggacgtcctg   1860
```

```
tacaagccga ataatggcaa tggtgcgccc caacaggact tcaccgaggg cgtcttcatc   1920
gactaccgct acttcgacaa ggttgacgat gactcggtca tctacagagtt cggccacggc   1980 ctgagctaca ccaccttcga gtacagcaac atccgcgtcg tcaagtccaa cgtcagcgag   2040
taccggccca cgacgggcac cacggcccag gccccgacgt ttggcaactt ctccaccgac   2100
ctcgaggact atctcttccc caaggacgag ttcccctaca tctaccagta catctacccg   2160
tacctcaaca cgaccgaccc ccggagggcc tcggccgatc cccactacgg ccagaccgcc   2220
gaggagttcc tcccgcccca cgccaccgat gacgaccccc agccgctcct ccggtcctcg   2280
ggcggaaact cccccggcgg caaccgccag ctgtacgaca ttgtctacac aatcacggcc   2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                 2613
```

<210> SEQ ID NO 42
<211> LENGTH: 870
<212> TYPE: PRT
<213> ORGANISM: Chrysosporium lucknowense

<400> SEQUENCE: 42

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240
```

-continued

```
Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Gln Ala Gln His Thr Gly Ala Ala Ser Ala Val Ala Gly Leu
    290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Asp Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Ser Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Lys Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
        515                 520                 525

Arg Lys Asn Leu Thr Leu Trp Asn Asn Gly Asp Thr Leu Val Lys Asn
    530                 535                 540

Val Ser Ser Trp Cys Ser Asn Thr Ile Val Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
    610                 615                 620

Asn Gly Asn Gly Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
```

-continued

```
              660                 665                 670
Val Val Lys Ser Asn Val Ser Glu Tyr Arg Pro Thr Thr Gly Thr Thr
            675                 680                 685

Ala Gln Ala Pro Thr Phe Gly Asn Phe Ser Thr Asp Leu Glu Asp Tyr
            690                 695             700

Leu Phe Pro Lys Asp Glu Phe Pro Tyr Ile Tyr Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
            755                 760                 765

Arg Gln Leu Tyr Asp Ile Val Tyr Thr Ile Thr Ala Asp Ile Thr Asn
            770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
                820                 825                 830

Arg Asp Leu Ser Asn Trp Asp Val Thr Val Gln Asp Trp Val Ile Ser
            835                 840                 845

Arg Tyr Pro Lys Thr Ala Tyr Val Gly Arg Ser Ser Arg Lys Leu Asp
    850                 855                 860

Leu Lys Ile Glu Leu Pro
865             870
```